United States Patent [19]
Wright et al.

[11] Patent Number: 6,121,000
[45] Date of Patent: Sep. 19, 2000

[54] ANTITUMOR ANTISENSE SEQUENCES DIRECTED AGAINST R1 AND R2 COMPONENTS OF RIBONUCLEOTIDE REDUCTASE

[75] Inventors: Jim A. Wright; Aiping H. Young, both of Toronto, Canada

[73] Assignee: Genesense Technologies, Inc., Toronto, Canada

[21] Appl. No.: 09/249,730

[22] Filed: Feb. 11, 1999

[51] Int. Cl.$^7$ .............................. C12Q 1/68; C07H 21/04; C12N 15/63

[52] U.S. Cl. ........................... 435/6; 435/320.1; 536/23.1; 536/24.5

[58] Field of Search .................. 435/6, 320.1; 536/23.1, 536/24.5

[56] References Cited

U.S. PATENT DOCUMENTS

| | | | |
|---|---|---|---|
| 5,023,252 | 6/1991 | Hseih | 514/183 |
| 5,034,506 | 7/1991 | Summerton et al. | 528/391 |
| 5,225,347 | 7/1993 | Goldberg et al. | 435/320.1 |
| 5,580,859 | 12/1996 | Felgner et al. | 514/44 |
| 5,719,262 | 2/1998 | Buchardt et al. | 530/300 |
| 5,766,855 | 6/1998 | Buchardt et al. | 435/6 |

FOREIGN PATENT DOCUMENTS

| | | |
|---|---|---|
| WO 94/21661 | 9/1994 | WIPO. |
| WO 95/02069 | 1/1995 | WIPO. |
| WO 98/05769 | 12/1998 | WIPO. |

OTHER PUBLICATIONS

Agarwal, et al., (1995) *Oncogene*, 11:427–438.
Agrawal, (1996) "Antisense oligonucleotides: Towards clinical trials," *TIBTECH*, 14:376–387.
Akhter, et al., (1991) "Interactions of antisense DNA oligonucleotide analogs with phospholipid membranes (liposomes)," *Nucleic Acids Res.*, 19:5551–5559.
Alessi, et al., (1995) *Meth. Enzymol.*, 255:279–290.
Altschul, S.F., et al., (1990) "Basic local alignment search tool," *J. Mol. Biol.*, 215:403–410.
Amara, et al., (1994) "Phorbol ester modulation of a novel cytoplasmic protein binding activity at the 3'-untranslated region of mammalian ribonucleotide reductase R2 mRNA and role in message stability," *J. Biol. Chem.*, 269:6709–6715.
Amara, et al., (1995) "Defining a novel cis element in the 3'-untranslated region of mammalian ribonucleotide reductase component R2 mRNA: Role in transforming growth factor-$\beta_1$ inducted mRNA stabilization," *Nucleic Acids Res.*, 23:1461–1467.
Amara, et al., (1996) "Defining a novel cis–element in the 3'-untranslated region of mammalian ribonucleotide reductase component R2 mRNA: cis–trans interactions and message stability," *J. Biol. Chem.*, 271:20126–20131.
Anazodo, et al., (1995) "Sequence–specific inhibition of gene expression by a novel antisense oligodeoxynucleotide phosphorothioate directed against a nonregulatory region of the human immunodeficiency virus type 1 genome," *J. Virol.*, 69:1794–1801.

Anazodo, et al., (1996) "Relative levels of inhibition of p24 gene expression by different 20–mer antisense oligonucleotide sequences targeting nucleotides +1129 to +1268 of the HIV–1 gag genome: An analysis of mechanism," *Biochem. Biophys. Res. Commun.*, 229:305–309.
Ashihara, et al., (1979) "Cell Synchronization," *Methods Enzymol.*, 58:248–262.
Barker, R.H. Jr., et al., (1996) "Inhibition of *plasmodium falciparum* malaria using antisense oligodeoxynucleotides," *Proc. Natl. Acad. Sci. USA*, 93(1):514–518.
Blaess, (1997) "Gene Therapy for Cancer," *Scientific American*, 276(6):111–115.
Björklund, S., et al., (1990) "S–phase–specific expression of mammalian ribonucleotide reductase R1 and R2 subunit mRNAs," *Biochemistry*, 29(23):5452–5458.
Björklund, et al., (1993) "Structure and promoter characterization of the gene encoding the large subunit (R1 Protein) of mouse ribonucleotide reductase," *Proc. Natl. Acad. Sci. USA*, 90:11322–11326.
Blin, et al., (1976) "A general method of isolation of high molecular weight DNA from eukaryotes," *Nucleic Acids Res.*, 3:2303–2308.
Blosmanis, et al., (1987) *Cancer Res.*, 47:1273–1277.
Boven, et al., (1992) "Phase II preclinical drug screening in human tumor xenografts: A first European multicenter collaborative study," *Cancer Res.*, 52:5940–5947.
Bradley, et al., (1986) *Proc. Natl. Acad. Sci. USA*, 83:5277–5281.
Branch, (1998) *TIBS*, 23:45–50.
Brower, et al. (1998) "All clear for HIV–targeting ribozyme in phase II," *Nature Biotechnology*, 162(2):123.
Calabretta, et al., (1996) "Antisense strategies in the treatment of leukemias," *Semin. Oncol.*, 23:78.
Caras, (1985) "Cloned mouse ribonucleotide reductase subunit M1 cDNA reveals amino acid sequence homology with *Escherichia coli* and herpes virus ribonucleotide reductases," *Biol Chem.*, 260:7015–7022.
Chadee, et al., (1995) *J. Biol. Chem.*, 270:20098–20105.
Chakrabarti, D., et al., (1993) "Cloning and characterization of subunit genes of ribonucleotide reductase, a cell–cycle–regulated enzyme, from *Plasmodium falciparum*," *Proc. Natl. Acad. Sci. USA*, 90:12020–12024.
Chan, et al., (1993) *Biochemistry*, 32:12835–12840.
Chang, et al., (1978) "Phenotypic expression in *E. coli* of a DNA sequence coding for mouse dihydrofolate reductase," *Nature*, 275:617–624.

(List continued on next page.)

*Primary Examiner*—David Guzo
*Assistant Examiner*—Andrew Wang
*Attorney, Agent, or Firm*—Burns, Doane, Swecker & Mathis, LLP

[57] ABSTRACT

Compounds and methods for modulating cell proliferation, preferably inhibiting the proliferation of tumor cells are described. Compounds that may be used to modulate cell proliferation include antisense oligonucleotides complementary to regions of the mammalian ribonucleotide reductase genes.

11 Claims, 23 Drawing Sheets

OTHER PUBLICATIONS

Chaudhuri, M.M., et al., (1992) "cDNA sequence of the small subunit of the hamster ribonucleotide reductase," *Biochimica et Biophysica Acta*, 1171:117–121.

Chen, et al., (1993) "Mammalian ribonucleotide reductase R1 mRNA stability under normal and phorbol ester stimulating conditions: Involvement of a cis–trans interaction at the 3'–untranslated region," *EMBO J.*, 12:3977–3986.

Chen, et al., (1994). "Defining a novel ribonucleotide reductase R1 mRNA cis element that binds to an unique cytoplasmic trans–acting protein," *Nucleic Acids Res.*, 22:4796–4797.

Choy, et al., (1988) "Molecular mechanisms of drug resistance involving ribonucleotide reductase: Hydroxyurea resistance in a series of clonally related mouse cell lines selected in the presence of increasing drug concentrations," *Cancer Res.*, 48:2029–2035.

Choy, et al., (1989) *Biochem. Biophys. Res. Commun.*, 162:1417–1424.

Cole, et al., (1992) *Science*, 258:1650–1654.

Cregg, J.M., et al., (1993) "Recent advances in the expression of foreign genes in *pichia pastoris*,"*Bio/Technology*, 11:905–910.

Crooke, (1995) "Progress in antisense therapeutics," *Hematol. Pathol.*, 2:59–72.

Damen, et al., (1989) "Generation of metastatic variants in populations of mutator and amplificator mutants," *J. Natl. Cancer Inst.*, 81:628–631.

Damen, et al., (1991) "Transformation and amplification of the K–fgf Protooncogene in NIH–3T3 cells, and induction of metastatic potential," *Biochem. Biophys. Acta*, 1097:103–110.

Davis, et al., (1994) "Purification, characterization, and localization of subunit interaction area of recombinant mouse ribonucleotide reductase R1 subunit," *Biol. Chem.*, 269:23171–23176.

Devereux, J., et al., (1984) "A comprehensive set of sequence analysis programs for the VAX," *Nucleic Acids Res.*, 12:387–395.

Eckstein, (1985) "Nucleoside phosphorothioates,"*Ann. Rev. Biochem.*, 54:367–402.

Edwards, et al., (1985) *Mol. Cell. Biol.*, 5:3280–3288.

Egan, et al., (1987) "Expression of H–ras correlates with metastatic potential: Evidence for direct regulation of the metastatic phenotype in 10T½ and NIH 3T3 cells," *Mol. Cell. Biol.*, 7:830–837.

Eriksson, et al., (1984) "Cell cycle–dependent regulation of mammalian ribonucleotide reductase: The S phase–correlated increase in subunit M2 is regulated by de novo protein synthesis," *J. Biol. Chem.*, 259:11695–11700.

Fan, et al., (1996) "Ribonucleotide reductase R2 component is a novel malignancy determinant that cooperates with activated oncogenes to determine transformation and malignant potential," *Proc. Natl. Acad. Sci. USA*, 93:14036–14040.

Fan, et al., (1996) "A link between ferritin gene expression and ribonucleotide reductase R2 protein, as demonstrated by retroviral vector mediated stable expression of R2 cDNA," *FEBS Lett.*, 382:145–148.

Fan, et al., (1997) "The R1 component of mammalian ribonucleotide reductase has malignancy–suppressing activity as demonstrated by gene transfer experiments," *Proc. Natl. Acad. Sci. USA*, 94:13181–13186.

Felgner, (1997) "Nonviral strategies for gene therapy," *Scientific American*, Jun., 1997, pp. 102–106.

Flintoff, (1989) "Methotrexate," in: R.S. Gupta (ed.), *Drug Resistance in Mammalian Cells*, (pp. 1–14) Boca Raton, Florida: CRC Press.

Flory, C.M., et al., (1996) "Nuclease–resistant ribozymes decrease stromelysin mRNA levels in rabbit synovium following exogenous delivery to the knee joint," *Proc. Natl. Acad. Sci. USA*, 93:754–758.

Fujita, et al., (1980) "Relationship of chemotherapy on human cancer xenografts in nude mice to clinical response in donor patient," *Journal of Surgical Oncology*, 15:211–219.

Fujita, et al., (1982) "Application of nude mouse–human cancer xenograft systems for sensitivity test of anticancer drugs," *Gan To Kagaku Ryoho*, 9(4):606–615 (English abstract).

Fujita, et al., (1984) "Experimental chemotherapy of human gastrointestinal and breast cancers in nude mice and its correlation to clinical effect," *Gan No Rinsho*, 30(9 Supp):1168–1174 (English abstract).

Fujita, et al., (1991) "Predictability of preclinical evaluation of anticancer drugs by human gastrointestinal cancer–nude mouse panel," *Gan To Kagaku Ryoho*, 18(9):1429–1437 (English abstract).

Furukawa, et al., (1993) "Orthotopic transplantation of histologically intact clinical specimens of stomach cancer to nude mice: Correlation of metastic sites in mouse and individual patient donors," *Int. J. Cancer*, 53:608–612.

Gannon, et al., (1990) "Activating mutations in p53 produce a common conformational effect: A monoclonal antibody specific for the mutant form," *EMBO J.*, 9:1595–1602.

Gewirtz, (1993) "Oligodeoxynucleotide–based therapeutics for human leukemias," *Stem. Cells. Dayt.*, 11:96–103.

Gerwitz, et al., (1996) *Proc. Natl. Acad. Sci. USA*, 93:3161–3163.

Gilboa, et al., (1986) "Transfer and expression of cloned genes using retroviral vectors," *BioTechniques*, 4(6):504–512.

Giovanella, et al., (1983) "Correlation between response to chemotherapy of human tumors in patients and in nude mice," *Cancer*, 52:1146–1152.

Good, et al., (1998) "Inhibition of translation and bacterial growth by peptide nucleic acid targeted to ribosomal RNA," *Proc. Natl. Acad. Sci. USA*, 95:2073–2076.

Greene, L.A., et al., (1976) "Establishment of a noradrenergic clonal line of rat adrenal pheochromocytoma cells which respond to nerve growth factor," *Proc. Natl. Acad. Sci. USA*, 73(7):2424–2428.

Gubler, U., et al,. (1983) "A simple and very efficient method for generating cDNA libraries," *Gene*, 25:263–269.

Gura, (1997) *Science*, 278:1041–1042.

Hampel, et al., (1989) "RNA catalytic properties of the minimum (–) sTRSV sequence," *Biochemistry*, 28:4929–4933.

Hanania, et al., (1995) "Recent advances in the application of gene therapy to human disease," *Am. J. Med.*, 99:537–552.

Hards, et al., (1981) "N–carbamoyloxyurea–resistant Chinese hamster ovary cells with elevated levels of ribonucleotide reductase activity," *J. Cell. Physiol.*, 106:309–319.

Huang, A., et al., (1994) "Fibroblast growth factor mediated alterations in drug resistance and evidence of gene amplification," *Oncogene*, 9:491–499.

Huang, A., et al., (1995) "Drug resistance and gene amplification potential regulated by transforming growth factor $\beta_1$ gene expression," *Cancer Res.*, 55:1758–1762.

Huang, A., et al., (1995) "Multiple effects on drug sensitivity, genome stability and malignant potential by combinations of H–ras, c–myc and mutant p53 gene overexpression," *Int. J. Oncol.*, 7:57–63.

Huang, A., et al., (1997) "Ribonucleotide reductase R2 gene expression and changes in drug sensitivity and genome stability," *Cancer Research*, 57:4876–4881.

Hunter, (1995) "Protein kinases and phosphatases: The yin and yang of protein phosphorylation and signaling," *Cell*, 80:225–236.

Hurta, R.A.R., et al., (1991) "Early induction of ribonucleotide reductase gene expression by transforming growth factor $\beta_1$ in malignant H–ras transformed cell lines," *J. Biol. Chem.*, 266(35):24097–24100.

Hurta, R.A.R., et al., (1992) "Alterations in the activity and regulation of mammalian ribonucleotide reductase by chlorambucil, a DNA damaging agent," *J. Biol. Chem.*, 267:7066–7071.

Hurta, R.A.R., et al., (1994) *J. Cell Physiol.*, 158:187–197.

Hurta, R.A.R., et al., (1995) "Malignant transformation by H–ras results in aberrant regulation of ribonucleotide reductase gene expression by transforming growth factor–$\beta_1$," *J. Cell. Biochem.*, 57:543–556.

Jelinek, et al., (1994) *Mol. Cell. Biol.*, 14:8212–8218.

Jensen, et al., (1994) "Identification of genes expressed in premalignant breast disease by microscopy–directed cloning," *Proc. Natl. Acad. Sci. USA*, 91:9257–9261.

Kern, et al., (1992) "Oncogenic forms of p53 inhibit p53–regulated gene expression," *Science*, 256:827–830.

Kijima, H., et al., (1995) "Therapeutic applications of ribozymes," *Pharmac. Ther.*, 68(2):247–267.

Kohn, (1996) "Regulatory genes and drug sensitivity," *J. Natl. Cancer Inst.*, 88:1255–1256.

Koong, et al., (1994) *Cancer Res.*, 54:5273–5279.

Larsson, S., et al., (1994) "Reduced $\beta_2$–microglobulin mRNA levels in transgenic mice expressing a designed hammerhead ribozyme," *Nucleic Acids Research*, 22(12):2242–2248.

Leevers, et al., (1994) *Nature*, 369:411–414.

Lefebvre–d'Hellencourt, et al., (1995) "Immunomudulation by cytokine antisense oligonucleotides," *Eur. Cytokine Netw.*, 6:7–19.

Lenormand, et al., (1996) *J. Biol. Chem.*, 271:15762–15768.

Lewis, et al., (1978) "Assay of ribonucleotide reduction in nucleotide–permeable hamster cells," *J. Cell Physiol.*, 94:287–298.

L'Huillier, P.J., et al., (1996) "Efficacy of hammerhead ribozymes targeting α–lactalbumin transcripts: Experiments in cells and transgenic mice," *Nucleic Acids and Molecular Biology*, 10:283–300.

Livingstone, et al., (1992) "Altered cell cycle arrest and gene amplification potential accompany loss of wild type p53," *Cell*, 70:923–935.

Loke, et al., (1989) "Characterization of oligonucleotide transport into living cells," *Proc. Natl. Acad. Sci. USA*, 86:3474–3478.

Lowe, et al., (1994) "Abrogation of oncogene–associated apoptosis allows transformation of p53–deficient cells," *Proc. Natl. Acad. Sci. USA*, 91:2026–2030.

Mader, R.M., et al., (1997) "Transcription and activity of 5–fluorouracil converting enzymes in fluoropyrimidine resistance in colon cancer in vitro," *Biochemical Pharmacology*, 54:1233–1242.

Mai, (1994) "Overexpression of c–myc precedes amplification of the gene encoding dihydrofolate reductase," *Gene*, 148:253–260.

Mann, et al., (1988) "Ribonucleotide reductase M1 subunit in cellular proliferation, quiescence, and differentiation," *J. Cancer Res.*, 48:5151–5156.

McClarty, et al., (1987) "Elevated expression of M1 and M2 components and drug–induced posttranscriptional modulation of ribonucleotide reductase in a hydroxyurea resistant mouse cell line," *Biochemistry*, 26:8004–8011.

McClarty, et al., (1988) "Molecular mechanisms responsible for the drug–induced posttranscriptional modulation of ribonucleotide reductase levels in a hydroxyurea–resistant mouse L cell line," *Biochemistry*, 27:7524–7531.

McClarty, et al., (1990) "Increased ferritin gene expression is associated with increased ribonucleotide reductase gene expression and the establishment of hydroxyurea resistance in mammalian cells," *J. Biol. Chem.*, 265:7539–7547.

Miller, et al., (1993) "Use of retroviral vectors for gene transfer and expression," *Meth Enzymol.*, 217:581–599.

Morrison, (1991) "Suppression of basic fibroblast growth factor expression by antisense oligonucleotides inhibits the growth of transformed human astrocytes," *J. Biol. Chem.*, 266:728–734.

Nielsen, et al., (1991) *Science*, 254:1497–1500.

Otto, et al., (1989) "Increased incident of CAD gene amplification in tumorigenic rat lines as an indicator of genomic instability of neoplastic cells," *J. Biol. Chem.*, 264:3390–3396.

Pavloff, N., et al., (1992) "Sequence analysis of the large and small subunits of human ribonucleotide reductase," *J. DNA Sequencing and Mapping*, 2:227–234.

Price, et al., (1987) *Proc Natl. Acad. Sci. USA*, 84:156–160.

Price, et al., (1993) "Increased sequence–specific p53–DNA binding activity after DNA damage is attenuated by phorbol esters," *Oncogene*, 8:3055–3062.

Qui, et al., (1995) *Nature*, 374:457–459.

Radhakrishnan, et al., (1990) "The automated synthesis of sulfur–containing oligodeoxyribonucleotides using 3H–1,2–benzodithiol–3–one 1,1 dioxide as a sulfur–transfer reagent," *J. Org. Chem.*, 55:4693–4699.

Reichard, P., (1993) "From RNA to DNA, why so many ribonucleotide reductases?" *Science*, 260:1773–1777.

Rosolen, et al., (1990) *Cancer Res.*, 50:6316–6322.

Saeki, et al., (1995) "Immunohistochemical detection of ribonucleotide reductase in human breast tumors," *Int. J. Oncol.*, 6:523–529.

Saison–Behmoaras, et al., (1991) "Short modified antisense oligonucleotides directed against Ha–ras point mutation induce selective cleavage of the mRNA and inhibit T24 cells proliferation," *EMBO J.*, 10(5):1111–1118.

Sakamoto, et al., (1993) "Accordance of the Chemosensitivity between clinical specimens and their xenografts in nude mice by SDI test and the value of in vivo chemosensitivity test using nude mice," *Gan To Kagaku Ryoho*, 20(4):447–454 (English abstract).

Salem, et al., (1993) *FEBS Letters*, 323:93–95.

Scanlon, et al., (1995) "Oligonucleotides–mediated modulation of mammalian gene expression," *FASEB J.*, 9:1288–1296.

Schabet, et al., (1998) "Animal models of leptomeningeal metastasis," *Journal of Neuro–Oncology*, 38:199–205.

Shaw, et al., (1991) "Modified deoxyoligonucleotides stable to exonuclease degradation in serum," *Nucleic Acids Res.*, 19:747–750.

Shigesada, et al., (1985) "Construction of a cDNA to the hamster CAD gene and its application toward defining the domain for aspartate transcarbamylase," *Mol. Cell. Biol.*, 5:1735–1742.

Spitzer, et al., (1988) "Inhibition of deoxynucleases by phosphorothioate groups in oligodeoxyribonucleotides," *Nucleic Acids Res.*, 16:11691–11704.

Standart, N., et al., (1990) Control of translation of masked mRNAs in clam oocytes, *Enzyme*, 44:106–119.

Standart, N., et al., (1990) "Maternal mRNA from clam oocytes can be specifically unmasked in vitro by antisense RNA complementary to the 3'–untranslated region," *Genes & Development*, 4:2157–2168.

Stark, (1993) "Regulation and mechanisms of mammalian gene amplification," *Adv. Cancer Res.*, 61:87–113.

Stoke, et al., (1994) "Activation of Raf as a result of recruitment to the plasma membrane," *Science*, 264:1463–1467.

Stubbe, (1989) "Protein radical involvement in biological catalysis?" *Annu. Rev. Biochem.*, 58:257–285.

Stull, et al., (1995) "Antigene, ribozyme and aptamer nucleic acid drugs: Progress and prospects," *Pharmaceutical Research*, 12(4):465–483.

Sullivan, (1994) "Development of ribozymes for gene therapy," *J. of Investigative Dermatology*, 103(5)Supp:86S–89S.

Symons, (1989) "Self–cleavage of RNA in the replication of small pathogens of plants and animals," *TIBS*, 14:445–450.

Symons, (1992) "Small catalytic RNAs," *Annu. Rev. Biochem.*, 61:641–671.

Takeda, et al., (1981) "Role of ribonucleotide reductase in expression of the neoplastic program," *Life Science*, 28:1007–1014.

Takenaka, et al., (1995) "Regulation of the sequence–specific DNA binding function of p53 by protein kinase C and protein phosphatases," *J. Biol. Chem.*, 270:5405–5411.

Taylor, et al., (1992) "Evidence for synergistic interactions between ras, myc and a mutant form of p53 in cellular transformation and tumor dissemination," *Oncogene*, 7:1383–1390.

Thelander, L., et al., (1980) "Ribonucleotide reductase from calf thymus: Separation of the enzyme into two nonidentical subunits, proteins M1 and M2," *J. Biol. Chem.*, 255:7426–7432.

Thelander, L., et al., (1985) "Subunit M2 of mammalian ribonucleotide reductase. Characterization of homogeneous protein isolated from M2–overproducing mouse cells," *J. Biol. Chem.*, 260:2737–2741.

Thelander, L., et al., (1986) Isolation and characterization of expressible cDNA clones encoding the M1 and M2 subunits of mouse ribonucleotide reductase, *Molecular and Cellular Biology*, 6(10):3433–3442.

Thelander, L., et al., (1989) "Molecular cloning and expression of the functional gene encoding the M2 subunit of mouse ribonucleotide reductase: a new dominant marker gene," *EMBO J.*, 8(9):2475–2479.

Tonin, et al., (1987) "Chromosomal assignment of amplified genes in hydroxyurea resistant hamster cells," *Cytogenet. Cell. Genet.*, 45:102–108.

Uhlenbeck, (1987) " A Small catalytic oligoribonucleotide," *Nature*, 328:596–600.

Wagner, (1994) "Gene inhibition using antisense oligodeoxynucleotides," *Nature*, 372:333–335.

Wagner, et al., (1996) "Potent and selective inhibition of gene expression by an antisense heptanucleotide," *Nature Biotechnology*, 14:840–844.

Weber, (1983) "Biochemical strategy of cancer cells and the design of chemotherapy," *Cancer Res.*, 43:3466–3492.

Whitesell, et al., (1991) "Episome–generated N–myc antisense RNA restricts the differentiation potential of primitive neuroectodermal cell lines," *Mol. Cell. Biol.*, 11:1360–1371.

Winograd, et al., (1987) "Human tumor xenografts in the nude mouse and their value as test models in anticancer drug development (review)", *In Vivo*, 1(1):1–13 (abstract only).

Woolf, et al., (1990) "The stability, toxicity and effectiveness of unmodified and phosphorothioate antisense oligodeoxynucleotides in xenopus oocytes and embryos," *Nucleic Acids Res.*, 18(7):1763–1769.

Wright, et al., (1987) "Altered expression of ribonucleotide reductase and role of M2 gene amplification in hydroxyurea–resistant hamster, mouse, rat, and human cell lines," *Somat. Cell. Mol. Genet.*, 13:155–165.

Wright, (1989) "Altered mammalian ribonucleotide reductase from mutant cell lines," *Encycl. Pharmacol. Therapeut.*, 128:89–111.

Wright, et al., (1990) "Regulation and drug resistance mechanisms of mammalian ribonucleotide reductase and the significance to DNA synthesis," *Biochem. Cell. Biol.*, 68:1364–1371.

Wright, et al., (1993) "Transforming growth factor $\beta_1$ and fibroblast growth factor as promoters of tumor progression to malignancy," *Crit. Rev. Oncogen.*, 4:473–492.

Yakubov, et al., (1989) *Proc. Natl.. Acad. Sci. USA*, 86:6454–6458.

Yin, et al., (1992) "Wild–type p53 restores cell cycle control and inhibits gene amplification in cells with mutant p53 alleles," *Cell*, 70: 937–948.

FIG. 2A
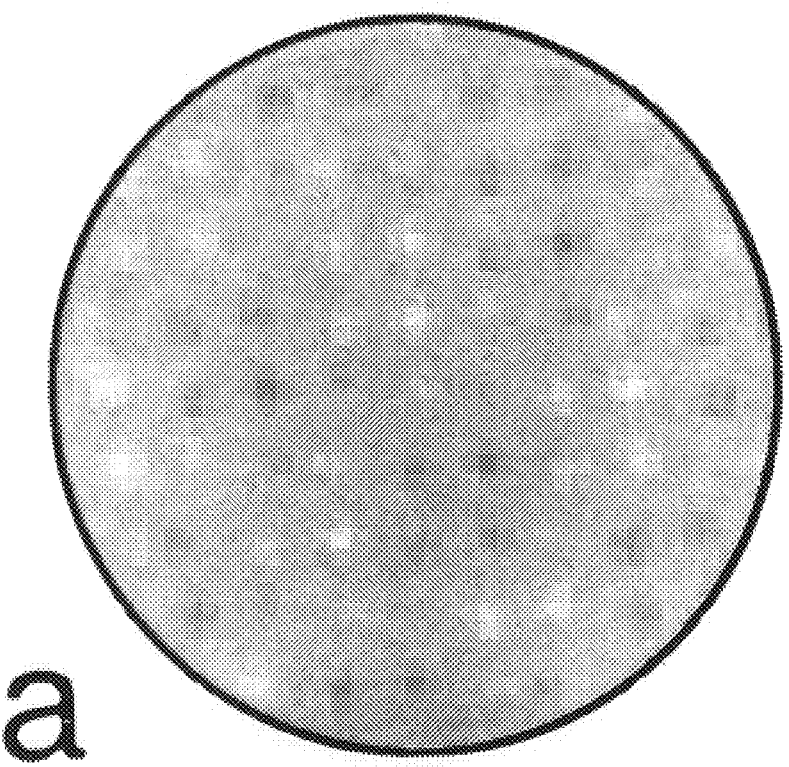
a
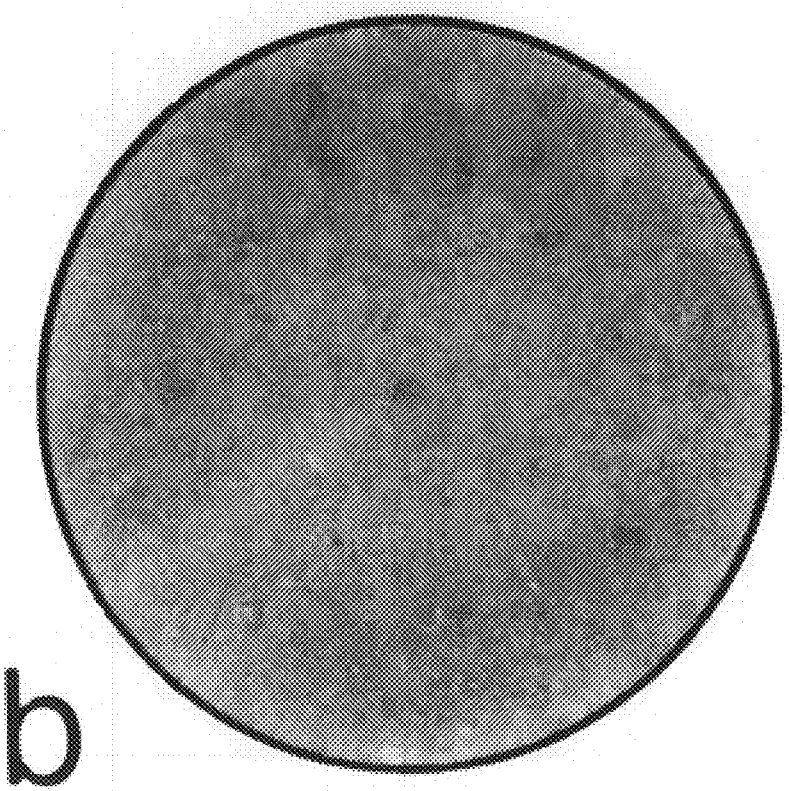
b

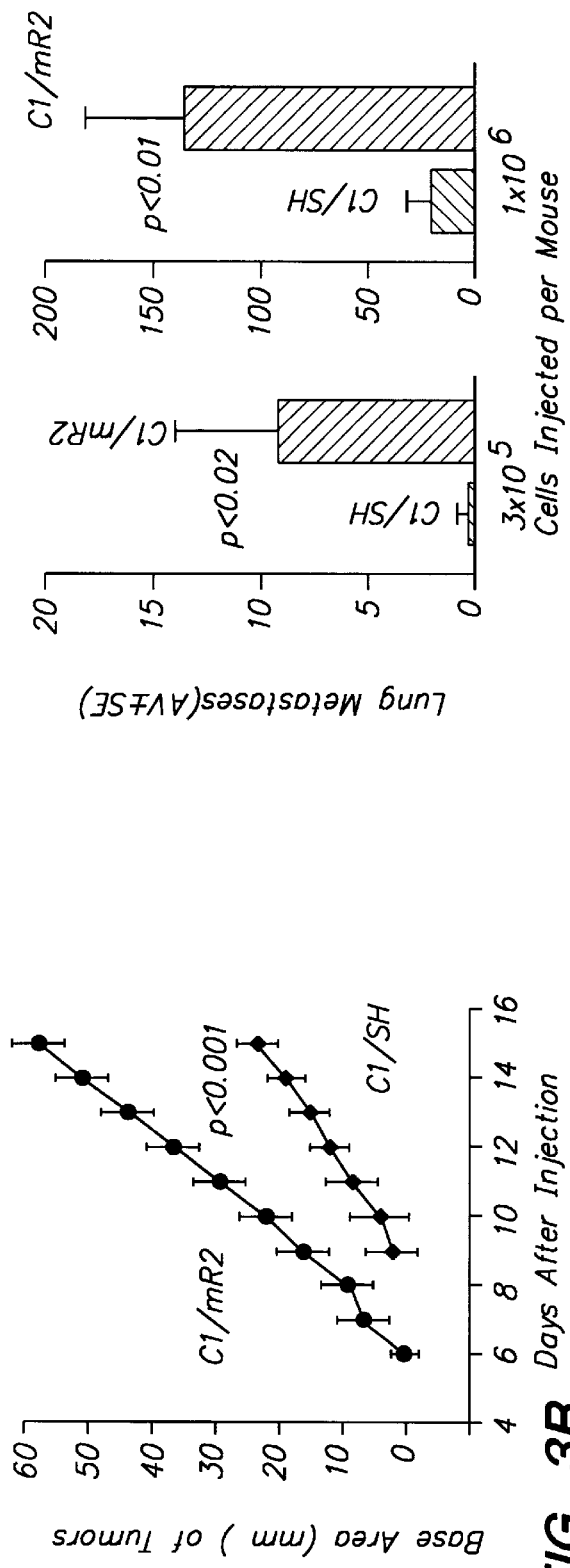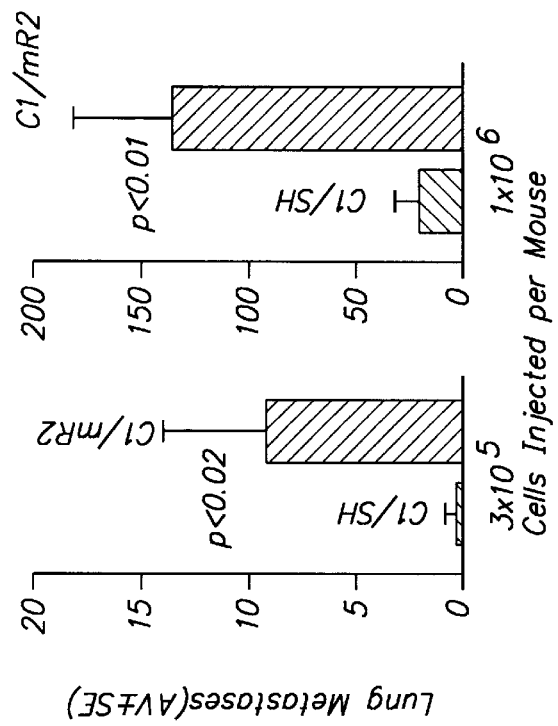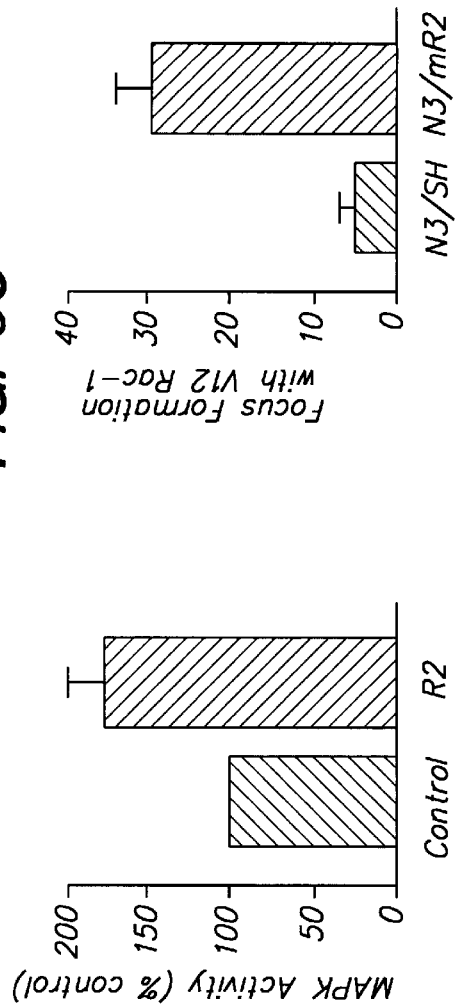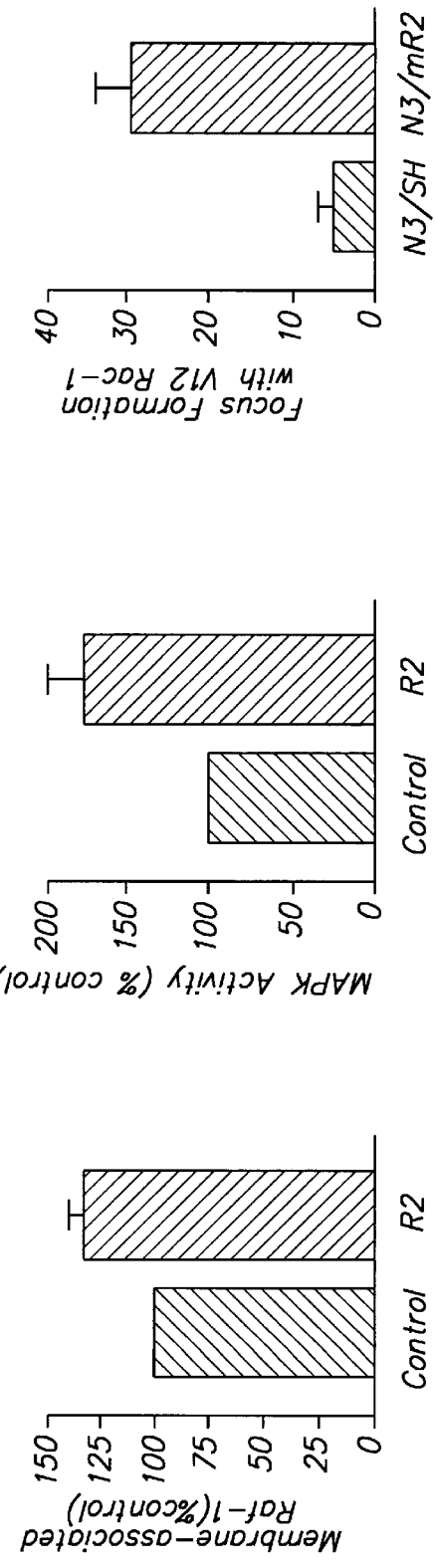

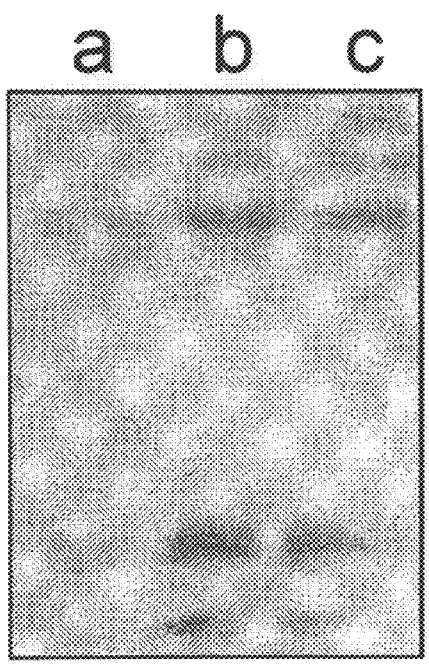 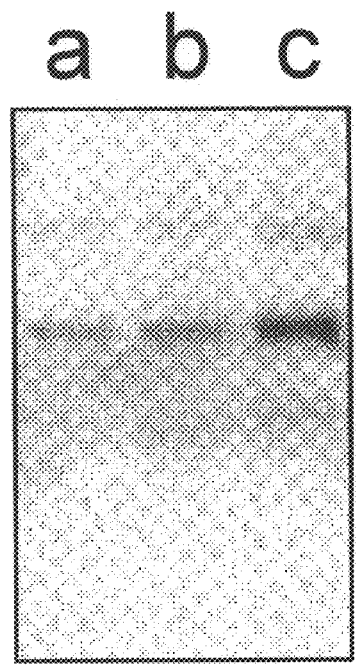

Dose Dependent Inhibition of R1 Protein Expression by AS-I-618-20

ANTITUMOR ANTISENSE SEQUENCES DIRECTED AGAINST R1 AND R2 COMPONENTS OF RIBONUCLEOTIDE REDUCTASE

BACKGROUND OF THE INVENTION

FIELD OF THE INVENTION

The field of this invention relates to methods of controlling the tumorigenicity and/or metastasis of neoplastic cells. Specifically it relates to the use of antisense sequences directed against the R1 and R2 components of mammalian ribonucleotide reductase.

REFERENCES

The following publications, patent applications and patents are cited in this application:

U.S. Pat. No. 5,034,506
U.S. Pat. No. 5,023,252 issued Jun. 11, 1991
International Patent Application No. PCT/US98/00540
Agarwal et al., (1995) Oncogene, 11:427–438
Akhter et al., (1991) "Interactions of antisense DNA oligonucleotide analogs with phospholipid membranes (liposomes)". Nucleic Acids Res. 19:5551–5559
Alessi et al., (1995) Meth. Enzyymol. 255:279–290
Altschul, et al., (1990) "Basic local alignment search tool", J. Mol. Biol. 215:403–410
Amara et al., (1994) "Phorbol ester modulation of a novel cytoplasmic protein binding activity at the 3'-untranslated region of mammalian ribonucleotide reductase R2 mRNA and role in message stability". J. Biol. Chem. 269:6709–7071
Amara et al., (1995B) "Defining a novel cis element in the 3'-untranslated region of mammalian ribonucleotide reductase component R2 mRNA: Role in transforming growth factor-β inducted mRNA stabilization". Nucleic Acids Res. 23:1461–1467
Anazodo et al., (1995) "Sequence-Specific Inhibition of Gene Expression by a Novel Antisense oligodeoxynucleotide Phosphonothioate Directed Against a Nonregulatory Region of the Human Immunodeficiency Virus Type 1 Genome". J. Virol. 69:1794–1801
Anazodo et al., (1996) "Relative Levels of Inhibition of p24 Gene Expression by different 20-mer Antisense Oligonucleotide Sequences Targeting Nucleotides +1129 to +1268 of the HIV-1 gag Genome: An Analysis of Mechanism". Biochem. Biophys. Res. Commun. 229:305–309
Ashihara and Beserga, (1979) "Cell Synchronization". Methods Enzymol. 58:248–262
Ausubel et al., Current Protocols in Molecular Biology, John Wiley and Sons, Baltimore Md. (1989)
Blaesse, (1997) "Gene Therapy for Cancer" Scientific American 276(6):111–115
Bjorklund et al., (1993) "Structure and promoter characterization of the gene coding the large subunit (R1 Protein) of mouse ribonucleotide reductase" Proc. Natl. Acad. Sci. USA 90:11322–11326
Blin and Stafford, (1976) "A general method of isolation of high molecular weight DNA from eukaryotes". Nucleic Acids Res., 3:2303–2308.
Blosmanis et al., (1987) Cancer Res. 47:1273–1277.
Bradley et al., (1986) Proc. Natl. Acad. Sci. USA 83:5277–5281.
Buchardt, deceased, et al., U.S. Pat. No. 5,766,855
Buchardt, deceased, et al., U.S. Pat. No. 5,719,262
Calabretta, et al., (1996) "Antisense strategies in the treatment of leukemias". Semin. Oncol. 23:78

Caras, (1985) "Cloned Mouse Ribonucleotide Reductase Subunit M1 cDNA Reveals Amino Acid Sequence Homology with Escherichia coli and Herpesvirus Ribonucleotide Reductases" Biol Chem. 260:7015–7022
Chadee et al., (1995) J. Biol. Chem 270:20098–20105
Chan et al., (1993) Biochemistry 32:12835–12840
Chang et al., (1978) "Phenotypic expression in E. coli of a DNA sequence coding for mouse dihydrofolate reductase" Nature, 275:617–624
Chang et al.; (1995) Somatic Gene Therapy, CRC Press, Ann Arbor Mich.
Chen et al., (1993) "Mammalian ribonucleotide reductase R1 mRNA stability under normal and phorbol ester stimulating conditions: involvement of a cis-trans interaction at the 3'-untranslated region" EMBO J., 12:3977–3986
Chen et al., (1994B). "Defining a novel ribonucleotide reductase R1 mRNA cis element that binds to an unique cytoplasmic trans-acting protein" Nucleic Acids Res. 22:4796–4797
Choy et al. (1989) Biochem Biophys Res Commun 162:1417–1424
Choy et al., (1988) "Molecular mechanisms of drug resistance involving ribonucleotide reductase: hydroxyurea resistance in a series of clonally related mouse cell lines selected in the presence of increasing drug concentrations" Cancer Res. 48:2029–2035
Crooke, (1995) "Progress in antisense therapeutics", Hematol. Pathol. 2:59
Damen et al., (1989) "Generation of metastatic variants in populations of mutator and amplificator mutants" J. Natl. Cancer Inst. 81:628–631
Damen et al., (1991) "Transformation and amplification of the K-fgf Protooncogene in NIH-3T3 cells, and induction of metastatic potential" Biochem Biophys. Acta 1097:103–110
Davis et al., (1994) "Purification, Characterization, and Localization of Subunit Interaction Area of Recombinant Mouse Ribonucleotide Reductase R1 Subunit" Biol. Chem. 269:23171–23176
Devereux J. et al., (1984) "A comprehensive set of sequence analysis programs for the VAX", Nucleic Acids Res. 12:387–395
Dreeley et al.,(1992) Science, 258:1650–1654
Edwards et al., (1985) Mol Cell Biol. 5:3280–3288
Egan, et al., (1987A) "Expression of H-ras Correlates with Metastatic Potential: Evidence for Direct Regulation of the Metastatic Phenotype in 10T½ and NIH 3T3 Cells" Mol. Cell. Biol. 7:830–837
Egan et al., (1987B) "Transformation by oncogenes encoding protein kinases induces the metastatic phenotype" Science 238:202–205
Eriksson et al., (1984) "Cell cycle-dependent regulation of mammalian ribonucleotide reductase. The S phase-correlated increase in subunit M2 is regulated by de novo protein synthesis" J. Biol. Chem. 259:11695–11700
Fan et al., (1996A) "Ribonucleotide reductase R2 component is a novel malignancy determinant that cooperates with activated oncogenes to determine transformation and malignant potential" Proc. Natl. Acad. Sci. USA 93:14036–14040
Fan et al., (1996B) "A link between ferritin gene expression and ribonucleotide reductase R2 cDNA" FEBS Lett. 382:145–148
Felgner et al.,U.S. Pat. No. 5,580,859
Flintoff, (1989) Methotrexate, In: Gupta, R. S. (ed.), Drug Resistance in Mammalian Cells, Boca Raton, Fla.: CRC Press, 1–14.

Gannon et al., (1990) "Activating mutations in p53 produce a common conformational effect. A monoclonal antibody specific for the mutant from" *EMBO J.*, 9:1595–1602

Gewirtz, (1993) "Oligodeoxynucleotide-based therapeutics for human leukemias" *Stem Cells Dayt.* 11:96

Good and Nielsen; (1998) "Inhibition of translation and bacterial growth by peptide nucleic acid targeted to ribosomal RNA", *PNAS USA* 95:2073–2076

Hanania, et al., (1995) "Recent advances in the application of gene therapy to human disease" *Am J. Med.* 99:537

Hards and Wright (1981) "N-carbamoyloxyurea-resistant Chinese hamster ovary cells with elevated levels of ribonucleotide reductase activity" *J. Cell Physiol.* 106:309–319

Huang and Wright, (1994) "Fibroblast growth factor mediated alterations in drug resistance and evidence of gene amplification" *Oncogene* 9:491–499

Huang et al., (1995A) "Drug resistance and gene amplification potential regulated by transforming growth factor β gene expression" *Cancer Res.* 55:1758–1762

Huang et al., (1995B) "Multiple effects on drug sensitivity, genome stability and malignant potential by combinations of H-ras, c-myc and mutant p53 gene overexpression" *Int. J. Oncol.* 7:57–63

Hurta, et al., (1991) "Early induction of ribonucleotide reductase gene expression by transforming growth factor β in malignant H-ras transformed cell lines" *J. Biol. Chem.* 266:24097–24100

Hurta and Wright, (1992) "Alterations in the activity and regulation of mammalian ribonucleotide reductase by chlorambucil, a DNA damaging agent" *J. Biol. Chem.* 267:7066–7071

Hurta and Wright, (1995A) "Malignant transformation by H-ras results in aberrant regulation of ribonucleotide reductase gene expression by transforming growth factor-β" *J. Cell. Biochem.* 57:543–556

Hurta and Wright, (1994) *J. Cell Physiol.* 158:187–197

Jelinek et al., (1994) *Mol. Cell. Biol.,* 14:8212–8218

Jensen et al., (1994) "Identification of genes expressed in premalignant breast disease by microscopy-directed cloning" *Proc. Natl. Acad. Sci. USA.* 91:9257–9261

Kern et al., (1992) "Oncogenic forms of p53 inhibit p53-regulated gene expression" *Science,* 256:827–830

Kohn, (1996) "Regulatory genes and drug sensitivity" *J. Natl. Cancer Inst.,* 88:1255–1256

Koong et al., (1994) *Cancer Res.* 54:5273–5279

Leevers et al., (1994) *Nature,* 369:411–414

Lefebvre-d'Hellencourt et al., (1995) "Immunomodulation by cytokine antisense oligonucleotides" *Eur. Cytokine Netw.* 6:7

Lenormand et al., (1996) *J. Biol. Chem.,* 271:15762–15768

Lev-Leman et al., (1997) Antisense Oligomers in vitro and in vivo. In *Antisense Therapeutics,* A. Cohen and S. Smicek, eds (Plenum Press, New York)

Lewis et al., (1978) "Assay of ribonucleotide reduction in nucleotide-permeable hamster cells" *J. Cell Physiol.* 94:287–298

Livingston et al., (1992) "Altered cell cycle arrest and gene amplification potential accompany loss of wild type p53" *Cell.* 70:923–935

Loke et al., (1989) "Characterization of oligonucleotides transport into living cells" *PNAS USA* 86:3474

Lowe et al., (1994) "Abrogation of oncogene-associated apoptosis allows transformation of p53-deficient cells" *Proc. Natl. Acad. Sci. USA,* 91:2026–2030

Mai, (1994) "Overexpression of c-myc precedes amplification of the gene encoding dihydrofolate reductase" *Gene,* 148:253–260

Mann et al., (1988) "Ribonucleotide reductase M1 subunit in cellular proliferation, quisecence, and differentiation" *J. Cancer Res.* 48:5151–5156

McClarty et al., (1987) "Elevated expression of M1 and M2 components and drug-induced posttranscriptional modulation of ribonucleotide reductase in a hydroxyurea resistant mouse cell line" *Biochemistry* 26:8004–8011

McClarty et al., (1988) "Molecular mechanisms responsible for the drug-induced posttranscriptional modulation of ribonucleotide reductase levels in a hydroxyurea-resistant mouse L cell line" *Biochemistry,* 27:7524–7531

McClarty et al., (1990) "Increased ferritin gene expression is associated with increased ribonucleotide reductase gene expression and the establishment of hydroxyurea resistance in mammalian cells" *J. Biol. Chem.* 265:7539–7547

Miller et al., (1993) "Use of retroviral vectors for gene transfer and expression" *Meth Enzymol.* 217:581–599

Mishel and Shugi eds. Selected Methods in Cellular Immunology, W. H. Freeman & Co. (1980)

Nielsen et al. (1991) *Science* 354:1497

Otto et al., (1989) "Increased incident of CAD gene amplification in tumorigenic rat lines as an indicator of genomic instability of neoplastic cells" *J. Biol. Chem.* 264:3390–3396

Pavloff et al., (1992) *J. DNA Sequencing and Mapping* 2:227–234

*PCR Protocols: A Guide To Methods And Applications,* Academic Press, San Diego, Calif. (1990)

Perbal, *A Practical Guide to Molecular Cloning,* John Wiley & Sons, New York (1988)

Phillips, (1973) "Dye Exclusion Tests for Cell Viability" in *Tissue Culture Methods and Applications* (editors: P. F. Kruse, Jr. and M. K. Patterson, Jr.), Academic Press, New York and London, pp. 406–408

Price et al., (1987) *Proc Natl. Acad. Sci. USA* 84:156–160

Price and Calderwood, (1993) "Increased sequence-specific p53-DNA binding activity after DNA damage is attenuated by phorbol esters" *Oncogene.* 8:3055–3062

Qui et al., (1995) *Nature* 374:457–459

Reichard, (1993) "From RNA to DNA, why so many ribonucleotide redutases?" *Science* 60:1773–1777

*Remington's Pharmaceutical Sciences,* Mace Publishing Company, Philadelphia Pa. 17th ed. (1985)

Saeki et al., (1995) "Immunohistochemical detection of ribonucleotide reductase in human breast tumors" *Int. J. Oncol.* 6:523–529

Salem et al., (1993) *FEBS Letters* 323:93–95

Sambrook et al., *Molecular Cloning: A Laboratory Manual,* Cold Spring Harbor Laboratory, New York (1989, 1992)

Scanlon et al., (1995) "Oligonucleotides-mediated modulation of mammalian gene expression" *FASEB J.* 9:1288

Shaw et al., (1991) "Modified deoxyoligonucleotides stable to exonuclease degradation in serum" *Nucleic Acids Res.* 19:747–750

Shigesada et al., (1985) "Construction of a cDNA to the hamster CAD gene and its application toward defining the domain for aspartate transcarbamylase" *Mol. Cell. Biol.,* 5:1735–1742

Stark et al., (1990) Gene Rearrangements, In: B. D. Hames and D. M. Glover (eds.) *Frontiers in Molecular Biology,* Oxford, United Kingdom: IRL;99–149

Stark, (1993) "Regulation and mechanisms of mammalian gene amplification" *Adv. Cancer Res.,* 61:87–113

Stites et al., (1994) Basic and Clinical Immunology ($8^{th}$ Ed.) Appleton & Lange, Norwalk, Conn.

Stokoe et al., (1994) "Activation of Raf as a result of recruitment to the plasma membrane" *Science* 264:1463–1467

Stubbe, (1989) "Protein radical involvement in biological catalysis?" *Annu. Rev. Biochem.* 58:257–285

Sullivan (1994), U.S. Pat. No. 5,225,347

Takeda and Weber, (1981) "Role of ribonucleotide reductase in expression of the neoplastic program" Life Science 28:1007–1014

Takenaka et al., (1995) "Regulation of the sequence-specific DNA binding function of p53 by protein kinase C and protein phosphatases" *J. Biol. Chem.*, 270:5405–5411

Taylor et al., (1992) "Evidence for synergistic interactions between ras, myc and a mutant form of p53 in cellular transformation and tumor dissemination" *Oncogene* 7:1383–1390

Thelander et al., (1985) "Subunit M2 of mammalian ribonucleotide reductase. Characterization of homogeneous protein isolated from M2-overproducing mouse cells" *J. Biol. Chem.* 260:2737–2741

Thelander et al., (1980) "Ribonucleotide reductase from calf thymus. Separation of the enzyme into two nonidentical subunits, proteins M1 and M2" *J. Biol. Chem.* 255:7426–7432

Tonin et al., (1987) "Chromosomal assignment of amplified genes in hydroxyurea resistant hamster cells" *Cytogenet Cell Genet.* 45:102–108

Vega et al.; *Gene Targeting,* CRC Press, Ann Arbor Mich. (1995)

*Vectors: A Survey of Molecular Cloning Vectors and Their Uses,* Butterworths, Boston Mass. (1988)

Wagner et al., (1996) "Potent and selective inhibition of gene expression by an antisense heptanucleotide" *Nature Biotechnology* 14:840–844

Wagner, (1994) "Gene inhibition using antisense oligodeoxynucleotides" *Nature* 372:333

Weber, (1983) "Biochemical strategy of cancer cells and the design of chemotherapy" *Cancer Res.* 43:3466–3492

Wright et al., (1987) "Altered Expression of Ribonucleotide Reductase and Role of M2 Gene Amplification in Hydroxyurea-Resistant Hamster, Mouse, Rat, and Human Cell Lines" *Somat. Cell. Mol. Genet.* 13:155–165

Wright, (1989A) "Altered mammalian ribonucleotide reductase from mutant cell lines" *Encycl. Pharmacol. Therapeut.* 128:89–111

Wright et al., (1989B) Hydroxyurea and related compounds. In: R. S. Gupta (ed.), *Drug Resistance in Mammalian Cells,* Boca Raton, Fla.; CRC Press, In.; 15–27

Wright et al., (1990A) "Regulation and drug resistance mechanisms of mammalian ribonucleotide reductase and the significance to DNA synthesis" *Biochem. Cell. Biol.* 68:1364–1371

Wright et al., (1993) "Transforming growth factor β and fibroblast growth factor as promoters of tumor progression to malignancy" *Crit. Rev. Oncogen.* 4:473–492

Yakubov et al., (1989) *Proc. Natl. Acad. Sci.* USA 86:6454

Yin et al., (1992) "Wild-type p53 restores cell cycle control and inhibits gene amplification in cells with mutant p53 allels" *Cell.* 70: 937–948

U.S. application Ser. No. 08/904,901 filed Aug. 1, 1997, which in turn claims priority to U.S. Provisional Application No. 60/023,040 filed Aug. 2, 1996 and U.S. Provisional Application No. 60/039,959 filed Mar. 7, 1997

All of the above publications, patent applications and patents are herein incorporated by reference in their entirety to the same extent as if each individual publication, patent application or patent was specifically and individually indicated to be incorporated by reference in its entirety.

STATE OF THE ART

The first unique step leading to DNA synthesis is the conversion of ribonucleotides to their corresponding deoxyribonucleotides, a reaction that is catalyzed in a cell cycle specific manner by the housekeeping gene ribonucleotide reductase [Lewis et al., 1978; Reichard, 1993; Wright, 1989a; Wright et al., 1990a; Stubbe, 1989.]The mammalian enzyme is composed of two dissimilar dimeric protein components often called R1 and R2, which are encoded by two different genes located on different chromosomes [Bjorklund et al., 1993; Tonin et al., 1987]. Mammalian protein R1 is a homodimeric structure, with a molecular weight of about 170 kDa, and has substrate sites and allosteric effector sites that control enzyme activity and substrate specificity [Wright, 1989A; Thelander et al., 1980; Caras et al., 1985; Wright et al., 1990a]. Protein R2 is a homodimer, with a molecular weight of 88 kDa, and forms two equivalent dinuclear iron centers that stabilizes a tyrosyl free radical required for catalysis [Wright et al., 1990a; Thelander et al., 1985; McClarty et al., 1990.]R1 and R2 proteins interact at their C-terminal ends to form an active holoenzyme [Reichard, 1993; Wright et al., 1990a; Davis et al., 1994.]

R1 and R2 are differentially regulated during the cell cycle. There is an S-phase correlated increase in the R2 protein resulting from its de novo synthesis [Lewis et al., 1978; Mann et al., 1988.]The activity of ribonucleotide reductase, and therefore DNA synthesis and cell proliferation, is controlled in proliferating cells during the cell cycle by the synthesis and degradation of the R2 component [Eriksson et al., 1984]. The rate-limiting R2 component is a phosphoprotein capable of being phosphorylated by the CDC2 and CDK2 protein kinase mediators of cell cycle progression [Chan et al., 1993,]and contains non-heme iron that stabilizes an unique tyrosyl free radical required for enzyme activity [Reichard, 1993; McClarty et al., 1990.

The levels of the R1 protein do not appear to change substantially during the cell cycle of proliferating cells and can be detected throughout the cell cycle. Synthesis of R1 mRNA, like R2 mRNA appears to occur mainly during S phase [Eriksson et al., 1984; Choy et al., 1988; Mann et al., 1988]. The broader distribution of the R1 protein during the cell cycle is attributed to its longer half life as compared to the R2 protein [Choy et al., 1988; Mann et al., 1988].

Regulation of ribonucleotide reductase, and particularly the R2 component, is altered in malignant cells exposed to tumor promoters or to the growth factor TGF-β [Amara, et al., 1994; Chen et al., 1993; Amara et al., 1995b; Hurta and Wright, 1995A; Hurta et al., 1991]. Higher levels of enzyme activity have been observed in cultured malignant cells when compared to nonmalignant cells [Weber, 1983; Takeda and Weber, 1981; Wright et al., 1989a], and increased levels of R2 protein and R2 mRNA have been found in premalignant and malignant tissues as compared to normal control tissue samples [Saeki et al., 1995; Jensen et al., 1994].

Compounds like hydroxyurea inhibit ribonucleotide reductase activity by destabilizing the iron center of the R2 protein causing the destruction of the tyrosyl free radical [McClarty et al., 1990], and preventing cells from progressing through S-phase of the cell cycle [Ashihara and Baserga, 1979].

Breakthroughs in molecular biology and the human genome project have opened previously unforeseen possibilities for targeted intervention with mammalian gene expression [Blaese, 1997]. These include approaches such as disruption of specific genes. Antisense (AS) oligonucleotides (AS-ON) designed to hybridize with specific sequences within a targeted mRNA are one example of such targeted intervention. In general, antisense oligonucleotides interact well with phospholipid membranes [Akhter et al., 1991]. Following their interaction with the cellular plasma membrane, they may be actively, or passively, transported into living cells [Loke et al., 1989], and this may occur by a saturable mechanism predicted to involve specific receptors [Yakubov et al., 1989].

Many excellent reviews have covered the main aspects of antisense technology and its enormous therapeutic potential. There are reviews on the chemical [Crooke, 1995], cellular [Wagner, 1994] and therapeutic [Hanania, et al., 1995; Scanlon, et al., 1995; Gewirtz, 1993] aspects of this rapidly developing technology. Within a relatively short time, ample information has accumulated about the in vitro use of antisense oligonucleotides in cultured primary cells and cell lines as well as for in vivo administration of such oligonucleotides for suppressing specific processes and changing body functions in a transient manner. Further, enough experience is now available in vitro and in vivo in animal models to predict human efficacy.

In addition to the above, International Patent Application No. PCT/US98/00540 discloses that antisense oligonucleotides complementary to the R1 and R2 components of ribonucleotide reductase are useful to control tumorigenicity and/or metastatic potential in premalignant or malignant cells. While the specific oligonucleotides illustrated in that reference exhibit good antitumorigenicity, it would be advantageous to discover further antisense oligonucleotides having increased activity in controlling tumorigenicity and/or metastatic potential.

SUMMARY OF THE INVENTION

The present invention provides an antisense oligonucleotide less than about 50 nucleotides comprising the sequence of AS-I-618-20 [SEQ ID NO:176]. This sequence may further comprise a reduced dimer formation and reduced self-complementary interactions.

Also provided is a a pharmaceutical composition for inhibiting tumor cell growth in a mammal comprising an effective amount of an antisense oligonucleotide less than about 50 nucleotides comprising the sequence of AS-I-618-20 [SEQ ID NO:176].

In one of its method aspects, this invention provides a method of inhibiting the tumorigenicity of neoplastic cells in a mammal which method comprises contacting the neoplastic cell with an effective amount of an antisense oligonucleotide comprising the sequence of AS-I-618-20 [SEQ ID NO:176].

Another aspect is a method of inhibiting the tumorigenicity of neoplastic cells resistant to chemotherapeutic drugs in a mammal which method comprises identifying patients who have tumors that are resistant to a chemotherapeutic drug; and contacting the tumor with the chemotherapeutic drug to which the tumor is resistant and an antisense oligonucleotide comprising the sequence of AS-I-618-20 [SEQ ID NO:176] wherein the amount of the chemotherapeutic drug and the antisense oligonucleotide is sufficient to inhibit tumor cell growth. The amount of antisense oligonucleotide alone may be insufficient to inhibit tumor cell growth.

Another aspect is a method of increasing sensitivity of neoplastic cells to chemotherapeutic drugs in a mammal by contacting the tumor with an antisense oligonucleotide comprising the sequence of AS-I-618-20 [SEQ ID NO:176].

Another aspect is a method of inhibiting metastasis of tumor cells in a mammal which method comprises administering to said mammal an amount sufficient to inhibit tumor cell growth of an antisense oligonucleotide comprising the sequence of AS-I-618-20 [SEQ ID NO:176].

Another aspect is an isolated DNA with a sequence comprising a transcriptional initiation region and a sequence encoding an antisense oligonucleotide less than about 50 nucleotides comprising the sequence of AS-I-618-20 [SEQ ID NO:176].

BRIEF DESCRIPTION OF THE DRAWINGS

FIG. 2A–C are photographs (A and B) and a graph (C) of experiments measuring transformed foci wherein (A) shows infection of BALB/c 3T3 (a) and NIH 3T3 (b) cells with SH/mR2 did not lead to focus formation. (B) There was an increase in focus formation with B3/mR2 (b) and N3/mR2 (d) compared to B3/SH (a) and N3/SH (c) after transfection with the T24 H-ras plasmid. (C) The number of foci formed in three independent ras transfection experiments was plotted.

FIG. 3A–C are photographs of soft agar growth (A) and graphs (B and C) wherein (A) shows expression of Myc-R2 in ras-transformed cells resulted in an increased growth efficiency in soft agar. Examples shown are r-3/mR2 and uninfected r-3 cells (See Table 4). (B) C1/mR2 cells showed reduced tumor latency and increased growth rate when compared to C1/SH control cells where $3 \times 10^5$ cells from logarithmically growing cultures were collected and subcutaneously injected into five syngeneic C3H/HeN mice/cell line/experiment. Results presented are from two independent experiments. The p value of t test analysis of tumor growth rates is shown, and indicates that the growth rates for the two cell lines are significantly different. (C) C1/mR2 cells exhibited elevated metastatic potential.

FIG. 4A–C are graphs wherein (A) shows an increased amount of Raf-1 protein associated with the membrane in R2 overexpressing cells. The recombinant R2 expressing cell lines B3/mR2, N3/mR2, C1/mR2, r-2/mR2, r-3/mR2 and NR4/mR2 (R2) were compared to their respective control lines, B3/SH, N3/SH, C1/SH, r-2/SH, r-3, and NR4 (control). In all cases, cells expressing recombinant R2 exhibited increased membrane associated Raf-1 protein, and when the two groups of cell lines were compared, they were found to be significantly different by t test analysis ($p<0.001$). (B) Also shows an increase in the activity of mitogen activating protein kinase (MAPK-2) in R2 overexpressing cells. The recombinant R2 expressing lines B3/mR2, N3/mR2, 10T/mR2, C1/mR2, r-2/mR2 and NR4/mR2 (R2) were compared to their respective control lines infected with LXSH (controls). In all cases tested, cells expressing recombinant R2 showed increased enzyme activity, and the difference between two groups was highly significant ($p<0.001$). (C) Shows increased foci formation with N3/mR2 cells compared to N3/SH cells after transfection with the activated V12 Rac-1 plasmid. The number of foci shown represents the average±SE from two independent experiments.

FIG. 5A: H-4 cells not exposed to drug as a control (a), H-4 cells from a colony that developed in the presence of 50 μM PALA (b), or in the presence of 60 μM PALA (c). DNA was digested to completion with XbaI. FIG. 5B: SC2 cells not exposed to drug as a control (a), SC2 cells from colonies that developed in the presence of 80 nM methotrexate (MTx) (b) and (c). DNA was digested to completion with PstI.

FIG. 6A–B are photographs of gels showing examples of Southern blot analysis of CAD (A) and DHFR (B) DNA with BALB/c 3T3 cells. DNA was digested to completion with PstI. FIG. 6A: B3/mR2 cells not exposed to PALA (a), and B3/mR2 cells from colonies that developed in the presence of 40 μM PALA (b), or in the presence of 50 μM PALA (c). FIG. 6B: B3/mR2 cells not exposed to MTX (a), and B3/mR2 cells from colonies that developed in the presence of 60 μM MTX (b),or in the presence of 80 μM MTX (c).

FIG. 10A mouse tumor cells (a); mouse cells with AS-II-626-20 (b); mouse cells with scrambled AS-II-626-20 (c); mouse cells with mismatched AS-II-626-20 (d). FIG. 10B mouse tumor cells (a); treated with AS-II-667-20 (b); AS-II-816-20 (c); AS-II-1288-20 (d); AS-II-1335-20 (e); AS-II-1338-20 (f).

DETAILED DESCRIPTION OF THE INVENTION

Definitions

Figure 1A:
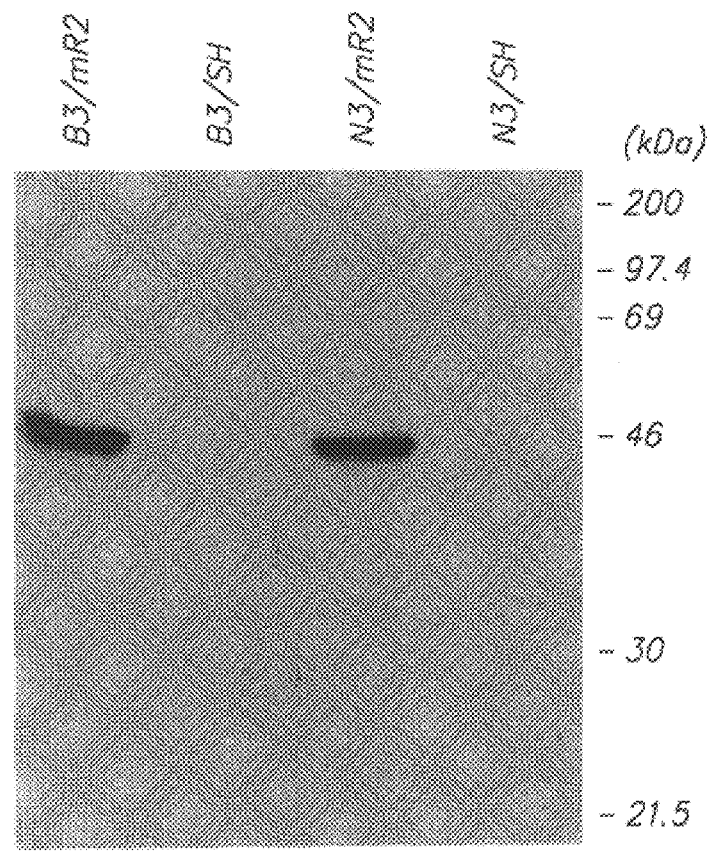
FIG. 1A–C are photographs of gels (A and B) and two scans (C) showing the analysis of Myc-eptiope tagged R2 expression from stable infectants by Western blot analysis using monoclonal anti-Myc epitope antibody 9E10 (A), polyclonal rabbit anti-R2 serum (B), and during the cell cycle by flow cytometry, using antibody 9E10 (C).

As used herein, the following terms have the following meanings:

The term "antisense oligonucleotide" as used herein means a nucleotide sequence that is complementary to the desired mRNA. Preferably, the antisense oligonucleotide is complementary to the ribonucleotide reductase mRNA. It is contemplated that the antisense oligonucleotide may be complementary to any of the 5' untranslated region of the mRNA, the coding region or the 3' untranslated region of the mRNA.

The term "oligonucleotide" refers to an oligomer or polymer of nucleotide or nucleoside monomers consisting of naturally occurring bases, sugars, and inter-sugar (backbone) linkages. The term also includes modified or substituted oligomers comprising non-naturally occurring monomers or portions thereof, which function similarly. Such modified or substituted oligomers may be preferred over naturally occurring forms because of the properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) or two or more oligonucleotides of the invention may be joined to form a chimeric oligonucleotide.

The antisense oligonucleotides of the present invention may be ribonucleic or deoxyribonucleic acids and may contain naturally occurring or synthetic monomeric bases, including adenine, guanine, cytosine, thymine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines or guanines, 5-trifluoromethyl uracil and 5-trifluoro cytosine. The modifications may also include attachment of other chemical groups, such as methyl, ethyl, or propyl groups, to the various parts of the oligonucleotides including the sugar, base or backbone components.

The antisense oligonucleotides of the invention may also comprise modified phosphorus oxygen heteroatoms in the phosphate backbone, short chain alkyl or cycloalkyl intersugar linkages or short chain heteroatom or heterocyclic intersugar linkages. For example, the antisense oligonucleotides may contain methyl phosphonates, phosphorothioates, phosphorodithioates, phosphotriesters, and morpholino oligomers. In one embodiment of the invention, the antisense oligonucleotides comprise phosphorothioate bonds linking between the four to six 3'-terminus nucleotides. In another embodiment, the phosphorothioate bonds link all the nucleotides. The antisense oligonucleotides may also have sugar mimetics.

The antisense oligonucleotides of the invention may also comprise nucleotide analogues wherein the structure of the nucleotide is fundamentally altered. An example of such an oligonucleotide analogue is a peptide nucleic acid (PNA) wherein the deoxyribose (or ribose) phosphate backbone in DNA (or RNA) is replaced with a polyamide backbone which is similar to that found in peptides (Nielsen et al. 1991; Good and Nielsen, 1998; Buchardt, deceased, et al., U.S. Pat. No. 5,766,855; Buchardt, deceased, et al., U.S. Pat. No. 5,719,262). PNA analogues have been shown to be resistant to degradation by enzymes and to have extended lives in vivo and in vitro. PNAs also bind more strongly to a complementary DNA sequence than to a naturally occurring nucleic acid molecule due to the lack of charge repulsion between the PNA strand and the DNA strand.

The oligonucleotides of the present invention may also include other nucleotides comprising polymer backbones, cyclic backbones, or acyclic backbones. For example, the nucleotides may comprise morpholino backbone structures (U.S. Pat. No. 5,034,506).

The oligonucleotides of the present invention are "nuclease resistant" when they have either been modified such that they are not susceptible to degradation by DNA and RNA nucleases or alternatively they have been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example liposomes.

The oligonucleotides of the present invention may also contain groups, such as groups for improving the pharmacokinetic properties of an oligonucleotides, or groups for improving the pharmacodynamic properties of an oligonucleotide.

The antisense oligonucleotides are preferably selected from the sequence complementary to the ribonucleotide reductase mRNA or gene sequences such that the sequence exhibits the least likelihood of showing duplex formation, hair-pin formation, and homooligomer/sequence repeats but has a high to moderate potential to bind to the ribonucleotide reductase mRNA or gene sequences. These properties may be determined using the computer modeling program OLIGO Primer Analysis Software, Version 3.4 or 5.0 (distributed by National Biosciences, Inc., Plymouth, Minn.). This computer program allows the determination of a qualitative estimation of these five parameters.

Alternatively, the antisense oligonucleotides may also be selected on the basis that the sequence is highly conserved for either the ribonucleotide reductase gene between two or more mammalian species. These properties may be determined using the BLASTN program (Altschul, et al.) of the University of Wisconsin Computer group (GCG) software (Devereux J. et al. 1994) with the National Center for Biotechnology Information (NCBI) databases.

The antisense oligonucleotides may include mutations, such as substitutions, insertions and deletions. Preferably there will be less than 10% of the sequence having mutations.

The antisense oligonucleotides generally comprise from at least about 3 nucleotides or nucleotide analogs, more preferably they are at least about 5 nucleotides, more preferably they are at least about 7 nucleotides, more preferably they are at least about 9 nucleotides and most preferably they are at least about 12 nucleotides. The antisense oligonucleotides are preferably less than about 100 nucleotides or nucleotide analogs, more preferably, less than about 50 nucleotides or nucleotide analogs, most preferably less than about 35 nucleotide or nucleotide analogs.

Preferably, the antisense oligonucleotides comprise the sequences set forth in Tables 1, 2 and 3 (below).

TABLE 1

ANTISENSE SEQUENCES DESIGNED TO TARGET THE R2 MESSAGE

| SEQ ID No: | Name | Sequence 5' - 3' | Tm (° C.) | dG Kcal/mol |
|---|---|---|---|---|
| SEQ ID No:3 | AS-II-6-20 | ACCCTTCCCATTGGCTGCGC | 62.8 | −45.5 |
| SEQ ID No:4 | AS-II-13-20 | GsCCsTCCGsACCsCTTCsCCsATTsG | 60.1 | −43.7 |
| SEQ ID No:5 | AS-II-14-20 | TGCCTCCGACCCTTCCCATT | 60.1 | −43.7 |
| SEQ ID No:6 | AS-II-16-18 | TGCCTCCGACCCTTCCCA | 58.4 | −40.3 |
| SEQ ID No:7 | AS-II-75-20 | CsGCGsCGCsTCCsCGGsCCCsTTCsC | 72.7 | −53.7 |
| SEQ ID No:8 | AS-II-75-20 | CGCGCGCTCCCGGCCCTTCC | 72.7 | −53.7 |
| SEQ ID No:9 | AS-II-79-14 | CGCGCTCCCGGCCC | 59.1 | −38.8 |
| SEQ ID No:10 | AS-II-109-20 | CsCCCsTCACsTCCsAGCsAGCsCTsT | 57.9 | −41.8 |
| SEQ ID No:11 | AS-II-110-20 | ACCCCTCACTCCAGCAGCCT | 57.3 | −41.2 |
| SEQ ID No:12 | AS-II-114-20 | GGCGACCCCTCACTCCAGCA | 61.8 | −43.2 |
| SEQ ID No:13 | AS-II-127-12 | GCACGGGCGACC | 41.7 | −28.8 |
| SEQ ID No:14 | AS-II-130-20 | TGGGACAGGGTGCACGGGCG | 67.6 | −46.7 |
| SEQ ID No:15 | AS-II-134-20 | GACGGCTGGGACAGGGTGCA | 62.6 | −43.2 |
| SEQ ID No:16 | AS-II-151-20 | GAGCAGCCAGGACAGGACGG | 59.3 | −41.7 |
| SEQ ID No:17 | AS-II-163-20 | GsCGsAAGsCAGsAGCsGAGsCAGCsC | 62.1 | −44.3 |
| SEQ ID No:18 | AS-II-166-20 | GCAGCGAAGCAGAGCGAGCA | 61.4 | −43.1 |
| SEQ ID No:19 | AS-II-185-20 | GGGAGAGCATAGTGGAGGCG | 56.0 | −40.9 |
| SEQ ID No:20 | AS-II-189-20 | CGGAGGGAGAGCATAGTGGA | 54.1 | −39.4 |
| SEQ ID No:21 | AS-II-201-20 | GCGAGCGGGACACGGAGGGA | 63.5 | −45.1 |
| SEQ ID No:22 | AS-II-217-20 | CGGGTCCGTGATGGGCGCGA | 69.5 | −48.8 |
| SEQ ID No:23 | AS-II-225-20 | AGCTGCTGCGGGTCCGTGAT | 61.4 | −43.6 |
| SEQ ID No:24 | AS-II-253-14 | CCCCTTCAGCGGCG | 50.8 | −34.4 |
| SEQ ID No:25 | AS-II-280-20 | CGGCGGCGTGTTCTCCTTGT | 61.8 | −44.2 |
| SEQ ID No:26 | AS-II-288-12 | CGGCGGCGTGTT | 43.2 | −29.6 |
| SEQ ID No:27 | AS-II-323-20 | TCCTCGCGGTCTTGCTGGCC | 64.1 | −45.5 |
| SEQ ID No:28 | AS-II-344-20 | CCGTGGGCTCCTGGAAGATC | 58.0 | −41.9 |
| SEQ ID No:29 | AS-II-362-20 | CTGCTTTAGTTTTCGGCTCC | 51.2 | −39.2 |
| SEQ ID No:30 | AS-II-391-17 | CGGCTCATCCTCCACGC | 54.5 | −37.3 |
| SEQ ID No:31 | AS-II-404-20 | GGTTTTCTCTCAGCAGCGGC | 56.4 | −41.4 |
| SEQ ID No:32 | AS-II-412-20 | GCGGCGGGGGTTTTCTCTCA | 62.8 | −45.8 |
| SEQ ID No:33 | AS-II-414-20 | AAGCGGCGGGGGTTTTCTCT | 60.7 | −45.8 |
| SEQ ID No:34 | AS-II-425-20 | GGAAGATGACAAAGCGGCGG | 59.1 | −43.0 |
| SEQ ID No:35 | AS-II-439-20 | ATGGTACTCGATGGGGAAGA | 50.8 | −37.8 |
| SEQ ID No:36 | AS-II-472-20 | AGCCTCTGCCTTCTTATACA | 46.1 | −35.8 |
| SEQ ID No:37 | AS-II-494-20 | CCTCCTCGGCGGTCCAAAAG | 60.4 | −44.3 |
| SEQ ID No:38 | AS-II-496-16 | TCCTCGGCGGTCCAAA | 54.8 | −37.0 |
| SEQ ID No:39 | AS-II-549-20 | TATCTCTCCTCGGGTTTCAG | 48.4 | −36.7 |
| SEQ ID No:40 | AS-II-579-20 | GCAAAGAAAGCCAGAACATG | 50.0 | −37.2 |
| SEQ ID No:41 | AS-II-619-20 | TCGCTCCACCAAGTTTTCAT | 52.1 | −38.3 |
| SEQ ID No:42 | AS-II-626-20 | GGCTAAATCGCTCCACCAAG | 53.9 | −40.3 |
| SEQ ID No:43 | AS-II-634-20 | AACTTCTTGGCTAAATCGCT | 48.0 | −37.6 |
| SEQ ID No:44 | AS-II-667-20 | GAAGCCATAGAAACAGCGGG | 53.9 | −40.3 |
| SEQ ID No:45 | AS-II-784-20 | GACACAAGGCATCGTTTCAA | 50.9 | −36.8 |
| SEQ ID No:46 | AS-II-798-20 | TCTGCCTTCTTCTTGACACA | 48.0 | −34.9 |
| SEQ ID No:47 | AS-II-816-20 | ATCCAGCGCAAGGCCCAGTC | 60.9 | −43.7 |
| SEQ ID No:48 | AS-II-861-20 | GCAAAGGCTACAACACGTTC | 50.0 | −37.1 |
| SEQ ID No:49 | AS-II-890-20 | AACCGGAAAAGAAAATGCCT | 52.2 | −40.4 |
| SEQ ID No:50 | AS-II-909-20 | CAGAATATCGACGCAAAAGA | 48.2 | −36.5 |
| SEQ ID No:51 | AS-II-933-20 | GGCATCAGTCCTCGTTTCTT | 50.8 | −37.7 |
| SEQ ID No:52 | AS-II-981-20 | TGTAAACCCTCATCTCTGCT | 46.2 | −35.0 |
| SEQ ID No:53 | AS-II-1001-20 | TCAGGCAAGCAAAATCACAG | 51.3 | −37.2 |
| SEQ ID No:54 | AS-II-1006-20 | GAACATCAGGCAAGCAAAAT | 49.4 | −37.1 |
| SEQ ID No:55 | AS-II-1023-20 | TTGTGTACCAGGTGTTTGAA | 45.9 | −33.9 |
| SEQ ID No:56 | AS-II-1040-20 | CTCTCTCCTCCGATGGTTTG | 51.1 | −37.7 |
| SEQ ID No:57 | AS-II-1048-20 | TTCTCTTACTCTCTCCTCCG | 45.2 | −35.0 |
| SEQ ID No:58 | AS-II-1144-20 | GTATTGCTTCATTAGAGTGC | 41.6 | −33.0 |
| SEQ ID No:59 | AS-II-1182-20 | CCCAGTTCCAGCATAAGTCT | 48.4 | −36.5 |
| SEQ ID No:60 | AS-II-1197-20 | AAAACCTTGCTAAAACCCAG | 48.3 | −37.8 |
| SEQ ID No:61 | AS-II-1217-20 | CAAATGGGTTCTCTACTCTG | 43.7 | −33.8 |
| SEQ ID No:62 | AS-II-1224-20 | ATAAAGTCAAATGGGTTCTC | 42.6 | −34.0 |
| SEQ ID No:63 | AS-II-1254-20 | TTAGTCTTTCCTTCCAGTGA | 43.8 | −33.9 |
| SEQ ID No:64 | AS-II-1278-20 | TCGCCTACTCTCTTCTCAAA | 46.8 | −35.6 |
| SEQ ID No:65 | AS-II-1288-20 | CCTCTGATACTCGCCTACTC | 45.6 | −35.1 |
| SEQ ID No:66 | AS-II-1302-20 | GACATCACTCCCATCCTCTG | 48.7 | −35.3 |
| SEQ ID No:67 | AS-II-1335-20 | GCATCCAAGGTAAAAGAATT | 45.6 | −36.1 |
| SEQ ID No:68 | AS-II-1338-20 | TCAGCATCCAAGGTAAAAGA | 47.4 | −35.9 |
| SEQ ID No:69 | AS-II-1342-20 | GAAGTCAGCATCCAAGGTAA | 46.7 | −35.3 |
| SEQ ID No:70 | AS-II-1345-20 | TTAGAAGTCAGCATCCAAGG | 47.0 | −35.6 |
| SEQ ID No:71 | AS-II-1362-20 | GCACATCTTCAGTTCATTTA | 42.4 | −32.8 |
| SEQ ID No:72 | AS-II-1364-20 | GGGCACATCTTCAGTTCATT | 48.9 | −36.2 |
| SEQ ID No:73 | AS-II-1381-20 | AAAAATCAGCCAAGTAAGGG | 48.1 | −38.0 |
| SEQ ID No:74 | AS-II-1390-20 | ATGGAAAAAAAAAATCAGCC | 48.1 | −38.0 |
| SEQ ID No:75 | AS-II-1438-20 | TTCATGGTGTGGCTAGTTGG | 50.8 | −36.8 |
| SEQ ID No:76 | AS-II-1499-20 | AGGACTGGTTGTGAGGTAGC | 48.1 | −35.7 |

TABLE 1-continued

ANTISENSE SEQUENCES DESIGNED TO TARGET THE R2 MESSAGE

| SEQ ID No: | Name | Sequence 5' - 3' | Tm (° C.) | dG Kcal/mol |
|---|---|---|---|---|
| SEQ ID No:77 | AS-II-1517-20 | CCAGCACTATAAACAGACAG | 42.2 | −32.8 |
| SEQ ID No:78 | AS-II-1538-20 | TTCTGGCAAAAGGTGATACT | 46.5 | −35.6 |
| SEQ ID No:79 | AS-II-1560-20 | GTAAGTCACAGCCAGCCAGG | 52.2 | −37.8 |
| SEQ ID No:80 | AS-II-1581-20 | ACTGCCATTGTCACTGCTAT | 47.0 | −34.9 |
| SEQ ID No:81 | AS-II-1659-20 | TGGCTGTGCTGGTTAAAGGA | 53.2 | −38.7 |
| SEQ ID No:82 | AS-II-1666-20 | TTTTAACTGGCTGTGCTGGT | 50.0 | −37.2 |
| SEQ ID No:83 | AS-II-1700-20 | ATTAAAATCTGCGTTGAAGC | 46.8 | −36.6 |
| SEQ ID No:84 | AS-II-1768-20 | TATCGCCGCCGTGAGTACAA | 56.5 | −40.9 |
| SEQ ID No:85 | AS-II-1773-20 | GCTATTATCGCCGCCGTGAG | 57.1 | −42.6 |
| SEQ ID No:86 | AS-II-1775-12 | ATCGCCGCCGTG | 42.9 | −29.5 |
| SEQ ID No:87 | AS-II-1790-20 | GAAACCAAATAAATCAAGCT | 43.4 | −34.9 |
| SEQ ID No:88 | AS-II-1819-20 | TTAGTGGTCAGGAGAATGTA | 41.7 | −32.5 |
| SEQ ID No:89 | AS-II-1976-20 | TGGCACCAACTGACTAATAT | 44.5 | −34.2 |
| SEQ ID No:90 | AS-II-1989-20 | CCTGTCTTCTATCTGGCACC | 48.6 | −36.2 |
| SEQ ID No:91 | AS-II-2009-20 | GCCACAGGATAAAAACACAA | 47.7 | −35.9 |
| SEQ ID No:92 | AS-II-2026-20 | CCCAGGACACTACACAAGCC | 51.8 | −37.5 |
| SEQ ID No:93 | AS-II-2044-20 | TCAGAGGGGGCAGAGAATCC | 55.4 | −40.2 |
| SEQ ID No:94 | AS-II-2067-20 | TCCTTTATCCCACAACACTC | 46.3 | −35.0 |
| SEQ ID No:95 | AS-II-2083-20 | CCTTGCCCTGAGAGATTCCT | 52.3 | −39.0 |
| SEQ ID No:96 | AS-II-2083-20 | CsCTsTGsCCsCTsGAsGAsGAsTTsCCsT | 52.3 | −39.0 |
| SEQ ID No:97 | AS-II-2128-20 | GGCCCAGATCACCCCTAAAT | 54.3 | −40.9 |
| SEQ ID No:98 | AS-II-2151-20 | AAACGGCTTCTCACACATAT | 46.3 | −35.4 |
| SEQ ID No:99 | AS-II-2164-20 | GAGAAATAAAATGAAACGGC | 46.2 | −36.6 |
| SEQ ID No:100 | AS-II-2182-20 | CGTTGAGGAAAATACAGTGA | 45.1 | −34.3 |
| SEQ ID No:101 | AS-II-2229A-20 | GCTCCCACATATGAAAACTC | 46.1 | −35.2 |
| SEQ ID No:102 | AS-II-2372-20 | CACACAACCTACTTACACCA | 42.7 | −32.3 |

Footnotes for Table 1
Name includes the following:
AS = antisense;
II = R2
The first number indicates the first nucleotide position in the R2 mRNA sequence.
The second number indicates the length of the sequence segment.
The sequence AS-II-2229A shown in the Table and the sequence AS-II-2229B described in the text are alternate sequences, with 2229A chosen from the version of R2 in GENBANK (submitted by Pavloff) and 2229B chosen from the version published by Pavloff et al. 1992.
Sequences were fully thioated unless partial thioation is indicated(s)
TM° C. = melting temperature of oligonucleotide duplex formed.
dG = free energy values of oligonucleotide-complement dimer formation
In addition to the above analysis, estimates of potential dimer formation (D) potential self-complementary interactions (H) and the potential to bind to sequences in the R2 message other than the target sequences (B) were obtained. Analysis and estimates described above were obtained by using the computer modelling program OLIGO Primer Analysis Software, Version 3.4 (distributed by National Biosciences). The program allows the determination of Tm° C. and dG values, and also provides a qualitative estimation of The D, H and B parameters indicating "no potential", "some potential, or essentially "complete potential". In choosing the oligonucleotide sequences we gave high priority to sequences that exhibited high Tm° C. and dG values, which are important for tight binding of antisense molecules to their complementary strands, and high priority to antisense sequences that had estimates of no potential in D, H and B. Of the three categories (D, H, B) the most important ones were D and H, since B (i.e., binding to other regions of the R2 mRNA in addition to the precise target sequence) may enhance rather than compromise oligonucleotide activity. Most of the sequences shown in Table 1 had no potential in the D and H categories, some sequences exhibited "some potential" in D or H and were later found in tumor cell growth inhibition studies to be effective (Table 13) and therefore were also included in Table 1. We found that this approach to choosing antisense oligonucleotide inhibitors was extremely effective, since the vast majority of the chosen sequence exhibited anti-tumor properties as shown in Table 13.

TABLE 2

ANTISENSE SEQUENCES DESIGNED TO TARGET THE R1 MESSAGE

| SEQ ID No: | Name | Sequence 5' - 3' | Tm (° C.) | dG Kcal/mol |
|---|---|---|---|---|
| SEQ ID No:104 | AS-I-35-20 | GTT CCA GCC AGA CAG CAC TT | 51.7 | −37.3 |
| SEQ ID No:105 | AS-I-37-20 | GAG TTC CAG CCA GAC AGC AC | 52.0 | −37.0 |
| SEQ ID No:106 | AS-I-85-20 | CAG AGT GGG AAG GGT TAG GT | 49.7 | −37.5 |
| SEQ ID No:107 | AS-I-91-20 | AGG TGA CAG AGT GGG AAG GG | 52.7 | −38.2 |
| SEQ ID No:108 | AS-I-129-20 | GAC TGG ACT GCG GCT CTA AA | 52.1 | −38.3 |
| SEQ ID No:109 | AS-I-203-20 | ATG ACT CGT TCT TGG CGG CC | 58.6 | −42.4 |
| SEQ ID No:110 | AS-I-239-20 | CAA AGC TTC TGG ATT CGA GA | 49.6 | −37.1 |
| SEQ ID No:111 | AS-I-287-20 | TTC ATG GTG ATC TGA GCA GG | 50.6 | −36.2 |
| SEQ ID No:112 | AS-I-300-20 | GCC TTG GAT TAC TTT CAT GG | 48.9 | −37.3 |
| SEQ ID No:113 | AS-I-348-20 | TTC AGC AGC CAA AGT ATC TA | 45.4 | −34.9 |

TABLE 2-continued

ANTISENSE SEQUENCES DESIGNED TO TARGET THE R1 MESSAGE

| SEQ ID No: | Name | Sequence 5' - 3' | Tm (° C.) | dG Kcal/mol |
|---|---|---|---|---|
| SEQ ID No:114 | AS-I-395-20 | GCC AGG ATA GCA TAG TCA GG | 48.9 | −36.9 |
| SEQ ID No:115 | AS-I-439-20 | CTT TCT TTG TTT CTT TGT GC | 44.5 | −34.6 |
| SEQ ID No:116 | AS-I-504-20 | GGG AGA GTG TTT GCC ATT AT | 48.2 | −36.7 |
| SEQ ID No:117 | AS-I-520-20 | TTG ACT TGG CCA CCA TGG GA | 58.2 | −40.8 |
| SEQ ID No:118 | AS-I-540-20 | GGC CAG AAC AAT ATC CAA TG | 49.5 | −37.2 |
| SEQ ID No:119 | AS-I-556-20 | TCA GGC GAT CTT TAT TGG CC | 54.2 | −40.5 |
| SEQ ID No:120 | AS-I-635-20 | TTC AAC AAA TAA GAC CGC TC | 47.2 | −36.1 |
| SEQ ID No:121 | AS-I-658-20 | TTT CAG CCA CTT TTC CAT TG | 50.3 | −37.5 |
| SEQ ID No:122 | AS-I-662-20 | GGT CTT TCA GCC ACT TTT CC | 50.4 | −37.9 |
| SEQ ID No:123 | AS-I-782-20 | TTG AAG AGA GTG GGC GAA GC | 54.4 | −39.6 |
| SEQ ID No:124 | AS-I-786-20 | AGC ATT GAA GAG AGT GGG CG | 54.3 | −39.5 |
| SEQ ID No:125 | AS-I-809-20 | GAA AGT TGC GGG CGG TTG GT | 60.6 | −44.3 |
| SEQ ID No:126 | AS-I-843-20 | GCT GTC ATC TTT CAT ACT CA | 41.9 | −32.2 |
| SEQ ID No:127 | AS-I-908-20 | CCA ATT CCT CCA GCA GAC TT | 50.8 | −37.8 |
| SEQ ID No:128 | AS-I-923-20 | CAA CTC ACA GCA ACA CCA AT | 48.1 | −34.8 |
| SEQ ID No:129 | AS-I-932-20 | GCC CGA ATA CAA CTC ACA GC | 52.2 | −38.2 |
| SEQ ID No:130 | AS-I-967-20 | AAT TGC CAT TAG TCC CAG CA | 52.2 | −38.8 |
| SEQ ID No:131 | AS-I-1051-20 | ATG CCC CAG GAC GCT TGT TC | 58.5 | −42.2 |
| SEQ ID No:132 | AS-I-1074-20 | CCA AGG CTC CAG GTA AAT AG | 48.4 | −37.6 |
| SEQ ID No:133 | AS-I-1134-20 | ACG CTG CTC TTC CTT TCC TG | 53.7 | −39.6 |
| SEQ ID No:134 | AS-I-1162-20 | TCC AAA GAG CAA AGA AAA GA | 47.0 | −36.1 |
| SEQ ID No:135 | AS-I-1258-20 | CCT CTC CCC AAA CCT CAT CC | 54.7 | −40.2 |
| SEQ ID No:136 | AS-I-1311-20 | AAC TTT GCG GAC ACG ACC TT | 53.7 | −39.5 |
| SEQ ID No:137 | AS-I-1370-20 | GGG GTG CCT GTT TCC GTC TG | 58.9 | −42.0 |
| SEQ ID No:138 | AS-I-1418-20 | TTC TGC TGG TTG CTC TTT CG | 53.1 | −38.7 |
| SEQ ID No:139 | AS-I-1421-20 | AGG TTC TGC TGG TTG CTC TT | 50.6 | −37.6 |
| SEQ ID No:140 | AS-I-1513-20 | GGG CCA GGG AAG CCA AAT TA | 57.6 | −43.4 |
| SEQ ID No:141 | AS-I-1662-20 | GGG GCG ATG GCG TTT ATT TG | 58.8 | −44.0 |
| SEQ ID No:142 | AS-I-1666-20 | CAA TGG GCG GAT GGC GTT TA | 60.1 | −44.0 |
| SEQ ID No:143 | AS-I-1785-20 | TTC CAG AGC ACC ATA ATA AA | 45.1 | −35.1 |
| SEQ ID No:144 | AS-I-1818-20 | TGG GCC CTG CTC CTT GGC AA | 64.3 | −45.7 |
| SEQ ID No:145 | AS-I-1970-20 | GGC ATC GGG GCA ATA AGT AA | 54.1 | −41.0 |
| SEQ ID No:146 | AS-I-1976-20 | GCT GTA GGC ATC GGG GCA AT | 58.5 | −42.9 |
| SEQ ID No:147 | AS-I-2119-20 | CAT GCC ATA GGC CCC GCT CG | 64.0 | −46.4 |
| SEQ ID No:148 | AS-I-2198-20 | AGT TGC TTC AGG TCA TCA GG | 49.0 | −36.0 |
| SEQ ID No:149 | AS-I-2251-20 | CAG CTG CCA TCT TGA GAA CA | 51.1 | −36.6 |
| SEQ ID No:150 | AS-I-2304-20 | CTC AGC AAT GTG GAT GTT CA | 48.9 | −35.0 |
| SEQ ID No:151 | AS-I-2364-20 | AGT CTT CAA ACC CTG CTT CC | 50.0 | −37.6 |
| SEQ ID No:152 | AS-I-2370-20 | CAT CCC AGT CTT CAA ACC CT | 50.4 | −37.5 |
| SEQ ID No:153 | AS-I-2414-20 | GTG AAC TGG ATT GGA TTAGC | 46.1 | −35.2 |
| SEQ ID No:154 | AS-I-2491-20 | TGG CTG CTG TGT TCC TCT CC | 55.0 | −38.8 |
| SEQ ID No:155 | AS-I-2556-20 | CTT CCA AGT CTT TCC TCA GG | 48.0 | −36.4 |
| SEQ ID No:156 | AS-I-2629-20 | TAC CAC CTC AAG CAA ACC CA | 52.9 | −38.4 |
| SEQ ID No:157 | AS-I-2650-20 | CAA CAG GGT CCA GCA AAG CC | 56.8 | −40.9 |
| SEQ ID No:158 | AS-I-2769-20 | TCC GTT TTT TTT TTC TTT TT | 46.2 | −37.5 |
| SEQ ID No:159 | AS-I-2863-20 | TGC TAA ATG GGT GAT GAA AC | 47.5 | −35.8 |
| SEQ ID No:160 | AS-I-2922-20 | CCC ACC AGT CAA AGC AGT AA | 50.2 | −36.9 |
| SEQ ID No:161 | AS-I-2594-20 | CTC AAG AAG TAG TTT GGC TA-3' | 41.6 | −33.2 |

Footnotes for Table 2
Name includes the following:
AS = antisense;
I = R1
The first number indicates the first nucleotide position in the R1 mRNA sequence.
The second number indicates the length of the sequence segment.
TM ° C. = melting temperature of oligonucleotide duplex formed.
dG = free energy values of oligonucleotide-complement dimer formation
In addition to the above analysis, estimates of potential dimer formation (D) potential self-complementary interactions (H) and the potential to bind to sequences in the R1 message other than the target sequences (B) were obtained. Analysis were performed as described in the Footnote to Table 1 and criteria used to select the sequences shown in Table 2 were as indicated in the Footnote to Table 1.

TABLE 3

Antisense oligonucleotides having a sequence complementary to the human ribonucleotide reductase R1 gene

| SEQ ID No: | Name | Sequence 5' - 3' | Tm (° C.) | dG (kcal/mol) |
|---|---|---|---|---|
| 165 | AS-I-3-20 | AGG CGC AAC AAT CCA AAT CC | 65.7 | −41.5 |
| 166 | AS-I-19-20 | ACT TTC TTC AGA GCA GAG GC | 57.1 | −36.1 |
| 167 | AS-I-55-20 | GCT CAG GGG AAA GAA CTG GA | 62.5 | −39.1 |
| 168 | AS-I-73-20 | GGT TAG GTT CCA GGC GTT GC | 65.4 | −41.4 |
| 169 | AS-I-158-20 | GCT AGT GGC TGA GGC TCT GA | 61.2 | −37.9 |
| 170 | AS-I-329-20 | AGT TCC ACT GTG GTG ACC CC | 62.3 | −37.9 |
| 171 | AS-I-378-20 | AGG GTG CTT AGT AGT CAA GG | 54.7 | −35.5 |
| 172 | AS-I-420-20 | CAA GTT AGA GAC AGC GAT CC | 55.6 | −35.3 |
| 173 | AS-I-492-20 | GCC ATT ATG TGG ATT TAT GT | 53.5 | ÷34.8 |
| 174 | AS-I-578-20 | CGG TCA TAG ATA ATA GCA GA | 51.4 | −33.9 |
| 175 | AS-I-603-20 | GCC GAA GTA ATT GTA AGA GA | 53.5 | −35.0 |
| 176 | AS-I-618-20 | CTC TAG CGT CTT AAA GCC GA | 59.0 | −38.3 |
| 177 | AS-I-720-20 | TGC TGC ATC AAT GTC TTC TT | 57.1 | −35.3 |
| 178 | AS-I-758-20 | GTA AAC CAC CTC TCA GAA AG | 52.1 | −33.7 |
| 179 | AS-I-808-20 | AAA GTT GCG GGC GGT TGG TA | 63.8 | −40.2 |
| 180 | AS-I-863-20 | GTG TCA TAA ATG CCT TCA AT | 53.3 | −34.3 |
| 181 | AS-I-941-20 | CTG CCA GTA GCC CGA ATA CA | 62.2 | −39.2 |
| 182 | AS-I-996-20 | TAC TCT CAG CAT CGG TAC AA | 54.6 | −34.4 |
| 183 | AS-I-1057-20 | TAG CAA ATG CCC CAG GAC GC | 69.0 | −43.4 |
| 184 | AS-I-1083-20 | GTC TAA ATG CCA AGG CTC CA | 61.2 | −38.7 |
| 185 | AS-I-1135-20 | CAC GCT GCT CTT CCT TTC CT | 63.0 | −39.6 |
| 186 | AS-I-1235-20 | CCA GGA CAC TCA TTT GGA CA | 59.3 | −36.0 |
| 187 | AS-I-1298-20 | CGA CCT TGT TTC TCA TAA CT | 52.7 | −34.1 |
| 188 | AS-I-1319-20 | GCT TTT ACA ACT TTG CGG AC | 59.0 | −37.8 |
| 189 | AS-I-1351-20 | GAG ACT CAA TGA TGG CAT AC | 52.8 | −33.4 |
| 190 | AS-I-1441-20 | TGC TGC ATT TGA TGG TTC CC | 64.8 | −39.8 |
| 191 | AS-I-1483-20 | CCT CAT CTT TGC TGG TGT AC | 56.0 | −35.1 |
| 192 | AS-I-1570-20 | TGA CTT CAG CCA ACT TCT TA | 54.1 | −34.3 |
| 193 | AS-I-1599-20 | TTT ATT CAA GTT TCG GAC AA | 54.6 | −35.3 |
| 194 | AS-I-1636-20 | ATG CCT CTG GTA CAG GAT AG | 55.0 | −35.3 |
| 195 | AS-I-1661-20 | GGG CGA TGG CGT TTA TTT GA | 66.7 | −42.6 |
| 196 | AS-I-1685-20 | AGA CCT TGT ACC CCA ATT CC | 58.9 | −37.8 |
| 197 | AS-I-1704-20 | CAG GAT AAA AGC ATC TGC CA | 59.7 | −37.7 |
| 198 | AS-I-1721-20 | TCA AAA GGG TAT CTC ATC AG | 53.1 | −34.1 |
| 199 | AS-I-1839-20 | AGA GCC CTC ATA GGT TTC GT | 59.1 | −38.0 |
| 200 | AS-I-1840-20 | GAG AGC CCT CAT AGG TTT CG | 59.9 | −38.3 |
| 201 | AS-I-1900-20 | CCC ATA GGT CTG TAG GAG TA | 52.4 | −34.2 |
| 202 | AS-I-2004-20 | ATT ATT CCC CAG GAT CTG AG | 56.6 | −36.7 |
| 203 | AS-I-2034-20 | GAT GTT GCT GGT GTA AGG TT | 55.7 | −35.1 |
| 204 | AS-I-2060-20 | TCT CCT GAC AAG ACT CTG CG | 59.0 | −36.0 |
| 205 | AS-I-2220-20 | GAT TTC CCA CAC AGT TTT AT | 52.5 | −34.1 |
| 206 | AS-I-2324-20 | GTG AGT TTG CCA TAG TTA GG | 53.3 | −34.5 |
| 207 | AS-I-2358-20 | CAA ACC CTG CTT CCA GCC GT | 68.1 | −42.6 |
| 208 | AS-I-2390-20 | GGT CTC GTC CTT AAA TAA TA | 50.3 | −34.0 |
| 209 | AS-I-2584-20 | AGT TTG GCT ACT GAA GAC AT | 52.1 | −33.6 |
| 210 | AS-I-2669-20 | CAA TTA CTC CTT TTG CCT GC | 58.8 | −37.8 |
| 211 | AS-I-2831-20 | TCC CTG TAT GCA AGA TGA CT | 55.8 | −35.0 |
| 212 | AS-I-2924-20 | CCC ACC AGT CAA AGC AGT AA | 59.3 | −37.0 |
| 213 | AS-I-2986-20 | CCA GAT AAA GGT CCT ATC AG | 52.4 | −34.4 |

In Table 3 the "Tm" is the melting temperature of an oligonucleotide duplex calculated according to the nearest-neighbour thermodynamic values. At this temperature 50% of nucleic acid molecules are in duplex and 50% are denatured. The "dG" is the free energy of the oligonucleotide, which is a measurement of an oligonucleotide duplex stability. Computer modeling program OLIGO Primer Analysis Software, Version 5.0 was used.

The term "alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, and the like.

The term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "halo" or "halogen" refers to fluoro, chloro, bromo and iodo and preferably is either fluoro or chloro.

The term "thiol" refers to the group —SH.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically acceptable salt" refers to salts which retain the biological effectiveness and properties of the antisense oligonucleotides of this invention and which are not biologically or otherwise undesirable. In many cases, the antisense oligonucleotides of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethylamine, diethylamine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "ribonucleotide reductase gene" refers to any gene whose product, either alone or as part of a complex, is capable of catalyzing the reduction of ribonucleotides to deoxyribonucleotides.

The term "complementary to" means that the antisense oligonucleotide sequence is capable of binding to the target sequence, ie the ribonucleotide reductase mRNA or gene. Preferably the antisense oligonucleotide sequence has at least about 75% identity with the target sequence, preferably at least about 90% identity and most preferably at least about 95% identity with the target sequence allowing for gaps or mismatches of several bases. Identity can be determined, for example, by using the BLASTN program of the University of Wisconsin Computer Group (GCG) software. Preferably the antisense oligonucleotide sequence hybridizes to the ribonucleotide reductase mRNA with a melting temperature of at least 40° C., more preferably at least about 50° C. and most preferably at least about 53° C. as determined by either version 3.4 or 5.0 of the OLIGO program described herein.

The term "inhibiting growth" means a reduction in the growth of at least one tumor cell type by at least 10%, more preferably of at least 50% and most preferably of at least 75%. The reduction in growth can be determined for tumor cells by measuring the size of the tumor in mice or the inability of the tumor cells to form colonies in vitro.

The term "mammal" or "mammalian" means all mammals including humans, ovines, bovines, equines, swine, canines, felines and mice, etc.

A "mammal suspected of having a tumor" means that the mammal may have a proliferative disorder or tumor or has been diagnosed with a proliferative disorder or tumor or has been previously diagnosed with a proliferative disorder or tumor, the tumor has been surgically removed and the mammal is suspected of harboring some residual tumor cells.

Preparation of the Antisense Oligonucleotides

The antisense oligonucleotides of the present invention may be prepared by conventional and well-known techniques. For example, the oligonucleotides may be prepared using solid-phase synthesis and in particular using commercially available equipment such as the equipment available from Applied Biosystems Canada Inc., Mississauga, Canada. The oligonucleotides may also be prepared by enzymatic digestion of the naturally occurring ribonucleotide reductase R1 or R2 gene by methods known in the art.

Isolation and Purification of the Antisense Oligonucleotides

Isolation and purification of the antisense oligonucleotides described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. However, other equivalent separation or isolation procedures could, of course, also be used.

An expression vector comprising the antisense oligonucleotide sequence may be constructed having regard to the sequence of the oligonucleotide and using procedures known in the art.

Vectors can be constructed by those skilled in the art to contain all the expression elements required to achieve the desired transcription of the antisense oligonucleotide sequences. Therefore, the invention provides vectors comprising a transcription control sequence operatively linked to a sequence which encodes an antisense oligonucleotide. Suitable transcription and translation elements may be derived from a variety of sources, including bacterial, fungal, viral, mammalian or insect genes. Selection of appropriate elements is dependent on the host cell chosen.

Reporter genes may be included in the vector. Suitable reporter genes include β-galactosidase (e.g. lacZ), chloramphenicol, acetyl-transferase, firefly luciferase, or an immunoglobulin or portion thereof. Transcription of the antisense oligonucleotide may be monitored by monitoring for the expression of the reporter gene.

The vectors can be introduced into cells or tissues by any one of a variety of known methods within the art. Such methods can be found generally described in Sambrook et al.; Ausubel et al.; Chang et al. 1995; Vega et al.; and Vectors: A Survey of Molecular Cloning Vectors and Their Uses and include, for example, stable or transient transfection, lipofection, electroporation and infection with recombinant viral vectors.

Host cells suitable for carrying out the present invention include, but are not limited to, CHO, COS, BHK, 293 and HeLa. Protocols for the transfection of mammalian cells are well known in the art and include calcium phosphate mediated electroporation, and retroviral and protoplast fusion-mediated transfection.

Introduction of nucleic acids by infection offers several advantages. Higher efficiency and specificity for tissue type can be obtained. Viruses typically infect and propagate in specific cell types. Thus, the virus' specificity may be used to target the vector to specific cell types in vivo or within a tissue or mixed culture of cells. Viral vectors can also be modified with specific receptors or ligands to alter target specificity through receptor mediated events.

The oligonucleotide of the invention may be insolubilized. For example, the oligonucleotide may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk etc. The carrier may in the shape of, for example, a tube, test plate, beads disc, sphere etc.

The insoubilized oligonucleotide may be prepared by reacting the material with the suitable insoluble carrier using known chemical or physical methods, for example, cyanogen bromide coupling.

It is contemplated that the oligonucleotide of this invention may be a ribozyme which cleaves the mRNA. The ribozyme preferably has a sequence homologous to a sequence of an oligonucleotide of the invention and the necessary catalytic center for cleaving the mRNA. For example, a homologous ribozyme sequence may be selected which destroys the ribonucleotide reductase mRNA. The ribozyme type utilized in the present invention may be selected from types known in the art. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan 1994, U.S. Pat. No. 5,225,347). Hammerhead and hairpin ribozyme motifs are most commonly adapted for trans cleavage of mRNAs for gene therapy (Sullivan 1994). Hairpin ribozymes are preferably used in the present invention. In general, the ribozyme is from 30 to 100 nucleotides in length.

Pharmaceutical Formulations

When employed as pharmaceuticals, the antisense oligonucleotides are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. The pharmaceutical composition is, for example, administered intravenously. It is contemplated that the pharmaceutical composition may be administered directly into the tumor to be treated.

This invention also includes pharmaceutical compositions which contain, as the active ingredient, one or more of the antisense oligonucleotides associated with pharmaceutically acceptable carriers or excipients. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 1.5 mg to about 3 g, more usually about 10 mg to about 3.0 g, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The antisense oligonucleotide is effective over a wide dosage range and is generally administered in a pharmaceutically effective amount. An effective amount is that amount which when administered alleviates the symptoms. Preferably the effective amount is that amount able to inhibit tumor cell growth. Preferably the effective amount is from about 0.02 mg/kg body weight to about 20 mg/kg body weight. It will be understood, however, that the amount of the antisense oligonucleotide actually administered will be determined by a physician, in the light of the relevant circumstances, including the condition to be treated, the chosen route of administration, the actual compound administered, the age, weight, and response of the individual patient, the severity of the patient's symptoms, and the like. The course of therapy may last from several days to several months or until diminution of the disease is achieved.

For preparing solid compositions such as tablets, the principal active ingredient/antisense oligonucleotide is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

Another preferred formulation employed in the methods of the present invention employs transdermal delivery devices ("patches"). Such transdermal patches may be used to provide continuous or discontinuous infusion of the antisense oligonucleotides of the present invention in controlled amounts. The construction and use of transdermal patches for the delivery of pharmaceutical agents is well known in the art. See, for example, U.S. Pat. 5,023,252, herein incorporated by reference. Such patches may be constructed for continuous, pulsatile, or on demand delivery of pharmaceutical agents.

Another preferred method of delivery involves "shotgun" delivery of the naked antisense oligonucleotides across the dermal layer. The delivery of "naked" antisense oligonucleotides is well known in the art. See, for example, Felgner et al., U.S. Pat. No. 5,580,859. It is contemplated that the antisense oligonucleotides may be packaged in a lipid vesicle before "shotgun" delivery of the antisense oligonucleotide.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone | |
| (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A formulation may be prepared as follows:

| Ingredient | Quantity |
| --- | --- |
| Active Ingredient | 5.0 mg |
| Corn Oil | 1.0 mL |

FORMULATION EXAMPLE 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Other suitable formulations for use in the present invention can be found in *Remington's Pharmaceutical Sciences*.

The antisense oligonucleotides or the pharmaceutical composition comprising the antisense oligonucleotides may be packaged into convenient kits providing the necessary materials packaged into suitable containers.

The oligonucleotides and ribozymes of the invention modulate tumor cell growth. Therefore methods are provided for interfering or inhibiting tumor cell growth in a mammal comprising contacting the tumor or tumor cells with an antisense oligonucleotide of the present invention.

The term "contact" refers to the addition of an oligonucleotide, ribozyme, etc. to a cell suspension or tissue sample or to administering the oligonucleotides etc. directly or indirectly to cells or tissues within an animal.

The methods may be used to treat proliferative disorders including various forms of cancer such a leukemias, lymphomas (Hodgkins and non-Hodgkins), sarcomas, melanomas, adenomas, carcinomas of solid tissue, hypoxic tumors, squamous cell carcinomas of the mouth, throat, larynx and lung, genitourinary cancers such as cervical and bladder cancer, hematopoietic cancers, colon cancer, breast cancer, pancreatic cancer, renal cancer, brain cancer, skin cancer, liver cancer, head and neck cancers, and nervous system cancers, as well as benign lesions such as papillomas. Other proliferative disorders such as psoriasis and those involving arthrosclerosis, angiogenesis and viral infections are also included.

The oligonucleotides of the invention may also be used to treat drug resistant tumors. Examples of drug resistant tumors are tumors resistant to such chemotherapeutic agents as 5-fluorouracil, mitomycin C, methotrexate or hydroxyurea and tumors expressing high levels of P-glycoprotein which is known to confer resistance to multiple anticancer drugs such as colchicine, vinblastine and doxorubicin; or tumors expressing multi-drug resistance protein as described by Dreeley et al. Accordingly, it is contemplated that the oligonucleotides of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate and hydroxyurea. It is contemplated that the amount of chemotherapeutic agent may be either an effective amount, i.e. an amount sufficient to inhibit tumor growth or a less than effective amount.

It is contemplated that the oligonucleotides of the present invention may also be used in conjunction with other anti-tumorigenic treatments, for example radiation therapy to increase the effectiveness of the radiation therapy.

The oligonucleotides of the present invention have been found to reduce the growth of tumors that are metastatic such as MDA-MB-231 breast adenocarcinoma, HT-29 colon adenocarcinoma, H460 lung carcinoma, and A2058 melanoma cancer cells. In an embodiment of the invention, a method is provided for reducing the growth of metastastic tumors in a mammal comprising administering an amount of an oligonucleotide complementary to the ribonucleotide reductase mRNA, or an oligonucleotide shown in Tables 1,2, and 3.

The oligonucleotides may be delivered using viral or non-viral vectors. Sequences may be incorporated into cassettes or constructs such that an oligonucleotide of the invention is expressed in a cell. Preferably, the construct contains the proper transcriptional control region to allow the oligonucleotide to be transcribed in the cell.

Therefore, the invention provides vectors comprising a transcription control sequence operatively linked to a sequence which encodes an oligonucleotide of the invention. The present invention further provides host cells, selected from suitable eucaryotic and procaryotic cells, which are transformed with these vectors.

Suitable vectors are known and preferably contain all of the expression elements necessary to achieve the desired transcription of the sequences. Phagemids are a specific example of such beneficial vectors because they can be used either as plasmids or as bacteriophage vectors. Examples of the vectors include viruses such as bacteriophages, baculoviruses, retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into the cells by stable or transient transfection, lipofection, electroporation and infection with recombinant viral vectors.

Additional features can be added to the vector to ensure its safety and/or enhance its therapeutic efficacy. Such features include, for example, markers that can be used to negatively select against cells infected with recombinant viruses. An example of such a negative selection marker is the TK gene which confers sensitivity to the antiviral gancyclovir. Features that limit expression to particular cell types can also be included. Such features include, for example, promoter and regulatory elements that are specific for the desired cell type.

Retroviral vectors are another example of vectors useful for the in vivo introduction of a desired nucleic acid because they offer advantages such as lateral infection and targeting specificity. Lateral infection is the process by which a single infected cell produces many progeny virions that infect neighboring cells. The result is that a large area becomes rapidly infected.

A vector to be used in the methods of the invention may be selected depending on the desired cell type to be targeted. For example, if breast cancer is to be treated, then a vector specific for epithelial cells may be used. Similarly, if cells of the hematopoietic system are to be treated, then a viral vector that is specific for blood cells is preferred.

Utility

The antisense oligonucleotides of the present invention may be used for a variety of purposes. They may be used to inhibit the expression of the ribonucleotide reductase gene in a mammalian cell, resulting in the inhibition of growth of that cell. The oligonucleotides may be used as hybridization probes to detect the presence of the ribonucleotide reductase mRNA in mammalian cells. When so used the oligonucleotides may be labeled with a suitable detectable group (such as a radioisotope, a ligand, another member of a specific binding pair, for example, biotin). Finally, the oligonucleotides may be used as molecular weight markers.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:

$\mu$M=micromolar
mM=millimolar
M=molar
ml=milliliter
$\mu$l=microliter
mg=milligram
$\mu$g=microgram
PAGE=polyacrylamide gel electrophoresis
rpm=revolutions per minute
$\Delta$G=free energy, a measurement of oligonucleotide duplex stability
kcal=kilocalories
FBS=fetal bovine serum
DTT=dithiothrietol
SDS=sodium dodecyl sulfate
PBS=phosphate buffered saline
PMSF=phenylmethylsulfonyl fluoride
General Methods Standard molecular biology techniques known in the art and not specifically described were generally followed as in Sambrook et al., (1989, 1992); in Ausubel et al., (1989); and in Perbal, (1988). Polymerase chain reaction (PCR) was carried out generally as in *PCR Protocols: A Guide To Methods And Applications,* Academic Press, San Diego, Calif. (1990).

General Methods in Immunology

Standard methods in immunology known in the art and not specifically described were generally followed as in Stites et al.(eds), Basic and Clinical Immunology (8th Edition), Appleton & Lange, Norwalk, Conn. (1994) and Mishell and Shugi (eds), Selected Methods in Cellular Immunology, W. H. Freeman and Co., New York (1980).

Assays for Tumorigenicity and Metastasis

Malignancy potential was determined as reported previously [Wright, 1989a; Egan et al., 1987a, 1987b; Damen et al., 1989; Taylor et al., 1992; Stokoe et al., 1994). Six to eight week old C3H/HeN syngeneic mice (Charles River, Quebec) were used to evaluate tumorigenic and metastatic potential of the cells. Cells were prepared from subconfluent, logarithmically growing cultures, collected by gentle treatment with trypsin/EDTA solution and adjusted to appropriate concentration in a balanced salt solution.

For the tumorigenicity (tumor latency) assay, $1 \times 10^5$ cells in a 0.1 ml volume were injected subcutaneously into the back of mice and the time required to form a tumor ($2 \times 2$ mm) detectable by palpation was recorded. The growth of tumors was also evaluated by measuring tumor diameters, and estimating tumor base area each day following tumor appearance [Damen et al., 1989]. Tumor size was determined by multiplying the dimensions of the cross-section of the tumor. Tumors were removed from the mice and tumor weight was recorded 21 days later. In the case of no tumor formation, mice were kept for 2 months after injection and then sacrificed.

For experimental metastasis assays (determination of metastatic potential), $1 \times 10^5$ cells in a 0.2 ml volume were injected into the tail veins of 6–8 week old C3H/HeN syngeneic mice and an estimate of the number of lung tumors was made 21 days later. The mice were sacrificed, and the lungs were stained by injecting Bouin's solution (picric acid, formaldehyde, acetic acid (15:5:1)1 intratracheally [Egan et al., 1987b; Damen et al., 1989]. Pulmonary tumors were counted with the aid of a dissecting microscope. To confirm that equal numbers of test and control cells were injected, duplicate culture plates containing growth medium were inoculated with approximately 100 cells per plate. After 10 days in culture, plates were stained with methylene blue and colonies were scored.

Ribonucleotide Reductase Assay

Ribonucleotide reductase activity in crude extracts prepared from cells is assayed as previously described [Lewis et al., 1978; Hurta and Wright, 1992; Hurta and Wright 1995A]. Enzyme preparations are obtained from logarithmically growing cells lysed in phosphate buffered saline, pH 7.2, containing 1 mM dithiothreitol and 1 mM protease inhibitor, AEBSF (Calbiochem, San Francisco, Calif.), by three cycles of freeze-thawing. Following centrifugation, the supernatant is used for enzyme activity assays with [$^{14}$C]-CDP (Moravek Biomedical, Brea, Calif.), as detailed previously [Lewis et al., 1978; Hurta and Wright 1992; Fan et al., 1996A; Choy et al., 1988].

Western Blot Analysis

The procedures used have been reported [Fan et al., 1996a; 1996b; Choy et al., 1988]. Briefly, following cell extract preparation, total protein content was determined, and an aliquot was analyzed on 10% linear SDS-polyacrylamide gel. After protein transfer and blocking, membranes were incubated with anti-R2 rabbit polyclonal antibody [Fan et al., 1996A]. Alkaline phosphatase conjugated goat anti-rabbit IgG (Sigma) was used for protein R2 detection.

Oligonucleotides

The antisense oligonucleotides were selected from the sequence complementary to the ribonucleotide reductase mRNA such that the sequence exhibits the least likelihood of showing duplex formation, hairpin formation, and homooligomers/sequence repeats but has a high potential to bind to the ribonucleotide reductase mRNA sequence. In addition, a false priming to other frequently occurring or repetitive sequences in human and mouse was eliminated. These properties were determined using the computer modeling program OLIGO® Primer Analysis Software, Version 3.4 or 5.0 (International Biosciences, Inc. Plymouth Minn.). The oligonucleotide sequences were fully thioated when synthesized unless partial thioation is indicated Table 1 and 2 by (s).

Cell Lines

The different human cancer cell lines including lung carcinoma (H460), ovary adenocarcinoma (SK-OV-3), hepatocellular carcinoma (Hep G2), breast adenocarcinoma (MDA-MB-231), metastatic pancreatic adenocarcinoma (AsPC-1), colon adenocarcinoma (HT-29), human melanoma cell line (A2058), human brain carcinoma (U87) cells were obtained from American Type Culture Collection (ATCC). The cell lines were maintained in α-MEM medium (Gibco BRL, Gaithersburg, Md.) supplemented with 10% fetal bovine serum (FBS).

Example 1

R2 Cooperates with Activated Oncogenes

To determine the malignant potential of deregulated expression of the rate-limiting R2 component of ribonucleotide reductase, the properties of cells stably infected with a retroviral expression vector (SH/mR2) carrying the mouse R2 component (Fan et al., 1996b), were investigated. Further the interaction between R2 and activated oncogenes was explored.

Expression Vectors

The retroviral expression vector for the human Myc epitope-tagged mouse R2 component, SH/mR2, was constructed and packaged as described in Fan et al. [1996b]. The infectivity of the viral stock was $>1 \times 10^4$ colony-forming units/ml. Plasmid pHO6Ti which expresses T-24 H-ras and a selective marker neo was used for malignant transformation [Egan et al., 1987a, 1987b; Taylor et al., 1992]. The activated Rac-1 plasmid (V12 Rac-1) was kindly provided by M. Symons [Stokoe et al., 1994].

Cells and Cell Culture

The mouse cell lines, BALB/c 3T3, NIH 3T3, four lines of T24 H-ras transformed 10T½ cells, named C1, NR4, r-2 and r-3 have been previously used as recipients of the R2 retroviral vector [Fan et al., 1996b]. Cells were routinely cultured in α-minimal essential medium (α-MEM)(Gibco, Grand Island, N.Y.) supplemented with 10% calf serum (Fetalclone III, Hyclone, Logan, Utah). Infection of cells with SH/mR2 or control virus LXSH in the presence of polybrene was carried out [Miller et al., 1993], and stable infectants ($>1 \times 10^4$ clones) were obtained with hygromycin selection and pooled [Fan et al., 1996b; Miller et al., 1993]. Determinations of cell division times, plating efficiencies, and relative sensitivities to hydroxyurea cytotoxicity by estimating relative colony forming efficiencies, were carried out as previously described [Lewis et al., 1978; Egan et al., 1987a; Hards and Wright, 1981].

Growth in soft agar was estimated in 10 cm tissue culture plates containing 15 ml base agar (0.5% Bacto-agar in α-MEM plus 10% calf serum) and 10 ml of growth agar (0.33% agar in α-MEM containing 10% calf serum). Cells were obtained from subconfluent cultures, and colonies were scored 10–15 days later [Egan et al., 1987a, 1987Hards and Wright, 1981]. Transformation was also analyzed by determining focus formation after cells were infected with SH/mR2 or LXSH or transfected with T-24 Ras or V12 Rac-1 plasmids by calcium phosphate precipitation [Taylor et al., 1992]. At 40 hours after infection or transfection, cells were split into three 10 cm tissue culture plates which were provided daily with 20 ml of fresh complete medium (α-MEM plus 10% calf serum) for 10–14 days, stained with methylene blue and foci were scored [Taylor et al., 1992]. The transfection frequency in all the experiments were routinely determined by cotransfection of a mammalian expression plasmid for β-galactosidase from *Esherichia coli*, with the T-24 Ras or V-12 Rac-1 plasmids, followed by treatment of cells with the X-gal and counting the number of blue cells [Price et al., 1987]. In some cases, T-24 Ras plasmid transfected plates were selected with geneticin, and drug resistant colonies were scored approximately 14 later after staining with methylene blue.

Assays for Tumorigenicity and Metastasis

Malignant potential was determined as described herein above.

Protein R2 Analysis

The procedures for Western blot analysis have been described previously, for example, using either the anti-myc mouse monoclonal 9E10 antibody (ATCC, Rockville, Md.) [Fan et al., 1996b] or the anti-R2 rabbit polyclonal antibody [Chan et al., 1993]. To determine recombinant R2 protein expression during the cell cycle, flow cytometry analysis was performed following 9E10/fluorescein isothiocyanate antibody labelling as previously described [Blosmanis et al. 1987; Chadee et al., 1995].

Determination of Membrane-associated Raf-1 Protein

The membrane fraction was prepared as described by Qui et al. [1995], and used for Western analysis with a polyclonal antibody specific for Raf-1 protein (Santa Cruz Biotechnology Inc., Santa Cruz, Calif.), after the protein content was determined by the standard Bio-Rad assay. Densitometry analysis of the Raf-1 band was performed, and the amount of Raf-1 protein from each sample was corrected by densitometry analysis of a well separated band on a parallel gel stained with Coomassie blue.

Ribonucleotide Reductase Assay

The assay was performed as described herein above. In some experiments enzyme assays were performed by combining purified recombinant R1 protein [Salem et al., 1993] with 9E10 antibody-precipitated R2 protein [Hurta and Wright, 1992]. In this Example, 20 μg of the 9E10 antibody and 50 μl of Staphylococcal protein A-agarose (Sigma Chem. Co., St. Louis, Mo.) were added to 1 ml of the supernatant of centrifuged lysed cells, and placed on a rocker at 4° C. for 2 hours. The Staphylococcal protein A agarose-irnmunocomplex was washed three times with 1 ml of cold phosphate buffer containing 1 mg/ml bovine serum albumin. The immunocomplex was then assayed for ribonucleotide reductase activity [Lewis et al., 1978; Hurta and Wright, 1992; Fan et al., 1996b; Choy et al., 1988].

Assay of MAPK Activity

Cultures with>90% confluency were stressed in serum-free medium [Stokoe et al., 1994; Jelinek et al., 1994] and extracted as previously described [Alessi et al., 1995]. MAPK-2 protein was immunoprecipitated by agarose beads conjugated with non-neutralizing antibody for the protein (Santa Cruz Biotechnology, Inc.), and the kinase activity of the immunocomplex was assayed by measuring its ability to phosphorylate myelin basic protein using a MAPK assay kit from Upstate Biotechnology, Inc. (Lake Placid, N.Y.).

Results

Expression of Biologically Active R2 Protein

Figure 1B:
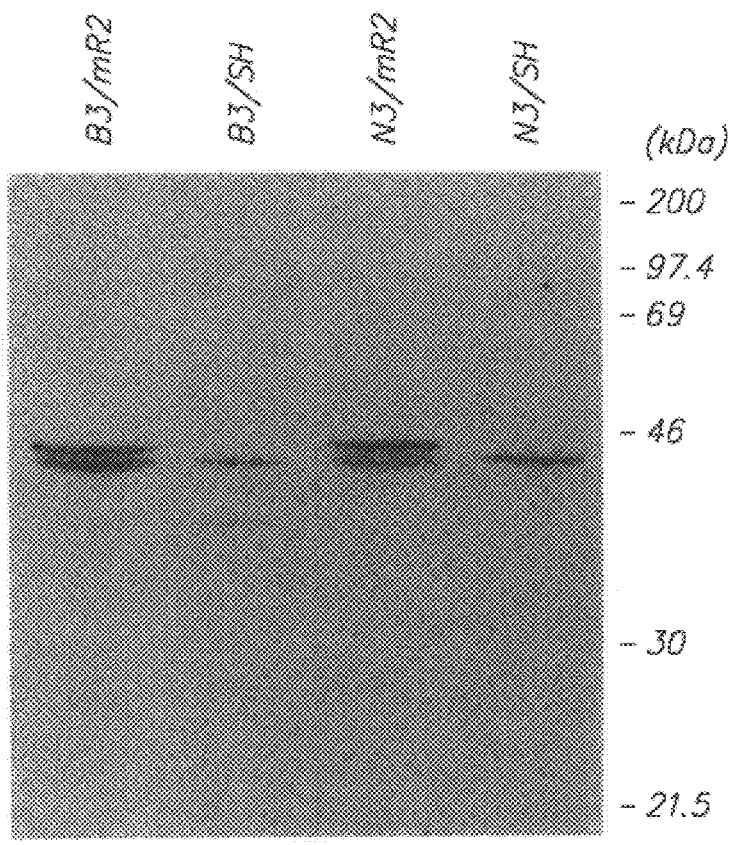

To determine the malignant potential of deregulated expression of the rate-limiting R2 component of ribonucleotide reductase, the properties of cells stably infected with a retroviral expression vector (SH/mR2) carrying the mouse R2 component [Fan et al., 1996b], were investigated. The use of this expression vector allowed high infection efficiency and stable expression of the R2 protein. To distinguish the vector gene product from the endogenous R2, a human c-Myc epitope coding for 10 amino acids plus methionine was added to the 5'-end of the R2 cDNA. FIG. 1A shows that Western blots with the 9E10 antibody that specifically recognizes the Myc-epitope sequence detects the R2 protein of approximately 45 kDa in SH/mR2 stably infected BALB/c 3T3 and NIH 3T3 cells (named B3/mR2 and N3/mR2, respectively), but not in control vector (LXSH) infected B3/SH or N3/SH cells. R2 specific antibodies detected the endogenous as well as the recombinant R2 protein in expression vector infected cells, and as expected only the endogenous protein was observed in control vector infected cells (FIG. 1B).

Figure 1C:
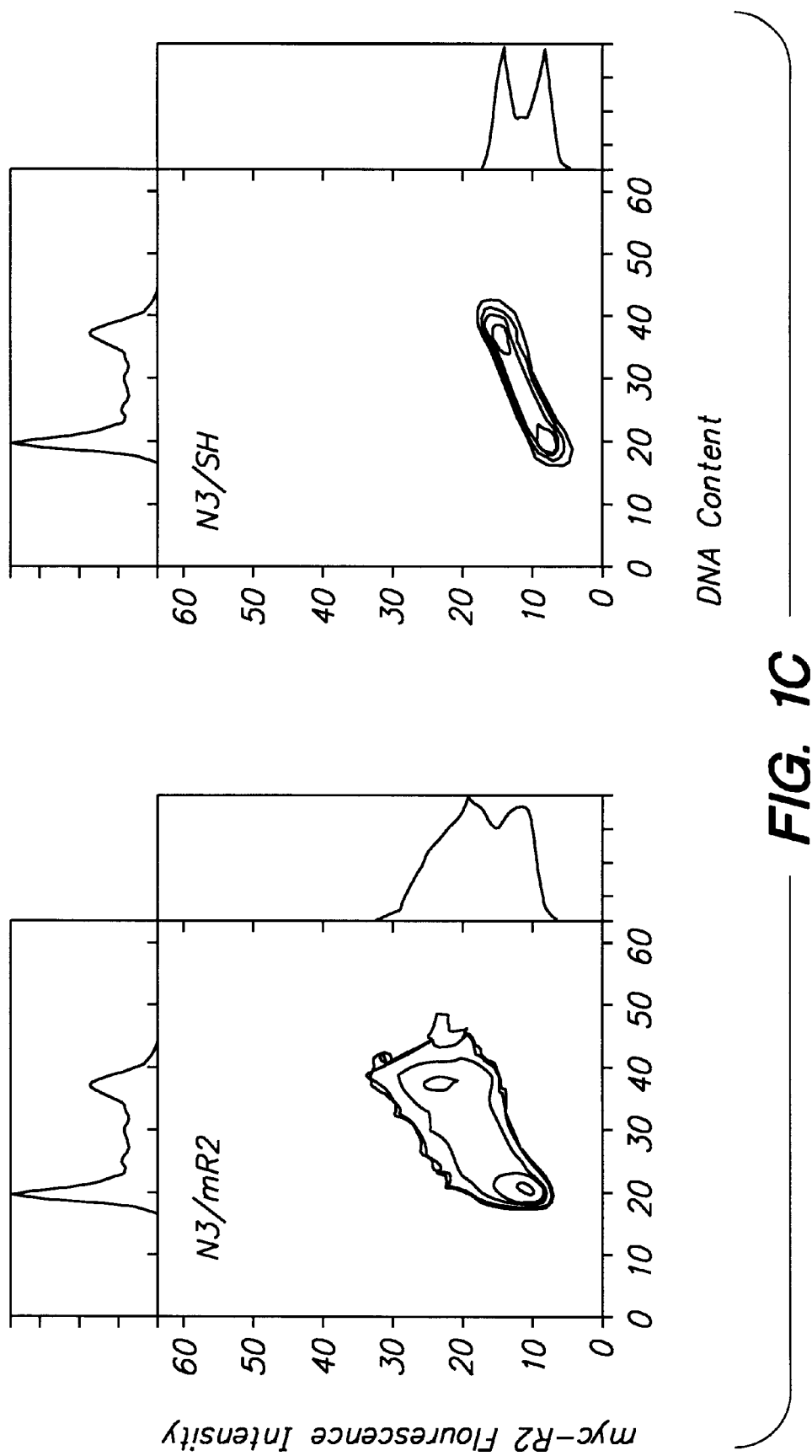

Flow cytometry analysis following 9E10/fluorescein isothiocyanate antibody labelling demonstrated that the recombinant R2 protein was constitutively expressed throughout the cell cycle (FIG. 1C). Indirect microscopic analysis using the 9E10 antibody indicated that essentially every cell in the B3/mR2 and N3/mR2 populations expressed the Myc-epitope tagged R2 protein.

Several experiments were performed to demonstrate that the vector-expressed R2 is biologically active. First, B3/mR2 and N3/mR2 cells were observed to be resistant in colony-forming experiments to the cytotoxic effects of hydroxyurea, an inhibitor of the R2 protein [Wright, 1989A; Wright et al., 1989B], when compared to B3/SH and N3/SH cells [Fan et al., 1996b]. Second, ribonucleotide reductase activity was assayed and found that the CDP reductase activities in B3/mR2 and N3/mR2 cells in three independent experiments were 1.96±0.32 and 1.71±0.11 nmoles/mg protein/hour, respectively, which was 2.6 and 2.1 times higher than observed with B3/SH and N3/SH cells (0.74±0.14 and 0.83±0.08 nmoles/mg/hour, respectively). Finally, enzyme assays were carried out by combining purified recombinant R1 protein [Salem et al., 1993], with 9E10 antibody precipitated R2 protein. Significant levels of activity (15 to 20 nmoles/mg/hr.) were detected when B3/mR2 and N3/mR2 cells were used as a source for Myc-epitope tagged R2, and as expected no activity was found when B3/SH or N3/SH cells were used.

Ras Transformation Potential Determined by Aberrant R2 Gene Expression

The above results indicate that cells can be altered in the regulation of biologically active R2 protein. Therefore, altered R2 expression was tested to see if it further transformed cells like BALB/c 3T3 or NIH 3T3. Similar to control B3/SH and N3/SH cells, as well as the parental non-infected lines; B3/mR2 and N3/mR2 cultures remained in a flat, non-transformed morphology on tissue culture plates, and exhibited contact and density inhibited growth. No transformed foci were observed with BALB/c 3T3 or NIH 3T3 cells after infection with the retroviral SH/mR2 vector (FIG. 2A, a and b).

Figure 2B:
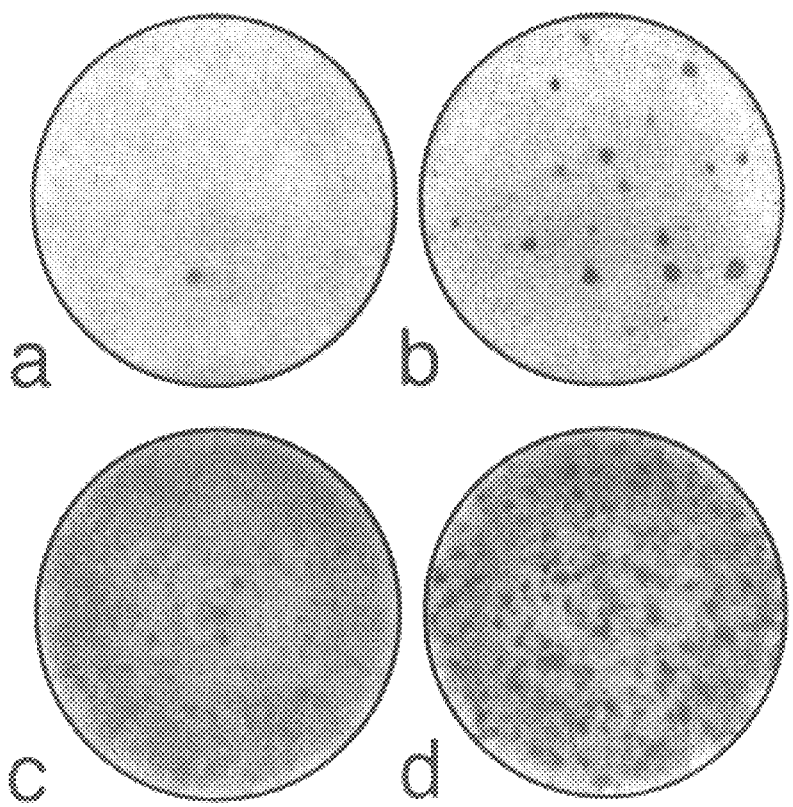
Figure 2C:
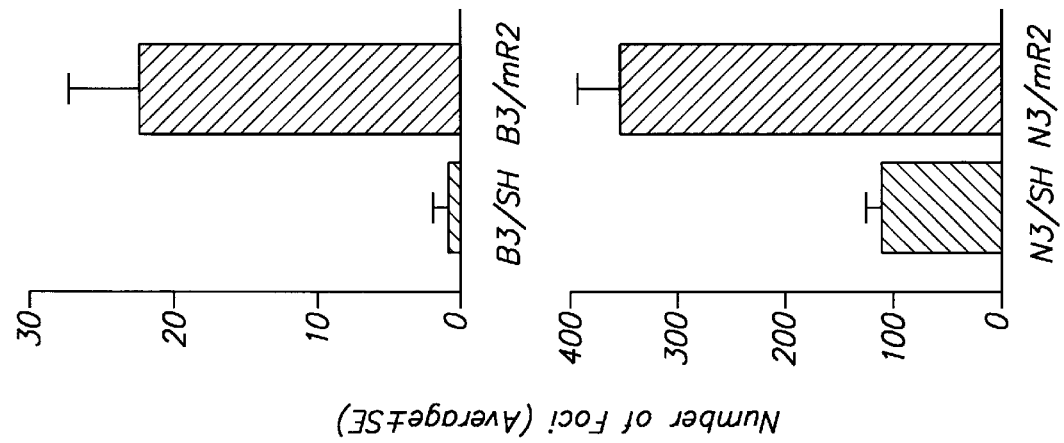

The results suggest that deregulation of R2 gene expression does not on its own transform BALB/c 3T3 or NIH 3T3 fibroblasts. To test the hypothesis that deregulated R2 expression may cooperate with oncogenes like H-ras, an expression plasmid containing T24 H-ras was transfected into established recombinant R2 expressing cell populations derived from BALB/c 3T3 or NIH 3T3. A consistent and significant increase (3.4 fold) in the number of foci formed with H-ras transfected N3/mR2 cells was observed when compared to N3/SH control cells (FIG. 2B, c and d and FIG. 2C). An even more marked increase of about 70 fold was observed when H-ras transfected B3/mR2 cells were compared to B3/SH cells (FIG. 4B, a and b and FIG. 2C). This occurred even though the transfection efficiency with N3/mR2 and B3/mR2 cells as determined by scoring G418 selected colonies, and/or counting blue cells following cotransfection of H-ras with an expression plasmid for *E. coli* β-galactosidase [Price et al., 1987], were actually lower by about 50%) than with N3/SH and B3/SH cells.

Ras Malignancy Potential Determined by Aberrant R2 Gene Expression

Since combinations of altered R2 gene expression and activated H-ras were synergistic in focus forming experiments in which ras was transfected into altered R2 expressing cells, this gene combination was tested further by infecting four independent H-ras transformed 10T½ cell lines, C1, NR4, r-2 and r-3 that were previously characterized [Egan et al., 1987a, 1987b; Taylor et al., 1992; Stokoe et al., 1994], with the retroviral vector SH/mR2. Stable infectants were selected with hygromycin, and Western blot analyses and enzyme activity assays confirmed that these infectants expressed biologically active Myc-tagged R2 protein.

Soft agar growth experiments revealed that H-ras transformed cells containing the recombinant R2 sequence were much more efficient at producing colonies in semi-solid growth agar than the uninfected parental populations (e.g. r-3) or control vector infected cells (C1, NR4, r-2) (Table 4).

TABLE 4

Increased colony formation in Soft Agar by ras-transformed cells containing the recombinant R2 vector

| Cell Line | Colonies (average ± SE) formed in soft agar with varying cell inoculum[a] | | |
|---|---|---|---|
| | $10^3$ | $10^4$ | $10^5$ |
| C1/SH | 0 | 4 ± 3 | 66 ± 9 |
| C1/mR2 | 3 ± 3 | 28 ± 7 | 347 ± 45 |
| r-2/SH | ND | 9 ± 2 | 105 ± 7 |
| r-2/mR2 | ND | 24 ± 1 | 298 ± 11 |
| NR4/SH | 0 | 3 ± 1 | 32 ± 4 |
| NR4/mR2 | 2 ± 1 | 14 ± 2 | 127 ± 10 |
| r-3 | 7 ± 1 | 100 ± 11 | ND |
| r-3/mR2 | 31 ± 4 | 309 ± 17 | ND |

Figure 3A:
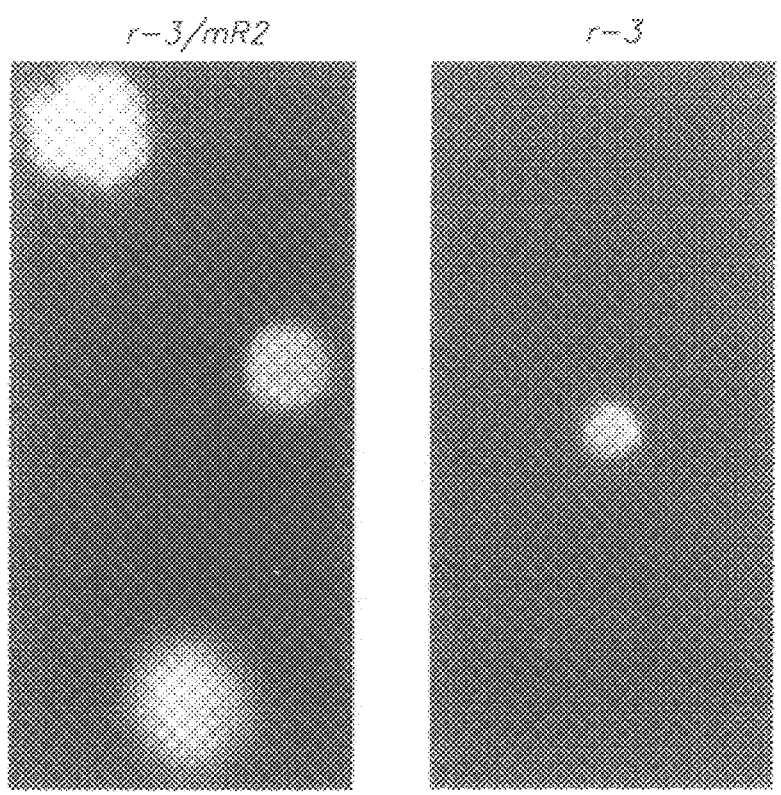

[a]The number of colonies presented were the results obtained in three independent experiments, except those obtained for r-2/SH and r-2/mR2 cells which were the results from single experiments with triplicate dishes. ND = not determined In addition, many of the colonies formed by cells infected with recombinant R2 were larger in size (FIG. 3A). Since each pair of recombinant a expressing and control cell populations have almost identical growth rates (12.9 hours for C1/SH and 12.2 hours for C1/mR2, 13.5 hours for r-2/SH and 13.9 hours for r-2/mR2, 11.6 hours for r-3 and 11.9 hours for r-3/mR2, 14.1 hours for NR4/SH and 14.3 hours for NR4/mR2), plating efficiencies (58% for C1/SH and 55% for C1/mR2, 59% for r-2/SH and 63% for r-2/mR2, 91% for r-3 and 88% for r-3/mR2, 73% for NR4/SH and 75% for NR4/mR2), and cell cycle phase distributions (data not shown) when grown on solid surfaces, the alterations observed in soft agar and in foci forming experiments suggest that a combination of deregulated R2 expression and activated H-ras may lead to greater malignant potential in vivo.

Therefore, the tumorigenic and metastatic potential of C1/mR2 and C1/SH cells was compared in syngeneic C3H/HeN mice. Marked differences in malignant potential were observed. C1/mR2 cells exhibited shorter tumor latency and greater tumor growth when compared to C1/SH cells (FIG. 3B). Furthermore, metastasis assays clearly indicated that C1/mR2 cells were more malignant than C1/SH cells and produced significantly more lung tumors (FIG. 3C).

R2 Gene Expression and Oncogene Cooperativity

The above results indicate that altered R2 expression can cooperate with activated H-ras in in vitro transformation and in in vivo malignancy assays. Since no obvious differences in growth rates or cell cycle phase distributions were found that may account for this cooperation, as for example changes in cell cycle regulation, the following idea was tested. Does deregulated R2 expression synergize with ras by elevating the activity of a Ras signal pathway? This would be consistent with studies showing a direct correlation between ras expression and malignant potential [Egan et al., 1987a, 1987b; Wright et al., 1993; Bradley et al., 1986]. A major Ras pathway for regulating gene expression involves the Raf-1 protein kinase. Activated Ras recruits Raf to the plasma membrane where Raf and downstream signalling molecules like MAPKs become activated [Stokoe et al., 1994; Jelinek et al., 1994; Leevers et al., 1994].

Using a Raf-1 specific antibody, the levels of membrane associated Raf-1 in six BALB/c 3T3, NIH 3T3 and 10T½ derived cell lines containing deregulated R2 expression was compared with control cells containing only endogenous R2 protein (FIG. 4A). In all six cases, cell lines containing deregulated R2 showed increased membrane associated Raf-1, with an average increase of about 30% which was highly significant ($p<0.001$). In agreement with the above observation, cell lines with deregulated R2 expression exhibited a consistent and significant increase of about 70% ($p<0.001$) in MAPK-2 activity (FIG. 4B). Oncogenic Ras also activates the Rac pathway which is parallel to the Raf pathway, and therefore constitutively active Rac-1 cooperates with membrane-targeted Raf-1 in malignant transformation [Qiu et al., 1995].

If MAPK activation mediated by Raf-1 translocation and activation is important in the R2/ras synergism described herein above in this Example, then aberrant R2 expression should cooperate with activated Rac-1 in cellular transformation, because it has been shown previously that activated Raf-1 and Rac-1 cooperate in mechanisms of transformation [Qiu et al., 1995]. FIG. 4C shows that this prediction is correct, since positive cooperation in transformation between activated Rac-1 and R2 was observed in a manner similar to Ras and R2, as measured by focus formation with N3/mR2 and N3/SH cells transfected with activated V12 Rac-1 [Qiu et al., 1995]. These observations are consistent with the view that deregulated R2 gene expression cooperates with oncogenes like ras and rac by upregulating Raf translocation and MAPK pathway activity, but they do not rule out the possibility that other transduction pathways involving activated Raf may also be involved, since there is evidence that Raf can regulate some cellular activities through MAPK-independent pathway(s) [Lenormand et al., 1996; Koong et al., 1994; Agarwal et al., 1995].

This Example indicates for the first time that the R2 component of mammalian ribonucleotide reductase is a novel malignancy determinant that can synergize with activated oncogenes to modify malignant potential. It is important to note that the only role ascribed to R2 in the cell prior to this Example is as a rate-limiting component of ribonucleotide reductase. This Example demonstrates that R2 can also participate in other critical cellular functions and can play a direct role in determining malignant potential through oncogenic cooperativity.

Example 2

R2 Gene Expression and Changes in Drug Sensitivity and Genome Stability

Cell Lines and Culture Conditions

The hydroxyurea resistant mouse cell lines, H-2, H-4, LHF and SC2 were derived from mouse L cells and have been characterized in Choy et al. [1988] and McClarty et al. [1987]. BALB/c 3T3 cells were used as recipients of an R2 retroviral expression vector (B3/mR2 and B3/R2c2 cell lines), or of the same retroviral vector lacking the R2 sequence (B3/SH cells)[Fan et al., 1996a; 1996b]. NIH-3T3 cells were also used as recipients of the R2 retroviral expression vector (N/R2–4 cell line) or of this retroviral vector lacking the R2 sequence (N/SH cells), as described previously [Fan et al., 1996a; 1996b]. The N/R2+ASR2 cell line was the recipient through co-transfection using LipofectAmine (Life Technologies, N.Y) [Damen et al., 1991] of retroviral vectors containing the R2 coding sequence and the R2 sequence in the antisense orientation. RP3 and RP6 cells are 10T½ mouse cells that have been transfected with the T-24 H-ras oncogene and a mutant oncogenic form of the p53 gene [Taylor et al., 1992], and they were also used as recipients through transfection using LipofectAmine reagent, of a retroviral vector containing the R2 coding region in an antisense orientation [Fan et al., 1996b], to obtain RP3/ASR2 and RP6/ASR2 cells. 1B cells are p53-/- and were derived from embryonic fibroblasts [Lowe et al., 1994]. All cells were cultured in α-minimal essential medium (Gibco, Grand Island, N.Y.) containing 10% fetal bovine serum (Intergen, Purchase, N.Y.) and antibiotics (100 units/ml penicillin and 100 $\mu$g/ml streptomycin) at 37° C. in a humidified atmosphere containing 5% $CO_2$.

Drug Selections

Cells ranging in numbers from 500 to $1-2\times10^5$ were added to 100 mm tissue culture plates in growth medium containing 10% dialyzed fetal bovine serum, and in the absence or presence of drug [Huang et al., 1995a; Choy et al., 1988]. The culture medium was replaced with fresh medium every week for two to three weeks. Surviving cells were visualized by methylene blue staining, and colonies of about 50 cells or more were scored [Huang et al., 1995a]. The relative colony forming efficiency was defined as the ability to produce colonies in the presence of a drug divided by that ability in the absence of drug.

Assay for Gene Amplification

Genomic DNA was extracted from logarithmically growing cells by the phenol-chloroform extraction method [Blin and Stafford, 1976], and potential gene amplification events were determined by Southern blot analysis as described [Huang et al., 1995a; Choy et al., 1988], using the cDNA fragments as probes noted below. The pCAD142 plasmid containing CAD cDNA, which encodes the CAD protein complex [Shigesada et al., 1985], was used to obtain the 6.3 Kb Hind III fragment as a probe. The pLTR DHFR26 plasmid containing the mouse dihydrofolate reductase gene [Chang et al., 1978], provided the 1.3 Kb Bam H1 fragment as a probe. The 1487 bp Sal I/Pst I probe for ribonucleotide reductase R2 was prepared from cDNA clone 10 [Huang et al., 1995a; Choy et al., 1988].

Electrophoretic Gel Mobility Shift Assay (EMSA)

EMSA was used to determine the presence of wild type p53. Assays were performed essentially as described [Price and Calderwood, 1993], with the following modifications. Cells on 150 mm plates were washed once with ice cold phosphate buffered saline (PBS) and scraped into 1 ml PBS. Cells were pelleted by centrifugation at 1300 g at 4° C. for 10 minutes and stored at −80° C. Nuclei were prepared by lysing the pellets in 300 $\mu$l buffer A (20 mM HEPES {pH 7.6}, 20% glycerol, 10 mM NaCl, 1.5 mM $MgCl_2$, 0.2 mM EDTA and 0.1% Triton X-100) for 20 minutes on ice. Buffer A also contained 1 mM phenylmethylsulfonyl fluoride (PMSF) and 10 mM dithiothreitol (DTT). Nuclei were isolated by centrifugation at 1300 g at 4° C. for 10 minutes. Nuclear lysates were prepared by adding 20–40 $\mu$l of buffer A containing 500 mM NaCl, 1 mM PMSF and 10 mM DTT to the nuclear pellet and incubating 20 minutes on ice. The extracted nuclei were pelleted by centrifugation at 16,000 g at 4° C.; the supernatant was removed and an aliquot was used for protein determination using the Biorad protein assay procedure (Biorad).

The nuclear lysate was incubated with an excess of double stranded p53 consensus binding sequence (GGACATGCCCGGGCATGTCC)(SEQ ID No:162) end labeled with [$\gamma^{32}P$]-ATP using T4 polynucleotide kinase (Boehringer). DNA binding was carried out in buffer containing 20 mM HEPES (pH 7.6), 20% glycerol, 1.5 mM $MgCl_2$, 0.2 mM EDTA, 1 mM PMSF and 10 mM DTT. Each binding reaction contained 5 $\mu$g cell lysate, 10 $\mu$g double stranded poly (dI-dC)(Pharmacia), 1.4 ng labeled consensus probe and 100 ng of monoclonal antibody 421 (Santa Cruz) in a total volume of 20 $\mu$l. DNA binding was allowed to proceed for 30 minutes at room temperature and the mixture was separated by electrophoresis on 5% nondenaturing polyacrylamide gels. Electrophoresis was carried out at room temperature until the xylene cyanol tracking dye had run to the bottom of the gel and the free probe had run off the gel.

Statistical Analysis

Analysis of covariance was used to compare dose response data between groups of different cell lines, with the significance level set at α=0.05 [Huang et al., 1995a].

Results

Hydroxyurea Resistant Cell Lines with Decreased Sensitivity to Non-selective Drugs H-2, H-4, LHF and SC2 are mouse L cell lines selected for resistance to the cytotoxic effects of the antitumor agent, hydroxyurea. These four cell lines exhibited resistance to hydroxyurea in colony forming efficiency experiments, that ranged between approximately 18 (H-2) to 30 (SC2) fold higher than the wild type mouse L cell line from which they were derived [Choy et al., 1988; McClarty et al., 1988]. They also contained elevated levels of ribonucleotide reductase activity that ranged between 2.2 fold (H-2) to 17 fold (LHF and SC2), which was primarily due to increases in the R2 component of ribonucleotide reductase that is limiting for enzyme activity and cell division in proliferating mouse cells.

TABLE 5

Drug Sensitivities Determined by Relative Colony Forming Efficiencies × $10^4$

| Drug Conc. | Cell Lines | | | | |
|---|---|---|---|---|---|
| | W.T. | H2 | H4 | LHF | SC2 |
| A. PALA | | | | | |
| 20 μM | 172.3 ± 126.3 | 406.7 ± 202.2 | 322.5 ± 36.4 | 233.3 ± 3.6 | 850.1 ± 325.2 |
| 30 μM | 50.3 ± 20.5 | 39.4 ± 16.4 | 84.0 ± 30.0 | 78.8 ± 7.9 | 187.6 ± 46.4 |
| 40 μM | 15.0 ± 7.0 | 23.3 ± 10.4 | 43.3 ± 9.6 | 46.5 ± 9.9 | 37.5 ± 8.7 |
| 50 μM | 3.6 ± 1.1 | 7.9 ± 1.7 | 23.2 ± 0.5 | 25.0 ± 6.8 | 47.5 ± 35.8 |
| 60 μM | 1.3 ± 0.4 | 3.6 ± 0.6 | 11.1 ± 1.4 | 10.7 ± 3.0 | 17.6 ± 1.2 |
| B. MTX | | | | | |
| 40 nM | 11.2 ± 7.2 | 52.6 ± 25.2 | 44.2 ± 20.9 | 143.4 ± 41.3 | 880.4 ± 147.4 |
| 60 nM | 12.3 ± 7.2 | 73.7 ± 16.6 | 34.7 ± 11.2 | 63.5 ± 18.6 | 566.8 ± 66.2 |
| 80 nM | 2.2 ± 1.6 | 67.7 ± 20.0 | 39.3 ± 18.7 | 68.2 ± 19.2 | 306.6 ± 61.5 |
| 100 nM | 0.8 ± 0.4 | 75.3 ± 10.0 | 15.1 ± 8.8 | 60.8 ± 16.7 | 261.8 ± 39.7 |
| 150 nM | 0.5 ± 0.2 | 53.3 ± 9.4 | 32.3 ± 13.7 | 63.9 ± 16.0 | 301.6 ± 76.8 |

The relative colony forming efficiencies are shown ± SE, and the values presented are from 4 to 8 determinations. Statistically significant differences were observed when data obtained wtih H2 (p = 0.0004), H4 (p ≤ 0.0001), LHF (p ≤ 0.0001) and SC2 (p ≤ 0.0001) were each compared to data obtained with the parental wild type (W.T.) cell line.

Table 5 shows that the four hydroxyurea resistant cell lines were also less sensitive to the cytotoxic effects of N-(phosphonacetyl)-L-aspartate (PALA) and methotrexate (MTX) in colony forming experiments, when compared to parental wild type mouse L cells. These differences in drug sensitivity are highly significant, with p values of <0.0001 for each of the cell lines when compared to the parental wild type mouse cells.

Figure 5A:
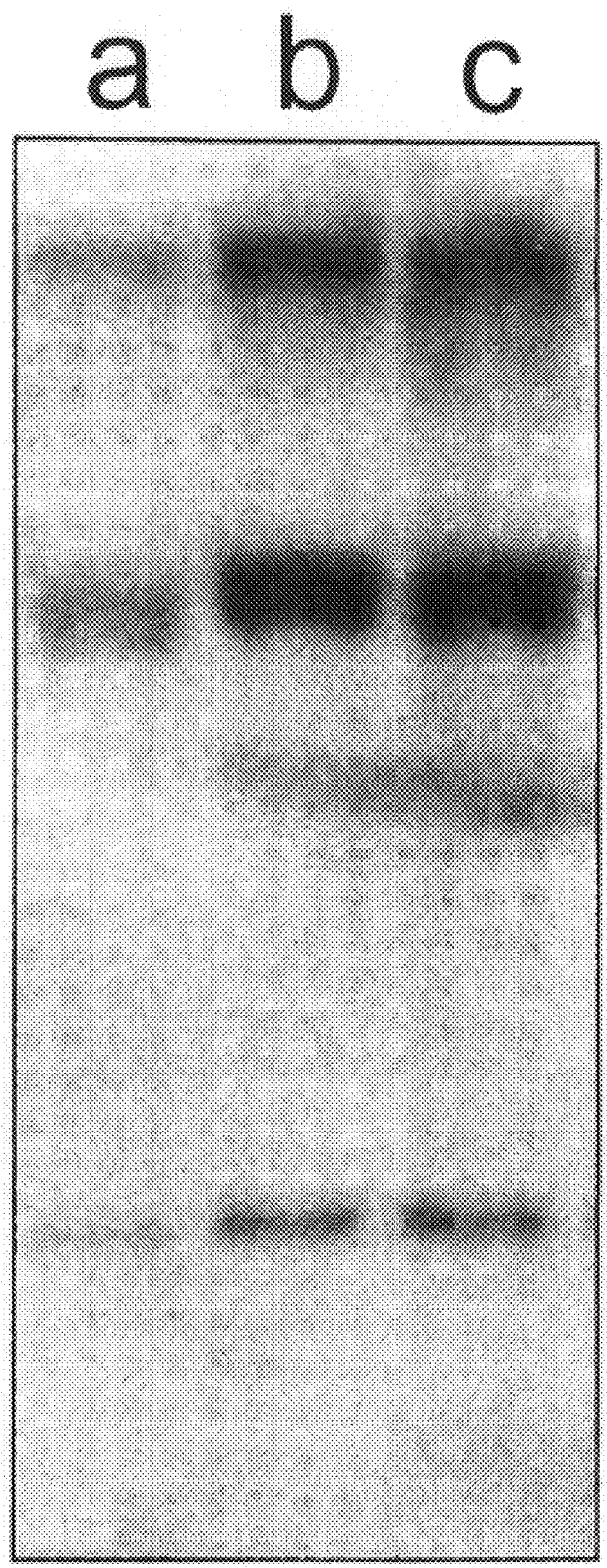
FIG. 5A–B are photographs of gels showing examples of Southern blot analysis of CAD (A) and DHFR (B) DNA with mouse L cells.
Figure 5B:
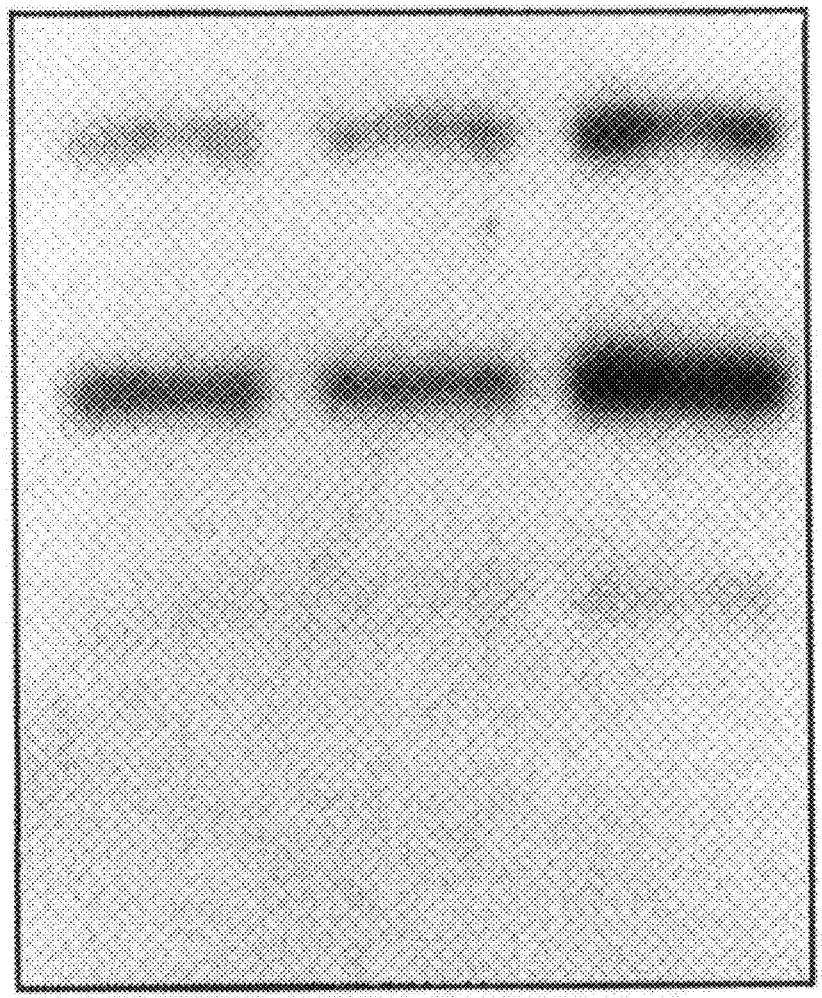

Although many mechanisms responsible for drug resistance have been described [Wright, 1989; Kohn, 1996], resistance to MTX and PALA are frequently accompanied by increased levels of the drug targeted gene products, dihydrofolate reductase (DHFR) or CAD (a multifunctional polypeptide containing carbamyl phosphate synthetase, aspartate transcarbamylase and dihydrooratase) respectively, and this often occurs through a mechanism of gene amplification [Huang et al., 1995a; Livingston et al., 1992; Yin et al., 1992; Mai, 1994; Stark, 1993]. Indeed, the principal and perhaps only mechanism for PALA resistance in mouse cells occurs via CAD gene amplification [Stark, 1993]. Therefore, colonies that developed in the presence of normally cytotoxic concentrations of these two drugs were examined for possible gene amplification events. FIG. 5 shows that cells that proliferated in the presence of PALA or MTX exhibited increased CAD or DHFR gene copy numbers. In keeping with previous studies [Stark, 1993; Huang et al., 1995b; Otto et al., 1989; Stark et al., 1990], all colonies that developed in PALA and tested (10/10) showed CAD gene amplification. Also as previously reported [Huang et al., 1995b], some but not all colonies that developed in the presence of MTX (3/6) showed DHFR gene amplification.

Direct Test for a Relationship Between R2 Gene Expression and Decreased Drug Sensitivity Since hydroxyurea resistant mouse cells contain other biochemical alterations in addition to changes in ribonucleotide reductase [Wright et al., 1989B], the relationship between drug sensitivity and increased R2 levels was directly tested with cells containing a retroviral expression vector encoding the mouse R2 sequence, and cells containing the same retroviral vector but lacking the R2 sequence. B3/mR2 is a population of BALB/c 3T3 cells containing elevated R2 protein due to the presence of a retroviral expression vector encoding R2, and B3/SH is a cell population that has wildtype levels of R2 protein and contains the empty vector as a control. B3/R2c2 is a cloned line with elevated R2 protein selected from the B3/mR2 population.

Consistent with previous reports showing that elevations in R2 gene expression leads to resistance to hydroxyurea, Table 6 shows that B3/mR2 and B3/R2c2 cells are significantly more resistant to the cytotoxic effects of hydroxyurea, at a range of concentrations, when compared to B3/SH cells. These results further demonstrate that B3/mR2 and B3/R2c2 cells express increased levels of an active R2 component of ribonucleotide reductase. B3/mR2 and B3/R2c2 cells were also significantly less sensitive to the cytotoxic effects of PALA and MTX, which act at sites other than ribonucleotide reductase (Table 6). Resistance to these two drugs ranged between approximately 10 fold with 100 nM MTX to more than 100 fold at most concentrations of PALA tested.

TABLE 6

Drug Sensitivities Determined by Relative Colony forming Efficiencies × $10^4$

| | Cell Lines | | |
|---|---|---|---|
| Drug Conc. | B3/SH | B3/mR2 | B3/R2c2 |
| A. Hydroxyurea | | | |
| 0.1 mM | 3.3 ± 1.4 | 1310 ± 319.0 | 830.8 ± 97.0 |
| 0.4 mM | 0.17 ± 0.19 | 14.6 ± 4.0 | 33.7 ± 11.0 |
| 0.5 mM | 0.21 ± 0.14 | 6.5 ± 4.6 | 26.9 ± 11.9 |
| 0.6 mM | 0.41 ± 0.22 | 5.2 ± 3.7 | 12.5 ± 4.6 |
| 0.8 mM | 0.19 ± 0.62 | 2.6 ± 1.4 | 13.2 ± 6.4 |
| B. PALA | | | |
| 10 μM | 17.9 ± 11.0 | 965.0 ± 529.7 | 1230.0 ± 97.0 |
| 20 μM | 0.39 ± 0.18 | 120.1 ± 28.4 | 55.1 ± 15.6 |
| 40 μM | 0.35 ± 0.01 | 25.0 ± 4.6 | 20.2 ± 6.8 |
| 50 μM | 0.24 ± 0.14 | 27.6 ± 8.9 | 15.9 ± 4.0 |
| 60 μM | 0.12 ± 0.05 | 25.0 ± 6.4 | 18.7 ± 5.3 |
| 80 μM | 0.17 ± 0.08 | 27.1 ± 6.75 | 20.0 ± 4.9 |
| C. MTX | | | |
| 20 nM | 192.6 ± 44.6 | 1055.0 ± 239.0 | 382.4 ± 71.3 |
| 40 nM | 15.7 ± 2.9 | 62.1 ± 8.8 | 60.8 ± 13.0 |

TABLE 6-continued

Drug Sensitivities Determined by Relative Colony forming Efficiencies x $10^4$

| | Cell Lines | | |
|---|---|---|---|
| Drug Conc. | B3/SH | B3/mR2 | B3/R2c2 |
| 60 nM | 6.1 ± 2.0 | 76.7 ± 21.6 | 64.1 ± 20.5 |
| 80 nM | 2.2 ± 0.7 | 17.5 ± 3.6 | 20.1 ± 5.5 |
| 100 nM | 1.5 ± 0.5 | 12.3 ± 2.8 | 21.0 ± 7.2 |
| 150 nM | 3.0 ± 1.1 | 23.0 ± 7.6 | 33.4 ± 14.3 |

The relative colony forming efficiencies are shown ± SE and the values presented are from 4 to 12 determinations. Statistically significant differences were observed when data obtained with B3/mR2 or with B3/R2c2 were compared with data obtained with B3/SH (all p values were ≦ 0.0001 for data obtained in the presence of hydroxyurea, PALA or MTX).

Furthermore, Southern blot analysis showed that colonies that developed in the presence of PALA or MTX contained amplifications of CAD or DHFR genes (FIG. 6), although as observed with mouse L cells (FIG. 5) and as has been reported in other studies [Hurta and Wright, 1992; Hurta et al., 1991], not all colonies that developed in MTX containing medium exhibited DHFR gene amplification. Unlike PALA resistance, MTX resistance in mouse cells can occur through a variety of mechanisms [Otto et al., 1989; Stark et al., 1990; Flintoff, 1989].

The changes in sensitivity to chemotherapeutic compounds exhibited by cells containing elevated levels of the ribonucleotide reductase R2 component were further tested using NIH-3T3 cells containing the R2 expression retroviral vector (Table 7). These cells (N/R2–4) were resistant to hydroxyurea when compared to cells containing the retroviral vector lacking the R2 coding sequence (N/SH). The N/R2–4 cells were also significantly more resistant to MTX. Although the N/R2–4 cells showed a trend towards resistance to PALA when compared to N/SH cells, this trend was not statistically significant. This latter observation suggests that other factors inherent in the genetic differences between the cell lines used in this study, in addition to the increased R2 levels, can influence drug sensitivity responses.

TABLE 7

Drug Sensitivities Determined by Relative Colony Forming Efficiencies x $10^4$

| | Cell Lines | | |
|---|---|---|---|
| Drug Conc. | N/SH | N/R2-4 | N/R2 + ASR2 |
| A. Hydroxyurea | | | |
| 0.3 mM | 1.14 ± 0.12 | 46.1 ± 9.8 | 0.49 ± 0.34 |
| 0.4 mM | 0.71 ± 0.17 | 18.0 ± 6.7 | 0.14 ± 0.14 |
| B. PALA | | | |
| 10 μM | 5.28 ± 1.5 | 6.22 ± 3.3 | 1.81 ± 0.8 |
| 15 μM | 5.83 ± 2.7 | 10.0 ± 5.5 | 0.58 ± 0.3 |
| 20 μM | 0.30 ± 0.1 | 1.71 ± 1.2 | 0.04 ± 0.04 |
| 25 μM | 0.53 ± 0.3 | 0.8 ± 0.7 | 0.04 ± 0.04 |
| 30 μM | 0.48 ± 0.08 | 1.03 ± 0.07 | 0.12 ± 0.12 |
| 40 μM | 0.27 ± 0.2 | 0.14 ± 0.08 | 0.04 ± 0.04 |
| C. MTX | | | |
| 20 nM | 655 ± 74.8 | 540 ± 25.1 | 423 ± 119 |
| 40 nM | 21 ± 12.1 | 147 ± 4.2 | 3.5 ± 1.9 |
| 60 nM | 3.4 ± 2.2 | 62.2 ± 30.7 | 1.9 ± 1.3 |
| 80 nM | 5.0 ± 5.0 | 50.4 ± 23.9 | 2.5 ± 1.5 |

TABLE 7-continued

Drug Sensitivities Determined by Relative Colony Forming Efficiencies x $10^4$

| | Cell Lines | | |
|---|---|---|---|
| Drug Conc. | N/SH | N/R2-4 | N/R2 + ASR2 |
| 100 nM | 4.2 ± 2.5 | 66.1 ± 32.8 | 1.1 ± 0.6 |
| 150 nM | 1.4 ± 0.9 | 21.0 ± 11.5 | 0, n = 4 |

The relative colony forming efficiencies are shown ± SE, and the values presented are from 4 to 6 determinations. Where 0 is shown, the number of determinations using 1 x $10^5$ cells per test is shown as 4 (n = 4). Statistically significant differences were observed when data obtained with N/SH in the presence of PALA was compared to data obtained with N/R2-4 or withN/R2 + ASR2 in the presence of hydroxyurea (p = 0.0001 in both cases) or in the presence of MTX (p = 0.0002 and 0.032, respectively). Statistically significant differences were also observed when data obtained with N/SH in the presence of PALA was compared to data obtained with N/R2 + ASR2 (p = 0.002), but not with data obtained with N/R2-4.

Figure 7:
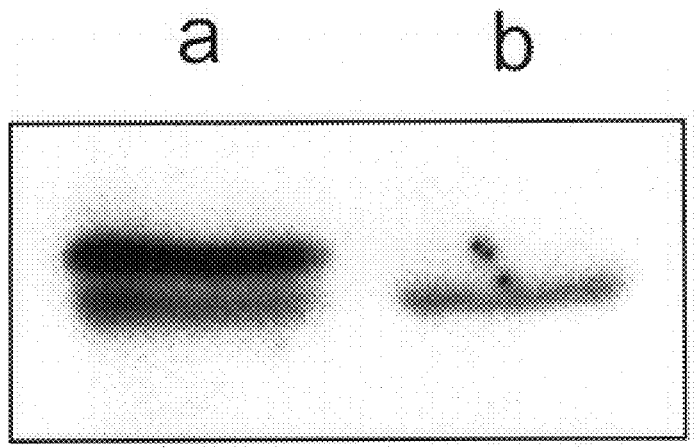
FIG. 7 is a photograph of a Western blot analysis of R2 protein levels in N/R2-4 (a) and N/R2+ASR2 (b) cells. To distinguish the vector R2 protein from the endogenous gene product in transfected cells, a human c-myc epitope coding for ten amino acids plus methionine was placed at the 5' end of the cDNA for R2. Recombinant (upper band) and endogenous (lower band) R2 protein is observed in lane a and is markedly reduced in R2 antisense containing cells (lane b). Both cell lines grew with approximately the same doubling time of about 16 hours.

Therefore, the hypothesis that R2 levels are important in determining drug sensitivity characteristics was tested by investigating drug sensitivities after decreasing the levels of R2, through expression of an R2 antisense construct introduced into N/R2–4 cells to produce the N/R2+ASR2 population. FIG. 7 shows that the level of R2 protein is markedly reduced in N/R2+ASR2 cells when compared to N/R2–4 cells. The N/R2+ASR2 cells were significantly more sensitive to hydroxyurea, PALA and MTX when compared to N/R2–4 cells (Table 7). Furthermore, sensitivity to these three drugs in the R2 antisense expressing cells was significantly increased when compared to control N/SH cells containing the empty vector (Table 7).

Mouse 10T½ cells transfected with activated ras and a mutant oncogenic form of p53 are highly resistant to chemotherapeutic agents [Huang et al., 1995b]. The observation that R2 antisense expression can increase sensitivity of NIH-3T3 cells to hydroxyurea, PALA and MTX led us to test the possibility that cells containing ras and mutated p53 may also exhibit reduced drug resistance characteristics in the presence of an R2 antisense sequence. Table 8 shows that this is correct. Cells containing the R2 antisense sequence are significantly more sensitive to hydroxyurea, PALA, and MTX when compared to cells containing the same vector but without R2 in the antisense orientation. These observations suggest that at least one of the determining factors relevant to drug sensitivity of these highly transformed and malignant cells, is ribonucleotide reductase R2 levels.

TABLE 8

Drug Sensitivities Determined by Relative Colony Forming Efficiencies x $10^4$

| | Cell Lines | | | |
|---|---|---|---|---|
| Drug Conc. | RP3/SH | RP3/ASR2 | RP6/SH | RP6/ASR2 |
| A. Hydroxyurea | | | | |
| 0.1 mM | 263.6 ± 19.3 | 109.3 ± 43 | 201.3 ± 27.2 | 43.8 ± 12.3 |
| 0.2 mM | 53.6 ± 13.7 | 22.9 ± 3.1 | 35.5 ± 8.4 | 8.6 ± 2.5 |
| 0.3 mM | 20.8 ± 7.5 | 6.6 ± 2.5 | 12.6 ± 2.4 | 4.5 ± 1.1 |
| 0.4 mM | 5.8 ± 1.9 | 1.0 ± 0.2 | 10.8 ± 4.1 | 1.2 ± 0.5 |
| 0.5 mM | 4.8 ± 1.9 | 0.2 ± 0.1 | 12.1 ± 3.9 | 1.8 ± 0.9 |
| 0.6 mM | 0.7 ± 0.3 | 0.3 ± 0.1 | 6.6 ± 2.9 | 1.5 ± 0.7 |
| 0.8 mM | 0.8 ± 0.3 | 0.1 ± 0.05 | 1.7 ± 1.2 | 0.4 ± 0.3 |

TABLE 8-continued

Drug Sensitivities Determined by Relative Colony Forming Efficiencies x $10^4$

| | Cell Lines | | | |
|---|---|---|---|---|
| Drug Conc. | RP3/SH | RP3/ASR2 | RP6/SH | RP6/ASR2 |
| B. PALA | | | | |
| 10 µM | 2569 ± 338 | 1183 ± 384 | 4619 ± 648 | 2083 ± 960 |
| 20 µM | 123.4 ± 19.3 | 86.1 ± 32.9 | 1220 ± 255 | 368 ± 154 |
| 30 µM | 45.2 ± 7.8 | 19.5 ± 4.7 | 450 ± 129 | 316 ± 171 |
| 40 µM | 15.0 ± 4.9 | 4.7 ± 0.6 | 271 ± 68 | 116 ± 54 |
| 50 µM | 9.3 ± 3.6 | 2, 1 ± 0.8 | 109 ± 23 | 41.7 ± 23 |
| 60 µM | 3.9 ± 1.6 | 0.3 ± 0.2 | 55.5 ± 13 | 13.2 ± 6.3 |
| C. MTX | | | | |
| 20 nM | 961.7 ± 134 | 485.9 ± 165 | 1856 ± 464 | 1504 ± 486 |
| 40 nM | 347.1 ± 154 | 77.8 ± 18 | 172 ± 41.3 | 91.5 ± 28.1 |
| 60 nM | 123.8 ± 64 | 18.1 ± 6.2 | 77.3 ± 15.6 | 49.9 ± 14.1 |
| 80 nM | 66.5 ± 37 | 4.4 ± 10.8 | 68.7 ± 16.7 | 36.0 ± 6.0 |
| 100 nM | 34.8 ± 21 | 0.6 ± 0.06 | 46.6 ± 5.6 | 14.4 ± 13.8 |
| 150 nM | 4.7 ± 3 | 0.2 ± 0.1 | 11.1 ± 4.4 | 3.5 ± 0.9 |

The relative colony forming efficiencies are shown ± SE, and the values presented are from 4 to 10 determinations. Statistically significant differences were observed when data obtained with RP6/SH was compared with data observed with RP6/ASR2 (p = 0.0001, 0.0001 and 0.0001 in the presence of hydroxyurea, PALA and MTX, respectively), Significant differences were also observed when data obtained with RP3/SH was compared with data obtained with RP3/ASR2(p = 0.04, 0.0001 and 0.004 in the presence of hydroxyurea, PALA and MTX, respectively)

Figure 8:
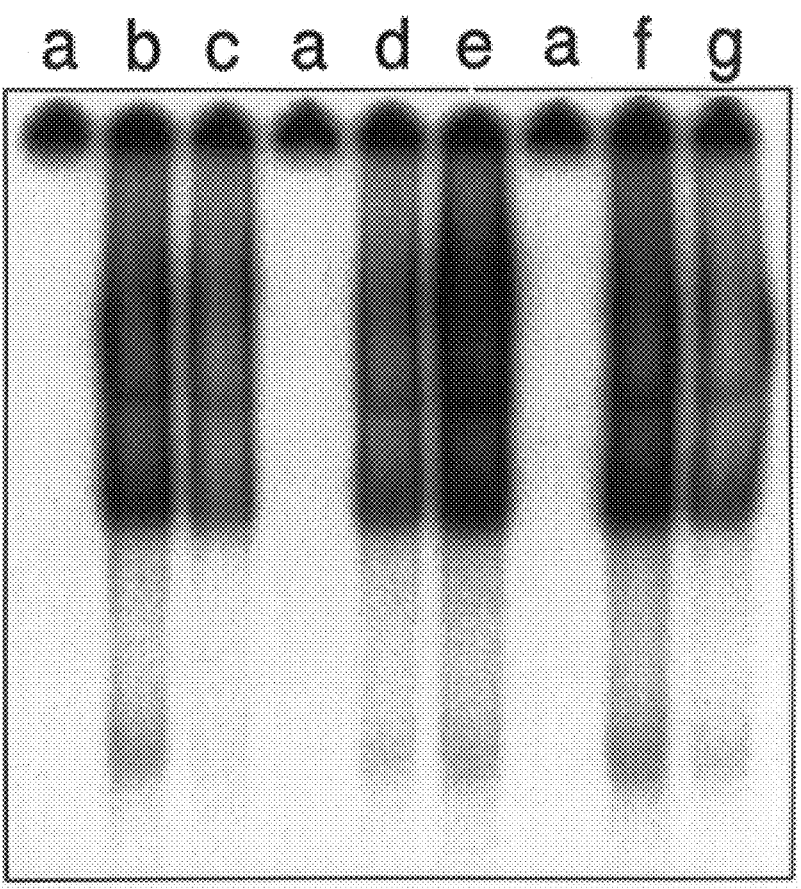
FIG. 8 is a photograph of a gel showing p53-DNA binding activity in cells from colonies that developed in the presence of PALA, MTX or hydroxyurea. (a) control 1B cells that are p53-null, (b) B3/mR2 cells that grew in the presence of 20 μM PALA, (c) B3/R2c2 cells that grew in the presence of 40 μM PALA, (d) B3/mR2 cells that grew in the presence of 40 nM MTX, (e) B3/R2c2 cells that grew in the presence of 60 nM MTX, (f) B3/mR2 cells that grew in the presence of 0.20 mM hydroxyurea, and (g) B3/R2c2 cells that grew in the presence of 0.30 mM hydroxyurea. Cells were incubated with $^{32}$P-labeled p53 consensus binding sequence in the presence of antibody 421, which activates p53 for DNA binding. Note the presence of complexes in all cell lines except in the 1B control p53-null cells. Low molecular weight complex formation results from p53-DNA binding and high molecular weight complex formation results from antibody supershifted p53-DNA binding.

Evidence that Loss of p53 Protein Function is not Required for R2-Mediated Drug Resistance and Gene Amplification Inactivation or loss of p53 is a common event associated with the development of tumors and the accompanying decrease in genetic stability observed in malignant cells, including the ability to undergo spontaneous gene amplifications [Livingston et al., 1992; Yin et al., 1992; Takenaka et al., 1995]. Therefore, we tested the possibility that the increased drug resistance properties exhibited by the R2 overproducing B3/mR2 and B3/R2c2 cells may be occurring through a mechanism that results in a loss of wild type p53 activity. It has been demonstrated that p53 is a transcription factor, and that transactivation by wild type p53 but not mutated versions of p53 is sequence-specific, and correlates with its binding to consensus DNA sequences [Takenaka et al., 1995; Kern et al., 1992]. To determine the presence or absence of wild type p53 function in drug resistant colonies that developed in the presence of PALA, MTX or hydroxyurea, cell extracts were used in electrophoretic gel mobility shift assays (EMSA) [Price and Calderwood, 1993], to test for sequence specific p53 binding activity. FIG. 8 shows that drug resistant clones derived from R2 overexpressing cells exhibited wild type p53 binding activity. These observations also agreed with our inability to detect mutant p53 proteins in cells from drug resistant colonies in immunoprecipitation assays using the Pab240 monoclonal antibody [Gannon et al., 1990], which specifically detects common forms of mutant p3.

Example 3

Antisense Deoxyribonucleotide Sequences that Target Ribonucleotide Reductase and are Cytotoxic for Human Tumor Cells.

As shown in the Examples herein above full length antisense constructs of R2 affect the tumorigenicity and/or metastatic competence of tumor cells and susceptibility to chemotherapeutic agents. Applicants therefore investigated the potential of shorter antisense constructs of R1 and R2 for their effect on tumor cells.

Colony Forming Efficiency and Treatment of Cells with Antisense Constructs

Colony forming efficiency was determined as previously reported [Huang and Wright, 1994]. The cells were cultured for 24 hours at 370° C. in growth medium with 10% fetal bovine serum. The cells were washed in 5 ml phosphate buffered saline, pH 7.2, once prior to lipofectin +/− oligonucleotide treatment.

The oligonucleotides being tested were added to cell cultures in the presence of 2.5 µg of DOTMA/DOPE (Lipofectin; Life Technologies, Inc.) for four hours. The oligonucleotide was tested at 0.2 µM unless otherwise indicated. Controls were the cultures treated with lipofectin but without the oligonucleotide. After 4 hours the medium containing the oligonucleotide was removed and washed with 5 ml of growth medium. The cells were then cultured in growth medium containing 10% fetal bovine serum for seven to ten days. Surviving cells were visualized by methylene blue staining, and colonies were scored. In some experiments cell aliquotes were removed from the culture and viability was determined using the trypan blue exclusion test [Phillips, 1973]. Results were analyzed as percent of surviving cells compared to control cells.

Results

Antisense molecules were identified that target ribonucleotide reductase. As shown below they were cytotoxic for a variety of human tumor cells. Sequences were found that facilitated drug-cytotoxicity for drug resistant tumor cells. That is, at very low non-cytotoxic concentrations, antisense sequences targeting ribonucleotide reductase can sensitize tumor cells to the cytotoxic activity of clinically important chemotherapeutic compounds.

In initial studies two antisense sequences of 20-mer, designated AS-II-336-20 and AS-II2229B-20, directed against the R2 mRNA were made and investigated. The first, AS-II-336-20, has the sequence 5'-TCC TGG AAG ATC CTC CTC GC-3'(SEQ ID No:1), and targets the R2 message of human ribonucleotide reductase at nucleotides 336–355, based on the numbering of R2 nucleotides [Pavloff et al., 1992]. The AS-II-2229B-20 sequence is: 5'-TCC CAC ATA TGA GAA AAC TC-3' (SEQ ID No:2), and targets the R2 message at nucleotides 2229–2248. Both AS-II-336-20 and AS-II-2229B-20 were constructed as phosphorothioate sequences to protect against nuclease activity [Anazodo et al., 1995].

Antisense construct AS-II-336-20 was tested for the ability to inhibit the proliferation of human tumor cells (Hela) in relative colony forming efficiency experiments as described herein above. Hela S3 cells (American Type Culture Collection, Rockville, Md., ATCC), and a Hela cell line (Hela 1 mM) previously selected for resistance to the antitumor agent, hydroxyurea [Wright et al., 1987], were tested (Table 9). Two experiments were undertaken with Hela S3 cells. With a 4 hour treatment of 0.2 µM antisense construct AS-II-336-20, inhibition of 92% and 82% was seen in colony forming efficiency in two experiments, respectively. The same experiment was repeated with the Hela 1 mM cell line and with varying concentrations of the antisense construct AS-II-336-20 (Table 9) with similar results, 0.2 µM was an effective concentration for inhibiting colony formation.

These data show that AS-II-336-20 is a very effective inhibitor of human tumor cell colony forming ability, and it is effective both in inhibiting the proliferation of human tumor cell colony forming ability and in inhibiting the proliferation of human tumor cells that exhibit resistance to another chemotherapeutic compound. Similarly, as shown in Table 9, antisense construct AS-II-336-20 is an effective antitumor compound in experiments performed with the mouse tumor cell line, SC2, which is a highly hydroxyurea resistant mouse L cell line [McClarty et al., 1988].

The antisense sequence AS-II-2229B-20 was also tested for the ability to inhibit the proliferation of human Hela tumor cells in relative colony forming efficiency experiments with results similar to that of AS-II-336-20 as shown in Table 9. These data show that AS-II-2229B-20 is a potent antitumor agent when tested with Hela S3 cells and with the drug resistant Hela 1 mM cell line.

TABLE 9

Reduced colony Forming Efficiency following Treatment with R2 Antisense Constructs

| Conc. AS-II 336-20 | % Inhibition | Conc. AS-II-2229B-20 | % Inhibition |
|---|---|---|---|
| Cell Line: HeLa S3 | | | |
| 0 | — | 0 | — |
| 0.2 µM | 92% | 0.05 µM | 50% |
| 0.2 µM | 82% | 0.10 µM | 80% |
| | | 0.20 µM | 95% |
| | | 0.20 µM | 97% |
| Cell Line: HeLa 1mM | | | |
| 0 µM | — | 0 µM | — |
| 0.01 µM | 15% | 0.01 µM | 0 |
| 0.05 µM | 25% | 0.02 µM | 0 |
| 0.10 µM | 60% | 0.03 µM | 21% |
| 0.20 µM | 85% | 0.04 µM | 34% |
| | | 0.05 µM | 48% |
| | | 0.05 µM | 50% |
| | | 0.10 µM | 78% |
| | | 0.20 µM | 97% |
| | | 0.20 µM | 90% |
| Cell Line: Mouse SC2 | | | |
| 0 | — | | |
| 0.2 µM | 95% | | |

The antisense construct AS-II-2229B-20 was also tested for the ability to inhibit the proliferation of the human breast cancer cell line MDA435 and found to be very effective (Table 10).

TABLE 10

Treatment with an R2 Antisense Construct

| Construct | Conc. (µM) | Colony forming Inhibition of MDA435 |
|---|---|---|
| AS-II-2229B-20 | 0.02 | 25% |
| | 0.03 | 56% |
| | 0.05 | 78% |
| | 0.10 | 94% |
| | 0.20 | 99% |

The ribonucleotide reductase R2 antisense construct designated AS-II-2229B-20 was tested for tumor cell cytotoxicity by comparing the results obtained with human tumor and non-tumor cell populations. Hela S3 tumor cells and WI 38 normal non-tumorigenic human cells were used. Tumor cells were found to be much more sensitive to the cytotoxic effects of AS-II-2229B-20 than normal non-tumorigenic cells. For example, analysis of cells three days after antisense exposure indicated that tumor cells were approximately 5-times more sensitive to the cytotoxic effects of AS-II-2229B-20 than normal non-tumorigenic cells averaged over 4–8 determinations.

These results indicate that short oligodeoxyribonucleotide sequences in an antisense orientation are excellent antitumor agents, and suggest that other antisense constructs that target the R2 message may have similar properties. The best antitumor agents would be those that exhibit suitable energy related characteristics important for oligonucleotide duplex formation with their complementary templates, and which show a low potential for self-dimerization or self-complementation [Anazodo et al., 1996]. An analysis of the R2 mRNA using a computer program (OLIGO, Primer Analysis Software, Version 3.4), was carried out to determine antisense sequence melting temperature, free energy properties, and to estimate potential self-dimer formation and self-complimentary properties [Anazodo, et al., 1996], of a series of additional antisense sequences (Table 1, SEQ. ID. NOS. 3–102) designed to target the R2 message. Table 1 shows a list of the additional R2 antisense inhibitors, with appropriate properties.

To test the antisense effects of many of these sequences as phosphorthioate deoxyribonucleotides, they were examined in relative colony forming experiments performed with a series of human tumor cell lines. Many of these antisense constructs, as predicted, are potent inhibitors of human tumor cell proliferation. For results obtained with cancer cells derived from the bladder, breast, lung, colon, pancreas, prostate, liver and cervix, see Table 13. In addition, in vivo studies with AS-II-626-20 were undertaken in C3H/HeN mice as reported in Table 14 and show a significant reduction in metastasis in the antisense treated mice.

Based on Example 2, treatment of human tumor cells with very low concentrations of short antisense sequences was tested to determine if these constructs could sensitize the tumor cells to inhibitory effects of other chemotherapeutic drugs. The concentration used was not cytotoxic in itself as shown in Table 9. The treatment of Hela S3 and Hela 1 mM cells with 0.02 µM of the AS-II-2229B-20 antisense construct increases the sensitivity of these cells to N-(phosphonacetyl)-L-aspartate (PALA) and to methotrexate (MTX) as shown in Table 11. These observations indicate that antisense compounds targeting the R2 message can act synergistically with well known chemotherapeutic agents.

TABLE 11

Synergistic Effect of AS-II-2229B-20 as Antisense Construct

| Cells | Drug | Drug Conc. | AS-II-2229-20 0.02 µM | Relative colony Forming Efficiency[c] |
|---|---|---|---|---|
| HeLa S3 | PALA | 20 µM | — | 350 ± 50 |
| | PALA | 20 µM | + | 90 ± 10 |
| HeLa S3 | MTX | 40 µM | — | 118 ± 32 |
| | MTX | 60 µM | — | 116 ± 13 |
| | MTX | 40 µM | + | 25 ± 5 |
| | MTX | 60 µM | + | 0 |
| HeLa 1 mM | PALA | 20 µM | — | 377 ± 21 |
| | PALA | 30 µM | — | 311 ± 9.5 |
| | PALA | 20 µM | + | 108 ± 7.5 |
| | PALA | 30 µM | + | 101 ± 2.0 |
| HeLa 1 mM | MTX | 40 µM | — | 28 ± 10 |
| | MTX | 60 µM | — | 12 ± 0.5 |
| | MTX | 40 µM | + | 6.5 ± 5.5 |
| | MTX | 60 µM | + | 3.5 ± 0.5 |

PALA = N-(phosphonacetyl)-L-aspartate
MTX = methotrexate
− = no treatment
+ = treatment provided
[c]The values are the average of two experiments Ribonucleotide reductase is composed of two dissimilar protein components coded by two distinct genes, R1 and R2.

Therefore, the results described herein above suggest that the R1 message may also be an appropriate target for designing short antisense molecules that have potent antitumor activity. To test this possibility a 20-mer deoxyribonucleotide phosphorothioate sequence in antisense orientation, designated AS-I-1395-20, was constructed and its antitumor abilities were tested. The antisense construct AS-I-1395-20 has the sequence 5'-ACA GGA ATC TTT GTA GAG CA-3' (SEQ ID No:103), and targets the R1 message at nucleotides 1395–1414.

TABLE 12

Reduced colony forming Efficiency Following Treatment with R1 Antisense Construct

| Conc. AS-I-1395-20 | % Inhibition |
|---|---|
| Cell Line: HeLa S3 | |
| 0 | |
| 0.2 μM | 75% (Exp.1) |
| 0.2 μM | 77% (Exp.2) |
| Cell Line: HeLa 1 mM | |
| 0 | — |
| 0.01 μM | 0 |
| 0.05 μM | 30% |
| 0.10 μM | 60% |
| Cell Line: Mouse SC2 | |
| 0 | — |
| 0.2 μM | 76% |

As shown in Table 12 it is an effective inhibitor of tumor cell proliferation using Hela S3 cells and Hela 1 mM drug resistant cells. These results demonstrate the usefulness of designing antisense sequences that target the R1 message, and suggest that other potential sites may also be effective.

Therefore, the R1 mRNA was analyzed in a search for antisense oligodeoxyribonucleotide sequences that exhibit suitable characteristics (as done for R2 mRNA and described above). Table 2 provides a list of additional antisense sequences with characteristics that are consistent with being antitumor agents.

Example 4

Inhibition of Transformation by R2 Antisense

Figure 9:
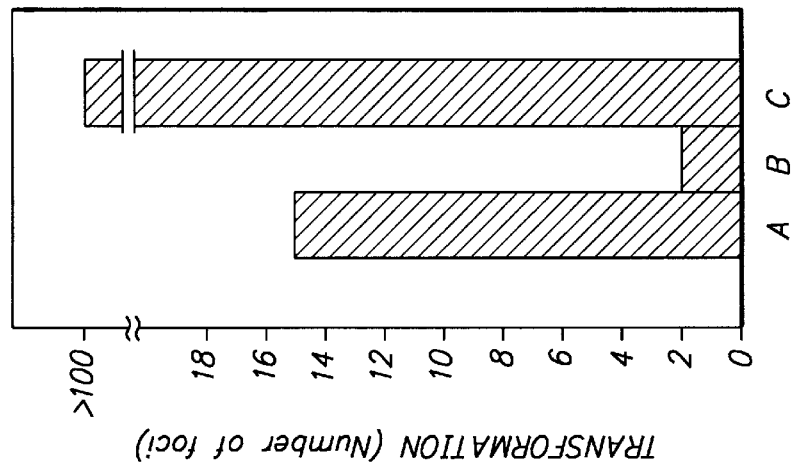
FIG. 9 is a graph showing the number of transformation foci in (a) NIH-3T3 mouse cells containing the H-ras oncogene, (b) NIH-3T3 mouse cells containing the H-ras oncogene and the R2 antisense sequence and (c) NIH-3T3 mouse cells containing the H-ras oncogene and the coding region sequence for R2. Results are averages of three experiments.

Utilizing the methods set forth in Examples 1–3, the inhibition of transformation of mammalian cells by treatment with the R2 antisense sequence of the R2 coding region [Fan et al., 1996b] was undertaken. NIH-3T3 mouse cells containing the H-ras oncogene were transfected with either the antisense orientation of the R2 coding sequence or the sense orientation of the R2 coding sequence. The results shown in FIG. 9 demonstrate that in the presence of the R2 antisense construct there was a decrease in transformed foci and reduced soft agar growth (FIG. 9, lane b) compared to the control cells (FIG. 9, lane a). As shown in Example 1, herein above, the R2 coding region can cooperate with H-ras to enhance malignancy as shown by the increased number of transformed foci (FIG. 9,lane c).

Furthermore, colony efficiency assays performed in soft agar as described herein demonstrated similar results. Colony forming efficiencies of 15.6±6.73 for NIH-3T3 mouse cells containing the H-ras oncogene, 4.4±2.62 for NIH-3T3 mouse cells containing the H-ras oncogene and the R2 antisense sequence, and 51+12.29 for NIH-3T3 mouse cells containing the H-ras oncogene and the coding region sequence for R2 were seen.

Example 5

Western Blot Analysis of As-II-626-20 Inhibition of Ribonucleotide Reductase R2 Protein Level in L60 Mouse Tumor Cells.

Figure 10A:
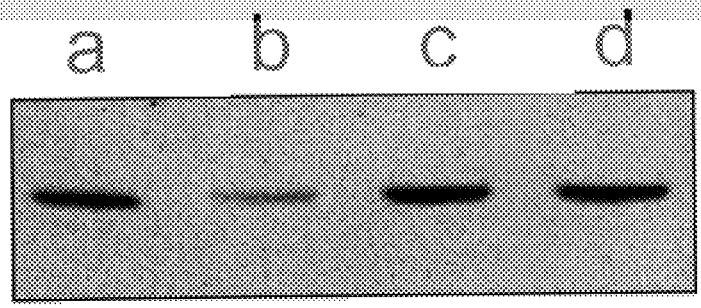
FIG. 10A–B are photographs of a Western blot analysis of AS-II-626-20 inhibition (A) and inhibition by a variety of R2 antisense oligonucleotides (B) of ribonucleotide reductase R2 protein level in L60 mouse tumor cells.
Figure 10B:
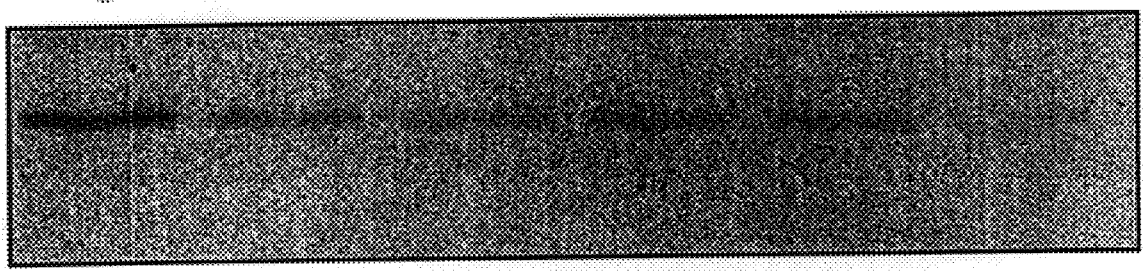

Cells were treated for 4 hours with growth medium supplemented with lipofectin but without antisense oligonucleotides (FIG. 10 A, lane a or with lipofectin medium containing 0.2 μM AS-II-626-20 (lane b). As added controls the tumor cells were also treated for 4 hours with growth medium supplemented with lipofectin and 0.2 μM oligonucleotide scrambled control, which contains the same proportion of nucleotides found in AS-II-626-20 but in a different order (ACGCACTCAGCTAGTGACAC, SEQ. ID. NO.164) (lane c) or with 0.2 μM mismatch oligonucleotide, GGCTAAACTGCTCCACCAAG (SEQ ID NO:163) which contains a four nucleotide mismatch mutation when compared to AS-II-626-20 (TCGC changed to CTGC) (lane d). Note the significant decrease in R2 protein in tumor cells treated with AS-II-626-20 (lane b) when compared to the controls (lanes a, c and d).

Decrease in R2 Protein Levels in Mouse L60 Tumor Cells Following Treatment with a Variety of R2 Antisense Oligonucleotides As Determined by Western Blot Analysis Cells were treated for 4 hours with 0.2 μM oligonucleotide in the presence of lipofectin (FIG. 10B, lanes b to f), or with lipofectin without oligonucleotide as a control (lane a). (lane b) Cells treated with AS-II-667-20; (lane c) cells treated with AS-II-816-20; (lane d) cells treated with AS-II-1288-20; (lane e) cells treated with AS-II-1335-20 and, (lane f) cells treated with AS-II-1338-20. Note the decrease in R2 protein levels in cells treated with antisense oligonucleotides that target the R2 mRNA, in keeping with their abilities to inhibit human tumor cell proliferation (Table 13).

TABLE 13

Reduced Relative Colony Forming Efficiency of Human Tumor Cells Following Treatment with 0.2 μM of Various Antisense Oligodeoxyribonucleotide Phosphorothioates Targeting the R2 Message, Expressed As % Inhibition

| Name (Re) | T24 | HCT116 | A549 | MDA-MB-231 | MIA PaCa-2 | PC-3 | HepG2 | Hela S3 | T-47D | H596 | Colo320 |
|---|---|---|---|---|---|---|---|---|---|---|---|
| AS-II-6-20 | 73.85 | ND | ND | 88.4 | 95.15 | 89.21 | 97.89 | ND | ND | ND | ND |
| AS-II-13-20* | 18.99 | 6.95 | 32.3 | 45.45 | ND | 52.38 | 24.11 | 19.85 | 15.33 | 19.68 | ND |
| AS-II-14-20 | 77.59 | ND | ND | 91.24 | 47.93 | 92.76 | 88.4 | ND | ND | ND | ND |
| AS-II-16-18 | 25.74 | 78.57 | 81.1 | 62.59 | ND | 89.48 | 75.89 | 68.7 | 7.13 | 34.5 | ND |
| AS-II-75-20* | 73.42 | 44.4 | 60.08 | 49.3 | 97.38 | 68.25 | 35.4 | 93.01 | 32.95 | ND | ND |
| AS-II-75-20 | 95.83 | ND | ND | 95.14 | 52.07 | 83.46 | 97.89 | ND | ND | ND | ND |
| AS-II-79-14 | 38.4 | 45.56 | 79.17 | 48.6 | 38.89 | 85.32 | 70.81 | 28.64 | 70.81 | ND | ND |

TABLE 13-continued

Reduced Relative Colony Forming Efficiency of Human Tumor Cells Following Treatment with 0.2 μM of Various Antisense Oligodeoxyribonucleotide Phosphorothioates Targeting the R2 Message, Expressed As % Inhibition

| Name (Re) | T24 | HCT116 | A549 | MDA-MB-231 | MIA PaCa-2 | PC-3 | HepG2 | Hela S3 | T-47D | H596 | Colo320 |
|---|---|---|---|---|---|---|---|---|---|---|---|
| AS-II-109-20* | 24.89 | 6.76 | 15.14 | 22.38 | 54.24 | 61.51 | 18.08 | 46.83 | 20.63 | 7.28 | ND |
| AS-II-110-20 | 87.78 | 71.69 | 89.38 | 90.92 | 47.51 | 92.06 | 97.14 | 53.98 | ND | ND | ND |
| AS-II-114-20 | 87.45 | 86.1 | 83.51 | 76.22 | 90.05 | 92.66 | 78.72 | 79.25 | 90.83 | 46.3 | ND |
| AS-II-127-12 | 50.63 | 54.34 | 69.33 | 38.46 | 53.24 | 79.56 | 71.75 | 86.45 | 37.54 | ND | ND |
| AS-II-130-20 | 51.94 | 57.98 | 86.48 | ND | 82.11 | 74.66 | 94.28 | ND | ND | ND | ND |
| AS-II-134-20 | ND | ND | ND | ND | ND | 77.51 | ND | ND | ND | ND | ND |
| AS-II-151-20 | ND | 78.09 | 84.28 | 41.64 | 75.38 | 85.68 | 89.58 | 66.75 | 95.89 | 69.12 | 90.12 |
| AS-II-163-20* | 5.49 | 29.05 | 37.13 | 22.73 | 9.88 | 7.14 | 18.64 | 45.8 | 9.81 | 32.08 | ND |
| AS-II-166-20 | 68.99 | 73.84 | 81.1 | 29.02 | 91.36 | 74.11 | 78.72 | 80.1 | 91.4 | 61.99 | ND |
| AS-II-185-20 | 21.94 | ND | 71.51 | 17.4 | 29.32 | 4.37 | 53.44 | 19.38 | 94.52 | 24.53 | ND |
| AS-II-189-20 | 18.57 | 86.78 | 76.57 | 39.86 | 70.52 | 73.12 | 57.86 | 76.67 | 96.63 | 26.15 | ND |
| AS-II-201-20 | 96.2 | 45.56 | 90.55 | 25.17 | 70.22 | 65.08 | 59.32 | 90.87 | 98.53 | 49.6 | ND |
| AS-II-217-20 | 65.02 | 61.85 | ND | 52.7 | 87.38 | 87.41 | 99.55 | ND | ND | ND | ND |
| AS-II-225-20 | 73.23 | 59.5 | 92.9 | ND | 95.44 | 80.06 | ND | 96.99 | ND | ND | ND |
| AS-II-253-14 | 19.41 | 53.28 | 61.62 | 45.37 | ND | 67.26 | 42 | 65.18 | 27.09 | 0.81 | ND |
| AS-II-280-20 | 90.56 | 69.42 | 61.81 | 79.14 | 53.94 | 77.51 | 97.14 | 41.79 | ND | ND | ND |
| AS-II-288-12 | 30.38 | 67.57 | 70.49 | 52.1 | 30.09 | 74.01 | 65.89 | 57.63 | ND | 12.67 | ND |
| AS-II-323-20 | ND | 55.8 | 91.24 | ND | 97.55 | 79.76 | 96.39 | ND | ND | ND | ND |
| AS-II-344-20 | ND | ND | ND | ND | ND | 80.06 | ND | ND | ND | ND | ND |
| AS-II-362-20 | 89.63 | 62.81 | 61.81 | 85.83 | 34.2 | 75.78 | 95.78 | 45.69 | ND | ND | ND |
| AS-II-391-17 | ND | ND | ND | ND | 26.35 | 93.25 | 60.64 | ND | ND | ND | ND |
| AS-II-404-20 | 84.26 | ND | 52.17 | 85.83 | 17.84 | 77.08 | 84.79 | 58.37 | ND | ND | ND |
| AS-II-412-20 | 22.2 | 27.98 | 43.78 | ND | 55.25 | 73.96 | 26.23 | ND | ND | ND | ND |
| AS-II-414-20 | 11.67 | 19.1 | 12.44 | ND | 36.11 | 60.94 | 30.89 | ND | ND | ND | ND |
| AS-II-425-20 | 90.37 | ND | 57.38 | 89.75 | 65.2 | 75.65 | 97.89 | 63.09 | ND | ND | ND |
| AS-II-439-20 | 67.84 | 64.7 | 76.46 | ND | 92.69 | 77.66 | 73.04 | ND | ND | ND | ND |
| AS-II-472-20 | 69.26 | 67.23 | 96.99 | ND | 97.13 | 90.7 | ND | ND | ND | ND | ND |
| AS-II-494-20 | 54.23 | 50.28 | 33.85 | 54.78 | 25.31 | 80.6 | 93.37 | 48.62 | ND | ND | ND |
| AS-II-496-16 | 78.48 | 70.85 | 74.45 | 45.8 | ND | 88.84 | 54.8 | 52.21 | 10.79 | ND | ND |
| AS-II-549-20 | 45.46 | 47.83 | 30.57 | 40.13 | 17.01 | ND | 84.04 | 27.8 | ND | ND | ND |
| AS-II-579-20 | 76.68 | 69.08 | 95.49 | 66.89 | 97.55 | 88.16 | 94.28 | ND | ND | ND | ND |
| AS-II-619-20 | 86.3 | ND | 65.67 | 91.08 | 39.83 | 88.01 | 92.02 | 31.22 | ND | ND | ND |
| AS-II-626-20 | 76.79 | 70.46 | 95.14 | 90.21 | 75.62 | 83.23 | 75.89 | 67.92 | 66.12 | ND | ND |
| AS-II-634-20 | 83.52 | ND | 57.76 | 92.44 | ND | 77.86 | 95.78 | 48.94 | ND | ND | ND |
| AS-II-667-20 | 70.48 | 76.9 | 70.3 | ND | 85.26 | 91.8 | 88.23 | ND | ND | ND | ND |
| AS-II-784-20 | 87.23 | 78.09 | 83.8 | 33.92 | 62.04 | 88.99 | 80.89 | 81.48 | 85.39 | ND | ND |
| AS-II-798-20 | 84.72 | 64.46 | 70.49 | 83.92 | 34.65 | 83.21 | 89.46 | 56.42 | ND | ND | ND |
| AS-II-816-20 | 73.91 | 88.22 | 78.4 | ND | 93.21 | 94.08 | 93.08 | ND | ND | ND | ND |
| AS-II-861-20 | 73.5 | 74.2 | 95.78 | 89.98 | 97.3 | 87.33 | 96.08 | ND | ND | ND | ND |
| AS-II-890-20 | 82.07 | ND | 81.6 | 88.2 | 66.02 | 87.93 | ND | ND | ND | ND | ND |
| AS-II-909-20 | 78.57 | ND | 78.68 | 45.96 | 46.13 | 84.86 | ND | ND | ND | ND | ND |
| AS-II-933-20 | 64.84 | 67.24 | 53.52 | 64.89 | 35.68 | 86.91 | 79.97 | 26.86 | ND | ND | ND |
| AS-II-981-20 | 86.3 | 66.84 | 74.25 | 91.48 | ND | 85.16 | 95.03 | 69.43 | ND | ND | ND |
| AS-II-1001-20 | 86.11 | 55.58 | 71.36 | 82.17 | 64.21 | 85.94 | 90.36 | ND | ND | ND | ND |
| AS-II-1006-20 | 61.49 | 45.56 | 61.62 | ND | 47.93 | 92.58 | 89.31 | 41.79 | ND | ND | ND |
| AS-II-1023-20 | 58.26 | ND | 34.52 | ND | 42.82 | 87.63 | ND | ND | ND | ND | ND |
| AS-II-1040-20 | 59.49 | 70.08 | 85.82 | ND | 43.52 | 40.08 | 77.78 | 71.87 | 64.76 | ND | ND |
| AS-II-1048-20 | 40.32 | 42.63 | 65.67 | 66.88 | 33.4 | 84.38 | 77.56 | 39.19 | ND | ND | ND |
| AS-II-1144-20 | 62.9 | 54.25 | 61.81 | ND | 46.89 | 80.21 | 92.17 | 50.57 | ND | ND | ND |
| AS-II-1182-20 | 94.51 | 88.13 | 80.06 | ND | 84.72 | 92.76 | 92.23 | 90.61 | 92.41 | ND | ND |
| AS-II-1197-20 | 90.3 | 84.85 | 89.15 | 50.35 | 70.68 | 74.4 | 76.32 | 82.68 | 81.95 | ND | ND |
| AS-II-1217-20 | 66.36 | 68.68 | 91.49 | ND | 34.85 | 81.03 | ND | ND | ND | ND | ND |
| AS-II-1224-20 | 38.31 | 41.78 | 55.06 | ND | 17.22 | 80.66 | 76.05 | 14.8 | ND | ND | ND |
| AS-II-1254-20 | 41.53 | 28.54 | 36.74 | ND | 3.32 | 73.31 | 83.28 | 7.64 | ND | ND | ND |
| AS-II-1278-20 | 65.42 | ND | ND | 90.68 | 57.05 | 85.31 | ND | ND | ND | ND | ND |
| AS-II-1288-20 | 56.75 | 66.43 | 61.04 | ND | 80.71 | 93.55 | 80.41 | ND | ND | ND | ND |
| AS-II-1302-20 | 70.56 | 71.98 | 93.17 | 92.2 | 23.86 | 79.01 | ND | ND | ND | ND | ND |
| AS-II-1335-20 | 59.95 | 67.87 | 78.59 | ND | 78.78 | 90.04 | 72.98 | ND | ND | ND | ND |
| AS-II-1338-20 | 63.16 | 74.73 | 63.93 | ND | 79.17 | 93.75 | 80.41 | ND | ND | ND | ND |
| AS-II-1342-20 | 59.76 | 73.74 | 65.67 | ND | 73.77 | 89.84 | 82.2 | ND | ND | ND | ND |
| AS-II-1345-20 | 51.26 | 65.7 | 73.1 | 94.11 | 77.39 | 89.58 | 75.42 | ND | ND | ND | ND |
| AS-II-1362-20 | ND | 78.47 | 83.9 | 70.22 | 44.14 | 77.38 | 80.41 | ND | ND | ND | ND |
| AS-II-1364-20 | 66.59 | 77.29 | 95.59 | 93.87 | 59.34 | 79.01 | ND | ND | ND | ND | ND |
| AS-II-1381-20 | 71.37 | 89.48 | 86.02 | 44.41 | 73.77 | 75 | 62.34 | 80.53 | 93.62 | 45.28 | ND |
| AS-II-1390-20 | 61.13 | 62.18 | 88.31 | 66.89 | 82.77 | 76.76 | 90.21 | ND | ND | ND | ND |
| AS-II-1438-20 | 43.7 | ND | 51.27 | 69.06 | 42.13 | 83.96 | ND | ND | ND | ND | ND |
| AS-II-1499-20 | 82.81 | 83.01 | 87.8 | 41.26 | 81.17 | 77.28 | 77.5 | 87.56 | 96.67 | 78.3 | ND |
| AS-II-1517-20 | ND | ND | ND | ND | ND | 91.75 | ND | ND | ND | ND | ND |
| AS-II-1538-20 | 67.29 | 51.28 | 90.34 | ND | 50.62 | 84.71 | 96.84 | ND | ND | ND | ND |
| AS-II-1560-20 | 32.49 | 85.8I | 84.19 | 46.15 | 83.8 | 78.37 | 73.63 | 82.16 | 86.6 | 71.16 | ND |
| AS-II-1581-20 | 68.22 | 66.85 | 90.55 | ND | 24.07 | 85.83 | 93.07 | ND | ND | ND | ND |
| AS-II-1659-20 | 74.09 | ND | 54.7 | 42.86 | 42.54 | 81.56 | ND | ND | ND | ND | ND |
| AS-II-1666-20 | 71.71 | ND | 54.82 | 26.71 | 49.72 | 86.06 | ND | ND | ND | ND | ND |

TABLE 13-continued

Reduced Relative Colony Forming Efficiency of Human Tumor Cells Following Treatment with 0.2 µM of Various Antisense Oligodeoxyribonucleotide Phosphorothioates Targeting the R2 Message, Expressed As % Inhibition

| Name (Re) | T24 | HCT116 | A549 | MDA-MB-231 | MIA PaCa-2 | PC-3 | HepG2 | Hela S3 | T-47D | H596 | Colo320 |
|---|---|---|---|---|---|---|---|---|---|---|---|
| AS-II-1700-20 | 70.94 | ND | 77.28 | 30.75 | 34.52 | 90.63 | ND | ND | ND | ND | ND |
| AS-II-1768-20 | 74.56 | ND | 86.8 | 91.56 | 60.36 | 86.36 | ND | ND | ND | ND | ND |
| AS-II-1773-20 | 15.19 | 75.58 | 70.11 | 44.76 | 45.68 | 70.04 | 58.19 | 80.27 | 84.38 | 66.04 | ND |
| AS-II-1775-12 | 85.54 | 5444 | 63.55 | 48.6 | 27.78 | 78.17 | 43.97 | 68.61 | ND | 18.6 | ND |
| AS-II-1790-20 | ND | ND | ND | ND | ND | 87.86 | ND | ND | ND | ND | ND |
| AS-II-1819-20 | 53.74 | ND | ND | 90.68 | 20.02 | 85.46 | 83.89 | ND | ND | ND | ND |
| AS-II-1976-20 | ND | ND | ND | 89.6 | ND | 88.16 | ND | ND | ND | ND | ND |
| AS-II-1989-20 | 77.43 | 78.47 | 83.9 | 54.9 | 70.22 | 77.38 | 80.7 | 61.41 | 90.83 | 56.33 | ND |
| AS-II-2009-20 | 61.84 | 69.92 | 93.32 | 96.25 | 93.74 | 83.36 | 96.99 | ND | ND | ND | ND |
| AS-II-2026-20 | 95.46 | 81.47 | 88.81 | 77.1 | 87.65 | 95.29 | 94.54 | 83.79 | 93.41 | 84.16 | ND |
| AS-II-2044-20 | 53.63 | 49.34 | 25.55 | 19.11 | 24.48 | 74.48 | 62.35 | 24.55 | ND | ND | ND |
| AS-II-2067-20 | 49.6 | 47.16 | 64.71 | 49.68 | 41.08 | 85.94 | 90.36 | 24.88 | ND | ND | ND |
| AS-II-2083-20 | 82.43 | 87.46 | 90.65 | 68.88 | 71 | ND | 93.64 | 84.58 | 89.32 | 82.98 | 87.28 |
| AS-II-2083-20* | 9.52 | 41.16 | 31.73 | ND | ND | 82.03 | 46.14 | 6.96 | 48.61 | 49.87 | 52.54 |
| AS-II-2128-20 | 83.74 | ND | 87.31 | 91.3 | 39.23 | 88.89 | ND | ND | ND | ND | ND |
| AS-II-2151-20 | 79.83 | ND | 79.19 | 95.14 | 62.15 | 84.86 | ND | ND | ND | ND | ND |
| AS-II-2164-20 | 61.84 | 50.08 | 91.15 | 69.03 | 89.36 | 83.36 | 93.07 | ND | ND | ND | ND |
| AS-II-2182-20 | 67.76 | 77.66 | 90.97 | 84.95 | 56.43 | 85.91 | 95.48 | ND | ND | ND | ND |
| AS-II-2229A-20 | 50.34 | 93.01 | 69.72 | ND | 33.61 | 89.58 | 73.26 | 63.15 | 58.82 | ND | ND |
| AS-II-2372-20 | 61.13 | 64.7 | 96.41 | 90.09 | 94.36 | 86.06 | ND | ND | ND | ND | ND |

Legend to Table 13
The antisense oligonucleotides were fully thioated unless indicated (*), as described in Table 1
The values for relative colony-forming efficencies are averages obtained from 2–8 determinations.
ND = not determined.
The various cell lines were obtained from the American Type Culture Collection, Rockville Maryland.

Information About These Human Cancer Cells:

T24=bladder cell carcinoma
HCT116=colon cell carcinoma
A549=lung cell carcinoma
MDA-MB-231=breast cell adenocarcinoma
MIA PaCa-2=pancreatic cell carcinoma
PC-3=prostrate cell adenocarcinoma
HepG2=hepatocellular carcinoma
HeLaS3=cells isolated from a carcinoma of the cervix
T-47D=breast ductal carcinoma
H596=lung adenosquamous carcinoma cells
Colo320=colon cell adenocarcinoma Example 6

Metastatic Characteristics of Tumor Cells Following Treatment with an Antisense Oligonucleotide $10^5$ cells of the mouse 10T½ r-3 cell line either treated for 4 hours with lipofectin without oligonucleotide supplement (none) or with lipofectin containing 0.2 µM AS-II-626-20, were injected intravenously (tail vein) into C3H/HeN syngenic mice and lung tumors were analyzed as previously described (Damen et al. 1991). The r-3 cell line is highly malignant and has been described previously (Taylor et al., 1992). The differences observed between the AS-II-626-20 treated and untreated groups were statistically significant (p value=0.027). Clearly, AS-II-626-20 treated tumor cells exhibited a marked reduction in metastatic potential. See Table 14.

TABLE 14

Metastatic Characteristics of r-3 Mouse 10T½ tumor cells in Syngenic Mice following treatment with the antisense oligonucleotide AS-II-626-20

| Oligonucleotide Treatment | Frequency of Mice tumors | Number of Lung Tumors (mean ± SE) |
|---|---|---|
| none | 4/4 | 6.0 ± 1.58 |
| 0.2 µM | 1/4 | 0.25 ± 0.25 |

Example 7

Inhibition of Colony Forming Ability

Figure 11:
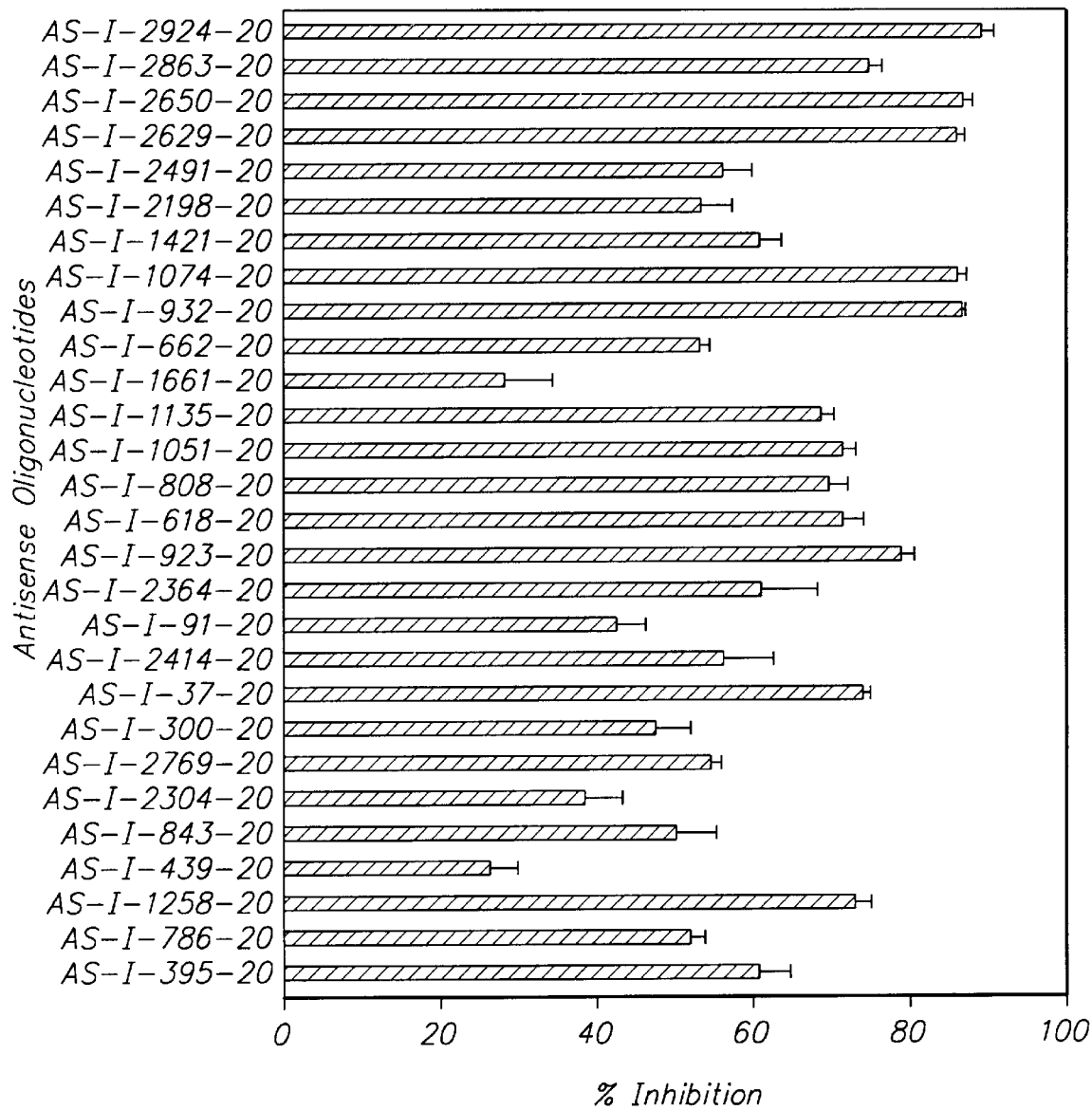
FIG. 11 is a graph showing the percentage inhibition by various antisense oligonucleotides in the colony formation of MDA-MB-231 human breast cancer cells.

Colony forming ability of MDA-MB-231 human breast cancer cells treated with 28 different antisense oligonucleotides was estimated as previously described (Choy et al., 1988). Aliquots of cell suspension were seeded into 60 mm Petri dishes and incubated at 37° C. overnight in α-MEM medium supplemented with 10% fetal bovine serum. Cells were washed in 5 ml of phosphate buffered saline, pH 7.2, prior to 0.2 µM antisense/lipofectin treatments for 4 hours. The media containing the antisense oligonucleotides were removed and cells were washed once and cultured in growth medium for 7 to 10 days. Colonies were stained with methylene blue and scored as described (Choy et al., 1988; Huang and Wright 1994). Percent inhibition was calculated by comparison with the number of colonies present in cultures grown in the absence of antisense oligonucleotides. All experiments were performed in quadruplicate. FIG. 11 is a graph of the percentage inhibition of colony formation by treatment with the various antisense oligonucleotides. This shows that the antisense oligonucleotides directed against human ribonucleotide reductase R1 are able to inhibit colony formation of human breast cancer cells.

Figure 12:
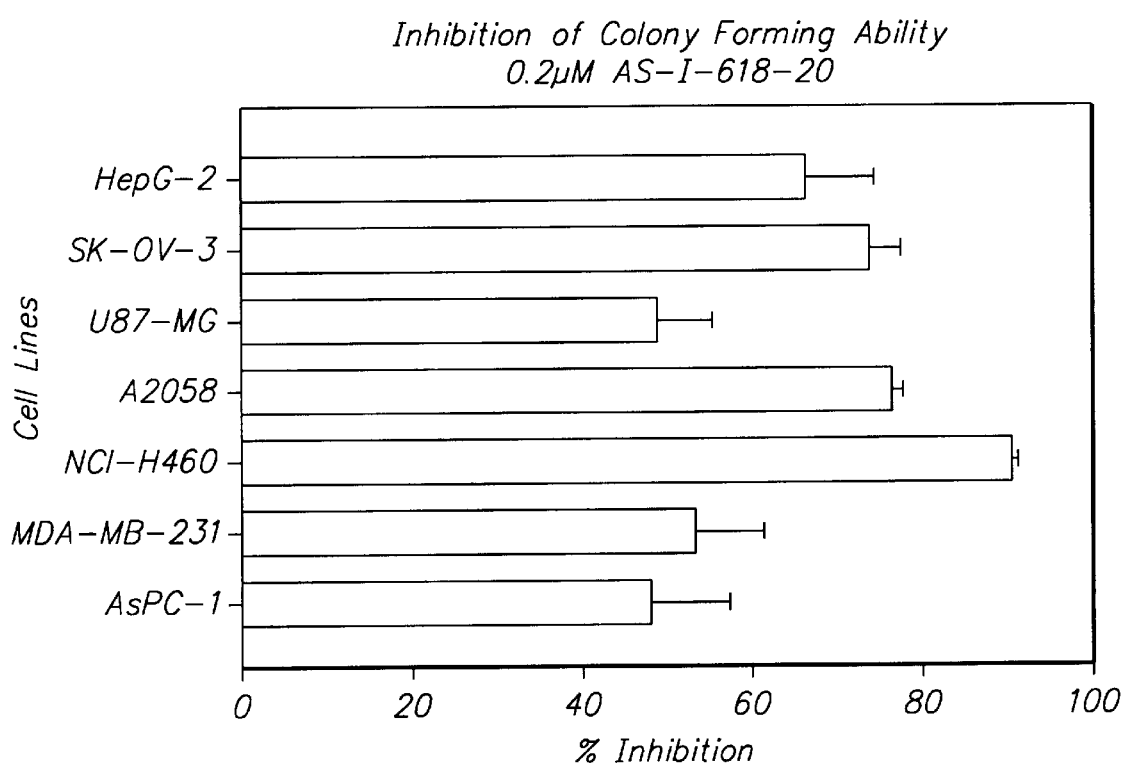
FIG. 12 is a graph showing the inhibition of colony formation by AS-I-618-20. The cell lines are HepG2 (liver), SK-OV-3 (ovary), U87 (brain), A2058 (melanoma), H460 (lung), MDA-MB-231 (breast) and AsPC-1 (pancreas).

Colony forming ability of various human tumor cell lines was estimated by determining relative colony forming efficiencies (Choy et al., 1988). Cells from various cell lines were washed in 5 ml of phosphate buffered saline, pH 7.2. The cells were treated with 0.2 μM AS-I-618-20 antisense oligonucleotide/lipofectin for 4 hours. The medium containing the antisense oligonucleotide was then removed and the cells were gently washed with 5 ml of growth medium. The cells were cultured in growth medium containing 10% fetal bovine serum for seven to ten days. Surviving cells were visualized by methylene blue staining and colonies were scored (Choy et al., 1988; Huang and Wright 1994) FIG. 12 shows the results with standard errors. The following human tumor cell lines were evaluated: HepG2 (liver), SK-OV-3 (ovary), U87 (brain), A2058 (melanoma), H460 (lung), MDA-MB-231 (breast) and AsPC-1 (pancreas).

Example 8

Western Blot Analysis of Dose Dependent Inhibition

Figure 13:
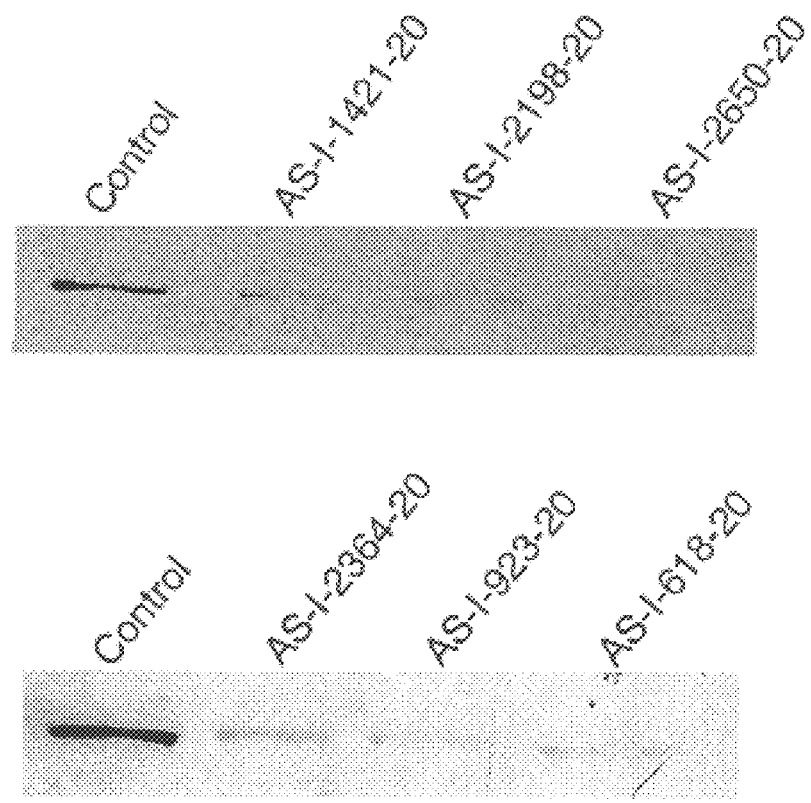
FIG. 13 is a photograph of a Western blot of R1 protein expression after treatment of MDA-MB-231 human breast cancer cells with various antisense oligonucleotides.

MDA-MB-231 human breast cancer cells were treated with different antisense oligonucleotides and changes in R1 protein levels were analyzed by Western blotting. Cells were treated with oligonucleotides at a concentration of 0.2 μM, whole cell protein extracts were prepared after 24 hours incubation and R1 protein levels were determined by western blot as previously described (Choy et al., 1988; Hurta and Wright 1995B; Fan et al., 1996A). Protein extracts prepared from untreated cells were used as a control. FIG. 13 is a photograph of the western blot showing the level of R1 protein expression after treatment with the various antisense oligonucleotides.

Figure 14A:
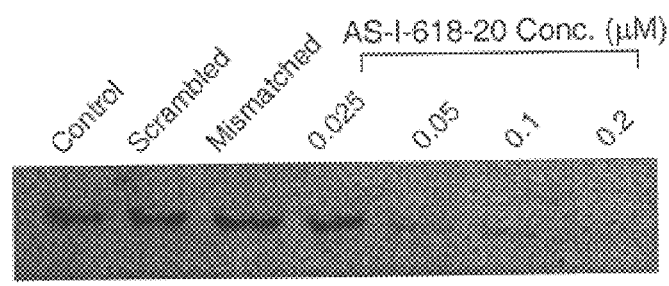
FIG. 14A is a photograph of the Western Blot of R1 protein expression after treatment with AS-I-618-20. control=untreated cells, scrambled—cells treated with a scrambled version of AS-I-618-20 (same proportion of GTAC but an entirely different sequence) and mismatched—a mutated version of AS-I-618-20 with a 4 base mismatch.
Figure 14B:
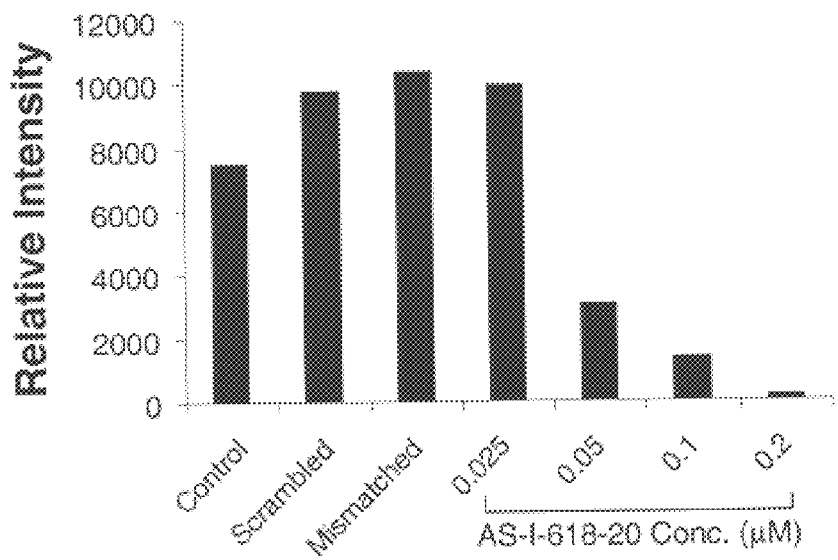
FIG. 14B is a graph of the R1 protein levels in the Western Blot quantitated using Image Quant program (Molecular Dynamics) and expressed in arbitrary units (Relative intensity).

MDA-MB-231 human breast cancer cells were treated with increasing concentrations (0.025–0.2 μM) of AS-I-618-20 along with an untreated control (Control), and with 0.2 ,μM of a scrambled control analogue of AS-I-618-20 (Scrambled)5'-ACTGCAGCCTATATGCAGCT-3' [SEQ ID NO:214] and a mismatched control analogue of AS-I-618-20+(mismatched) 5'-CTCTAGCGTCATATAGCCGA-3' [SEQ ID NO:215] that contains four base changes. Whole cell protein extracts were prepared after 24 hours incubation and Western blot analysis was performed as previously described (Choy et al., 1988; Hurta and Wright 1994; Fan et al., 1996A). FIG. 14A is a photograph of the Western Blot. FIG. 14B is a graph of the R1 protein levels in the Western Blot quantified using Image Quant program (Molecular Dynamics) and expressed in arbitrary units (Relative intensity).

Example 9

AS-I-618-20 Inhibits the R1 Target as Demonstrated by Immunoprecipitation Analysis There are two general methods for obtaining information about protein levels in a cell. Western blot analysis provides information about the steady state levels of a specific protein (shown in Example 8) and immunoprecipitation analysis provides information about the synthesis of the protein in the cell.

Immunoprecipitation was performed with minor modifications according to Choy et al., [1998], by using saturating amounts of AD-203 anti-R1 monoclonal antibody. Immunoprecipitation was performed on total cell extract and formalin fixed *Staphylococcus aureus* cells. The resulting precpitated products were analyzed on SDS-polyacrylamide gels. After equilibration in buffer containing glycine, gels were dried and exposed to film. Autoradiograms were scanned and peak areas were quantitated.

Figure 15:
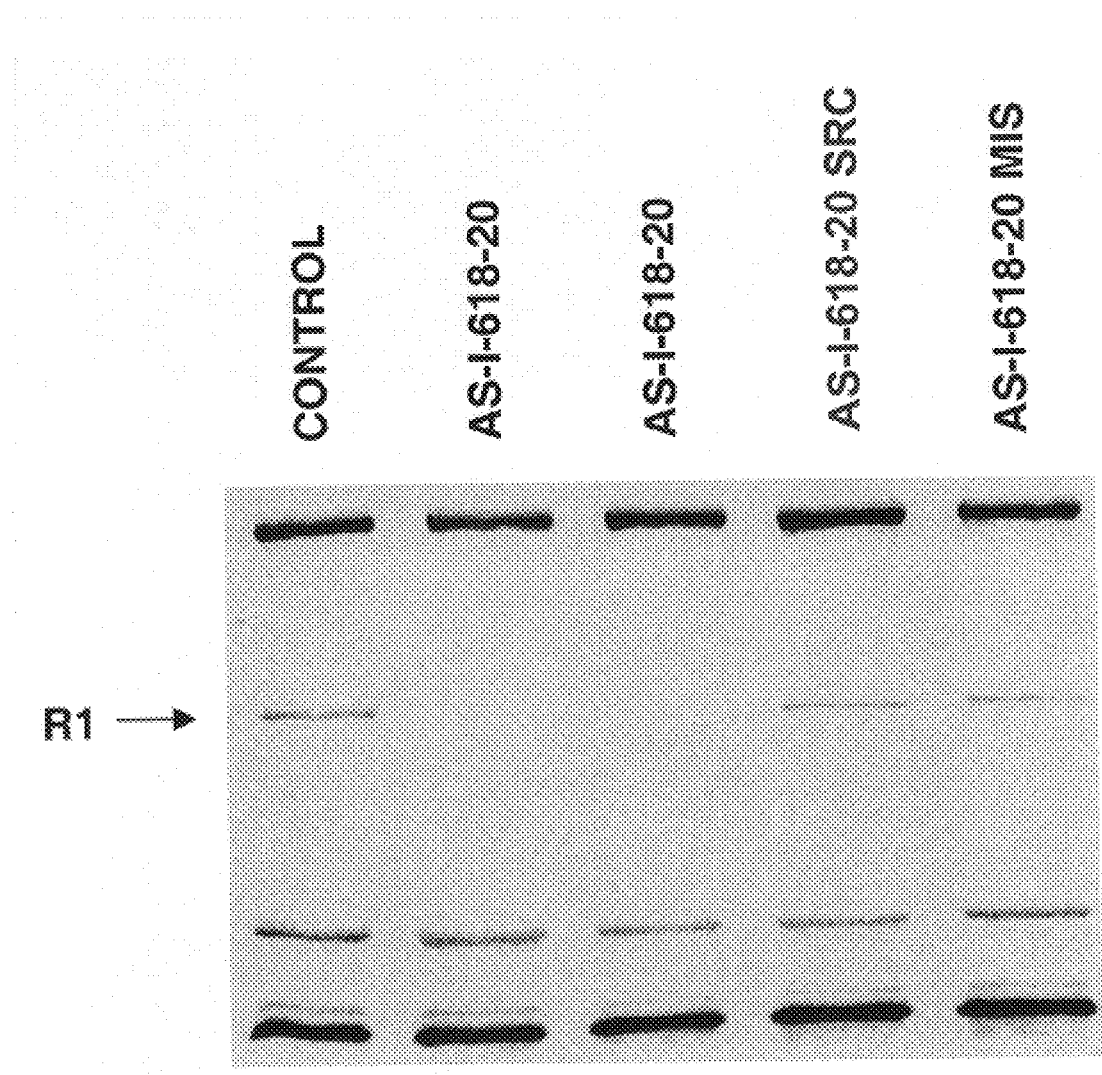
FIG. 15 is a photograph of immunoprecipitation gel. SRC—scrambled version of AS-I-618-20; MIS—mismatched version of AS-I-618-20

In FIG. 15, SCR- cells treated with a scrambled version of AS-I-618-20 (same proportion of GTAC but an entirely different sequence) and MIS=a mutated version of AS-I-618-20 with a 4 base mismatch.

The immunoprecipitation results using AsPC-1 tumor cells (derived from a human pancreas tumor) demonstrate that AS-I-618-20 specifically inhibits the synthesis of R1 protein in tumor cells.

Example 10

Northern Blot Analysis

RNA was subjected to electrophoresis through 1% formaldehyde agarose gels followed by transfer to nylon membranes. Blots were prehybridized and hybridized as previously described (McClarty et al., 1990; Hurta and Wright 1994). Hybridization occurred in the presence of a R1 fragment (McClarty et al.,1987). Probes were labeled with α-$^{32}$P and washed and autoradiography was performed as previously outlined (McClarty et al., 1988; Hurta and Wright, 1994). Loading was estimated with a plasmid containing the glyceraldehyde-3-phosphate dehydrogenase sequence as described (Choy et al., 1989; Edwards 1985).

Figure 16:
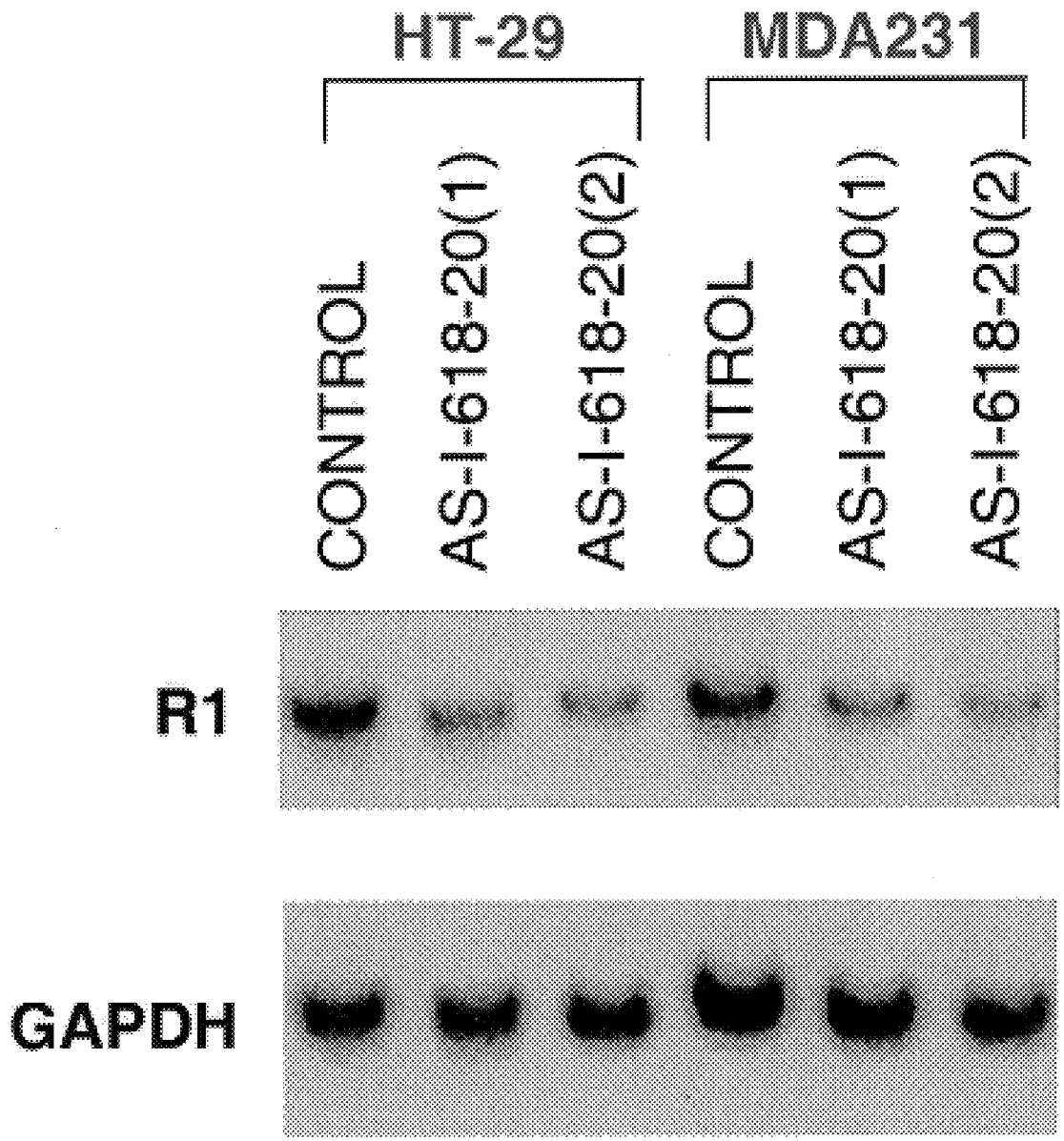
FIG. 16 is an autoradiograph of a Northern Blot of mRNA from various cells either untreated or treated with AS-I-618-20. HT-29 is a human colon adenocarcinoma cell line and MDA-MB-231 is a human breast adenocarcinoma cell line.

FIG. 16 is an autoradiograph of the Northern Blot of mRNA from various cells either untreated or treated with AS-I-618-20. There is a marked reduction in R1 mRNA levels in cells previously treated with AS-I-618-20 compared to control cells that were not exposed to the antisense compound. HT-29 is a human colon adenocarcinoma line and MDA-MB-231 is a human breast adenocarcinoma cell line.

Example 11

Tumorigenicity Assay

Figure 17:
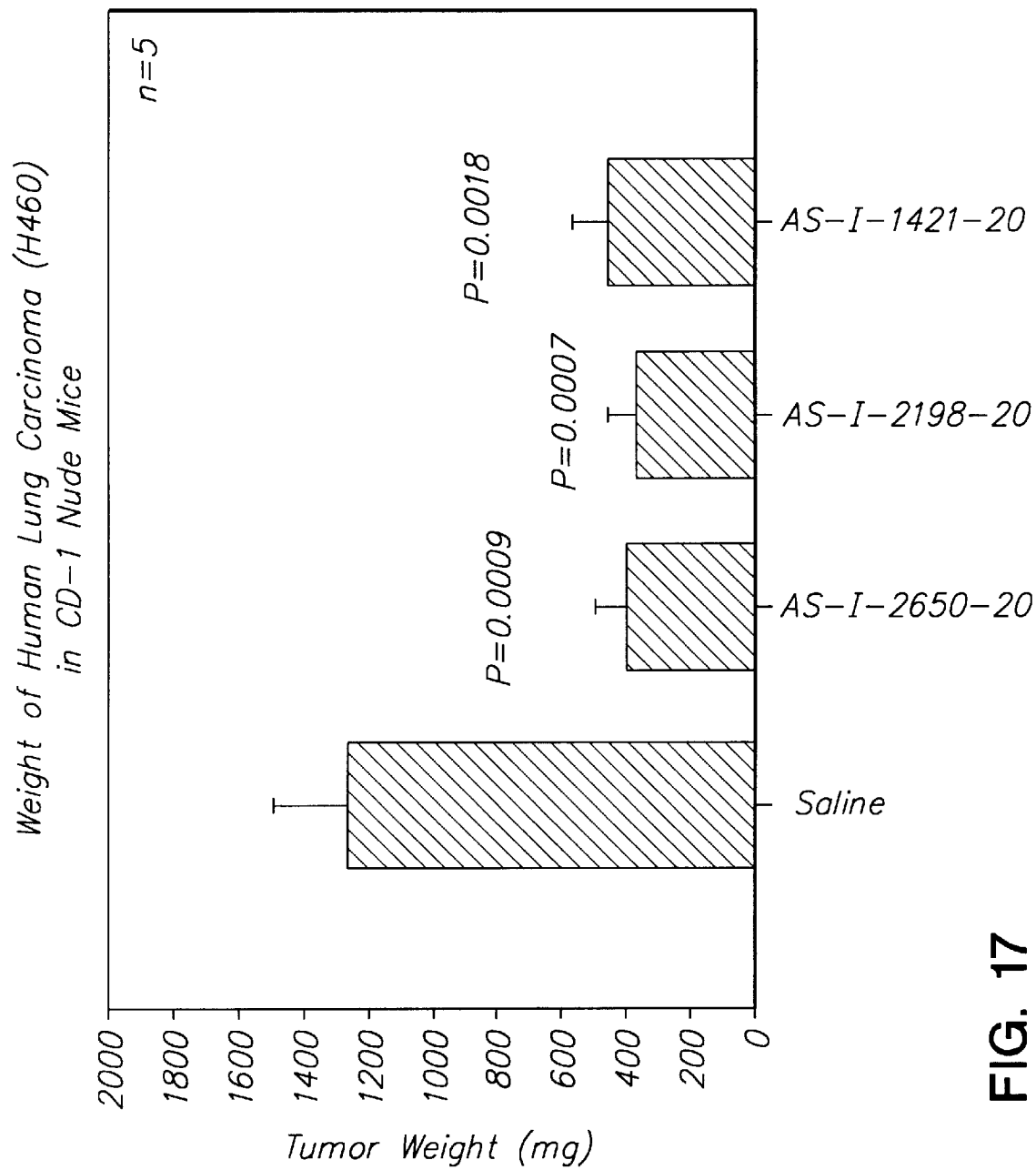
FIG. 17 is a graph showing the weight of human lung cancinoma (H460) tumors in mice after treatment with various antisense oligonucleotides.

Tumor growth rates and tumor weights were determined as previously described (e.g. Egan et al., 1987A; Egan et al.,1987B; Damen et al., 1989; Fan et al., 1996A). Briefly, human lung carcinoma (H460) cells were removed from culture plates, washed and a 0.1 ml aliquot (range between $10^6$ to $10^7$ cells)was injected subcutaneously into the right flank of female CD-1 nude mice, from Charles River, Montreal. An antisense oligonucleotide in normal saline was administered by tail vein injections every second day following detection of a palpable tumor mass. The tumor was removed from the mice approximately 14 days after treatment and the weight of the tumor was measured. FIG. 17 is a graph showing the reduced weight of the tumor in mice treated with the antisense oligonucleotides.

Figure 18:
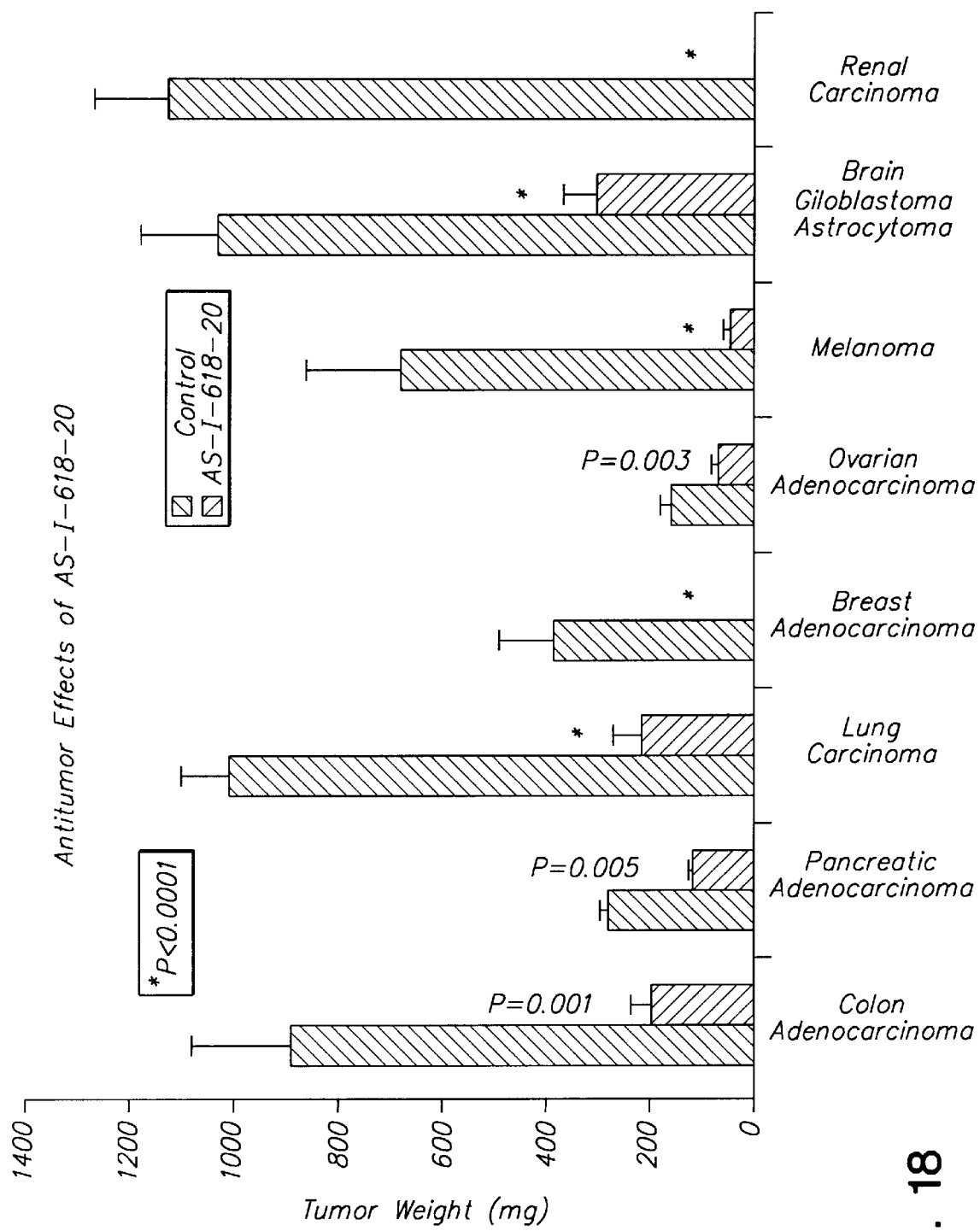
FIG. 18 is a graph showing the weight of the various tumors in mice after treatment with AS-I-618-20. Light color bars are results obtained from untreated controls, and the darker color bars are results from animals treated with AS-I-618-20.

Next the antitumor effects of AS-I-618-20 against various human tumor cell lines was tested. Briefly, cells were removed from culture plates, washed and a 0.1 ml aliquot of each cell line (range between $10^6$ to $10^7$ cells)was injected subcutaneously into the right flank of female nude mice, CD-1 or BALB/c nu/nu from Charles River, Montreal. Antisense oligonucleotide AS-I-618-20 (10 mg/kg) in normal saline was administered by tail vein injections every second day following detection of a palpable tumor mass. Some animals received saline alone, without oligonucleotide. FIG. 18 is a graph showing the tumor weight after treatment. Light color bars are results obtained from untreated controls, and the darker color bars are results from animals treated with AS-I-618-20.

Figure 19:
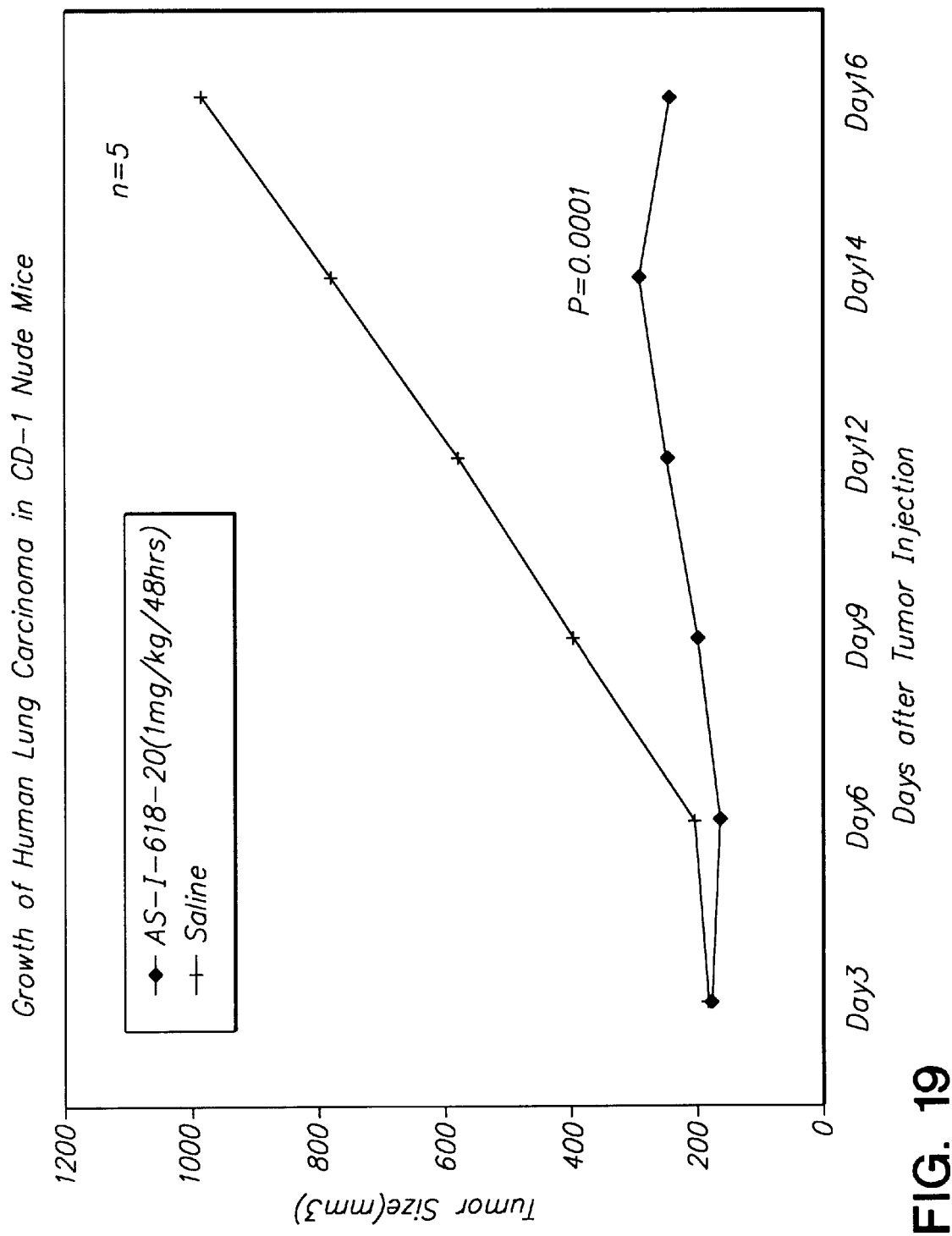
FIG. 19 is a graph showing the rate of growth of the human lung carcinoma tumors in nude mice with or without treatment with 1 mg/kg AS-I-618-20.

In addition, the growth of the human lung carcinoma tumor in CD-1 nude mice was measured after treatment with antisense AS-I-618-20. FIG. 19 shows the rate of growth of the tumor with or without treatment.

Example 12

Effects of AS-I-618-20 on R1 mRNA Levels in HT-29 Tumors

Figure 20:
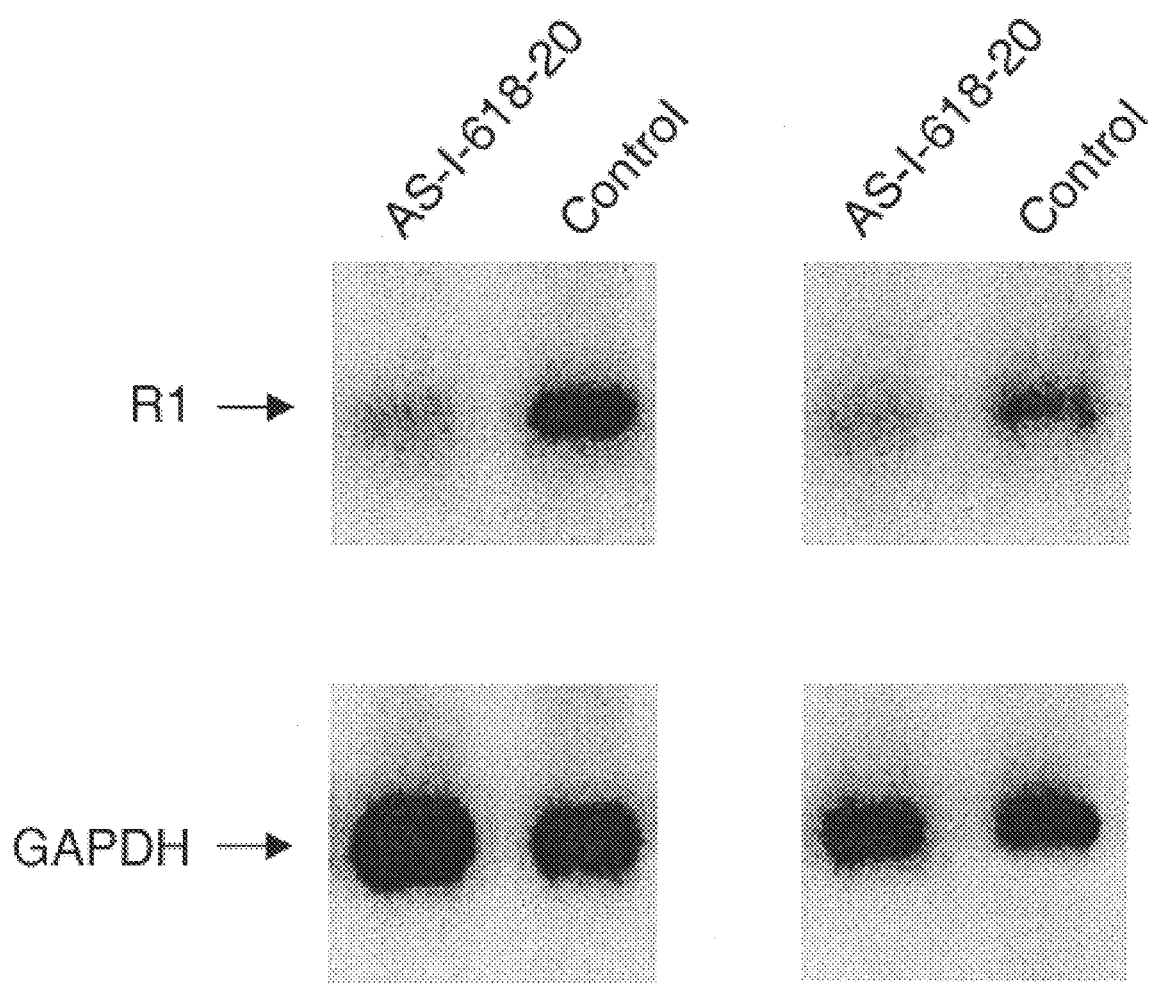
FIG. 20 is an autoradiograph of a Northern blot of ribonucleotide reductase R1 mRNA in HT-29 human colon tumors in mice after treatment with AS-I-618-20.

HT-29 human colon cancer cells were injected subcutaneously in CD-1 nude mice. After the establishment of tumors, AS-I-618-20 prepared in saline solution was administered by tail vein injections every second day at a concentration of 10 mg/kg. Control animals received saline alone for the same period. Mice were sacrificed after 8 injections and total RNA was extracted from excised tumor using TRIzol reagent (Gibco-BRL, Gaithersburg MD). Northern blot analysis of R1 nRNA levels was performed as previously described (Hurta and Wright 1994). Glyceraldehyde-3-phosphate dehydrogenase (GADPH) m-RNA levels were probed for RNA loading controls. Two sets of independent experiments are shown. FIG. 20 is an autoradiograph of the norther blot. Marked inhibition of R1 mRNA in tumor tissue was observed following intravenous administration of AS-I-618-20 providing evidence that AS-I-618-20 is reaching the tumor site in vivo and is acting by an antisense mechanism.

Example 13

Comparison of the Antitumor Effects of Various Antisense Sequences.

Human colon carcinoma (HT-29) cells, human melanoma (A2058) cells or human lung carcinoma (H460) cells were removed from culture plates, washed and a 0.1 ml aliquot (range between $10^6$ to $10^7$ cells) was injected subcutaneously into the right flank of female CD-1 nude mice from Charles River, Montreal. Antisense sequences were manufactured as fully phosphorothioated compounds including the following sequences:

| | | |
|---|---|---|
| c-raf | 5'-TCCCGCCTGTGACATGCATT-3' | [SEQ ID NO:216] |
| PKC-alpha | 5'-GTTCTCGCTGGTGAGTTTCA-3' | [SEQ ID NO:218] |
| Bcl-2 | 5'-TCTCCCAGCGTGCGCCAT-3' | [SEQ ID NO:219] |
| c-myc | 5'-AACGTTGAGGGGCAT-3' | [SEQ ID NO:220] |
| c-myb | 5'-TATGCTGTGCCGGGGTCTTCGGGC-3' | [SEQ ID NO:221] |

The antisense oligonucleotides (10 mg/kg) in normal saline was administered by tail vein injections every second day for 2 weeks following detection of a palpable tumor mass. The tumor was removed from the mice approximately 14 days after treatment and the weight of the tumor was measured (e.g. Egan et al., 1987A; Egan et al.,1987B; Damen et al., 1989; Fan et al., 1996A). Significance was determined by comparing tumor weights after treatments with each oligonucleotide with tumor weights of a control saline group.

Figure 21:
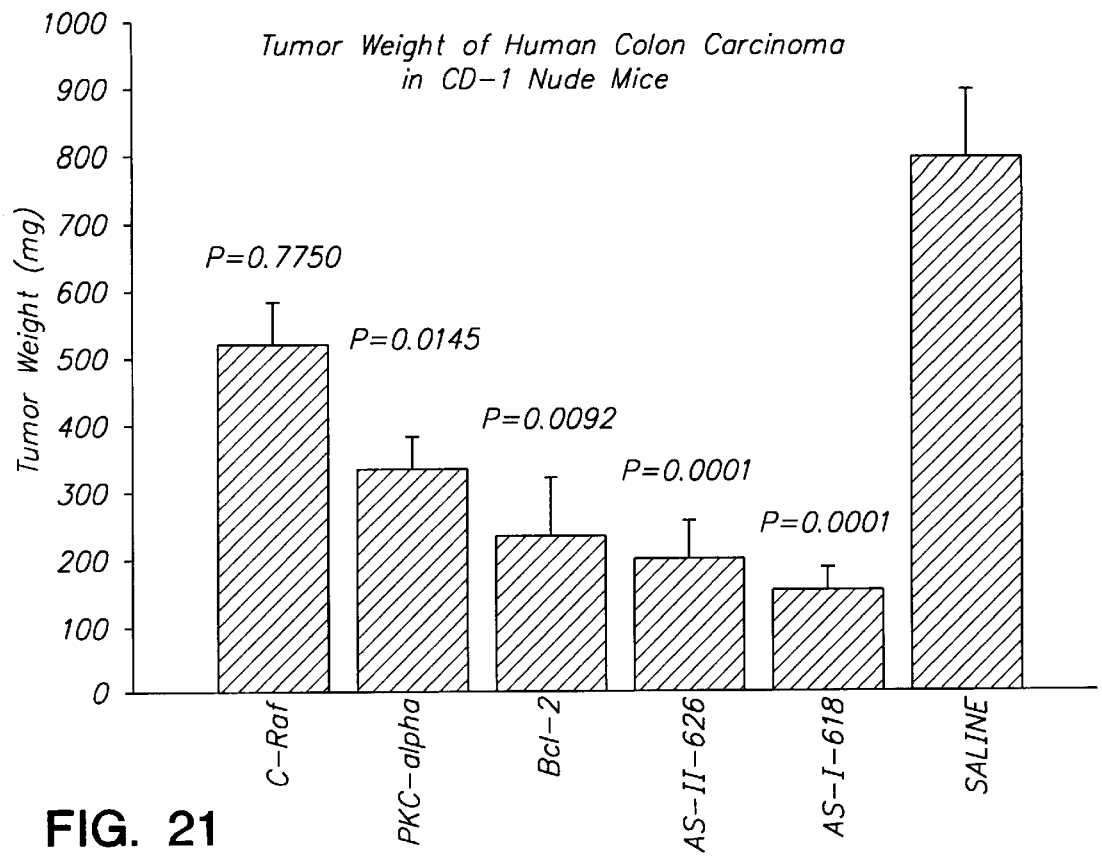
FIG. 21 is a graph showing the weight of human colon carcinoma (HT-29) tumors in CD-1 nude mice after treatment with various antisense oligonucleotides.
Figure 22:
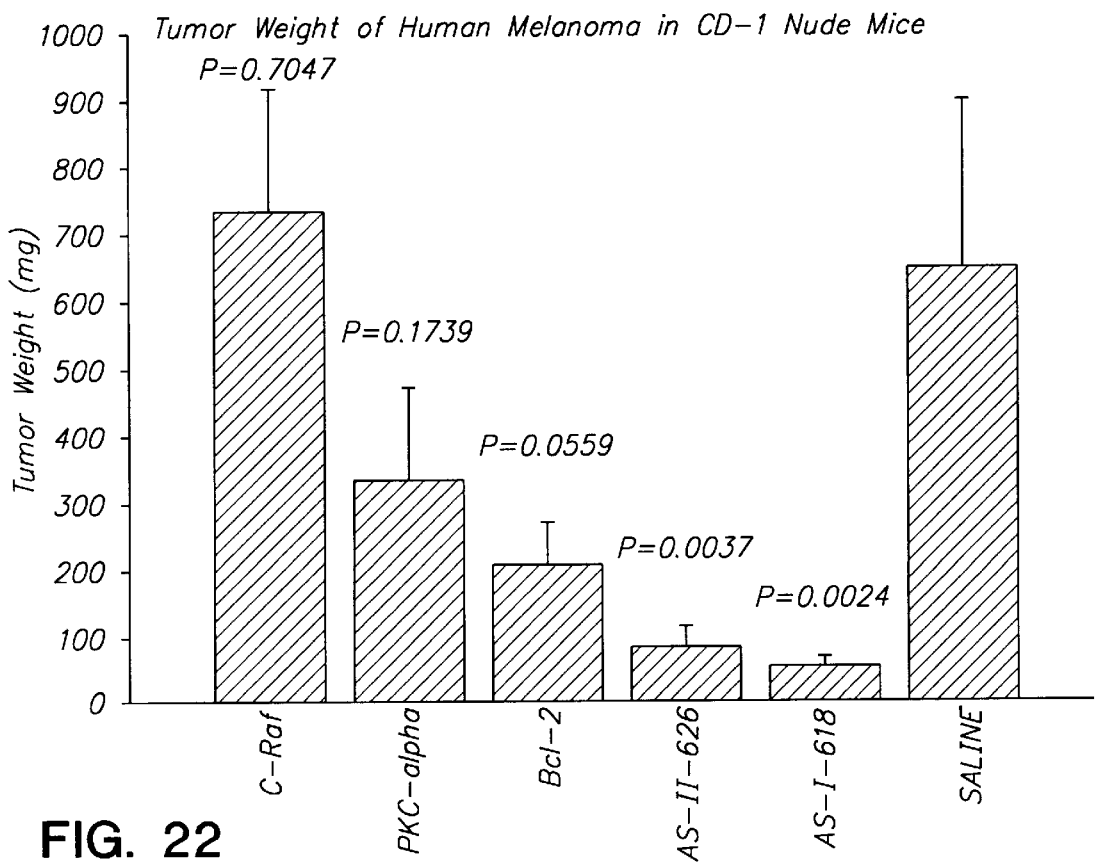
FIG. 22 is a graph showing the weight of human melanoma (A2058) tumors in CD-1 nude mice after treatment with various antisense oligonucleotides.
Figure 23:
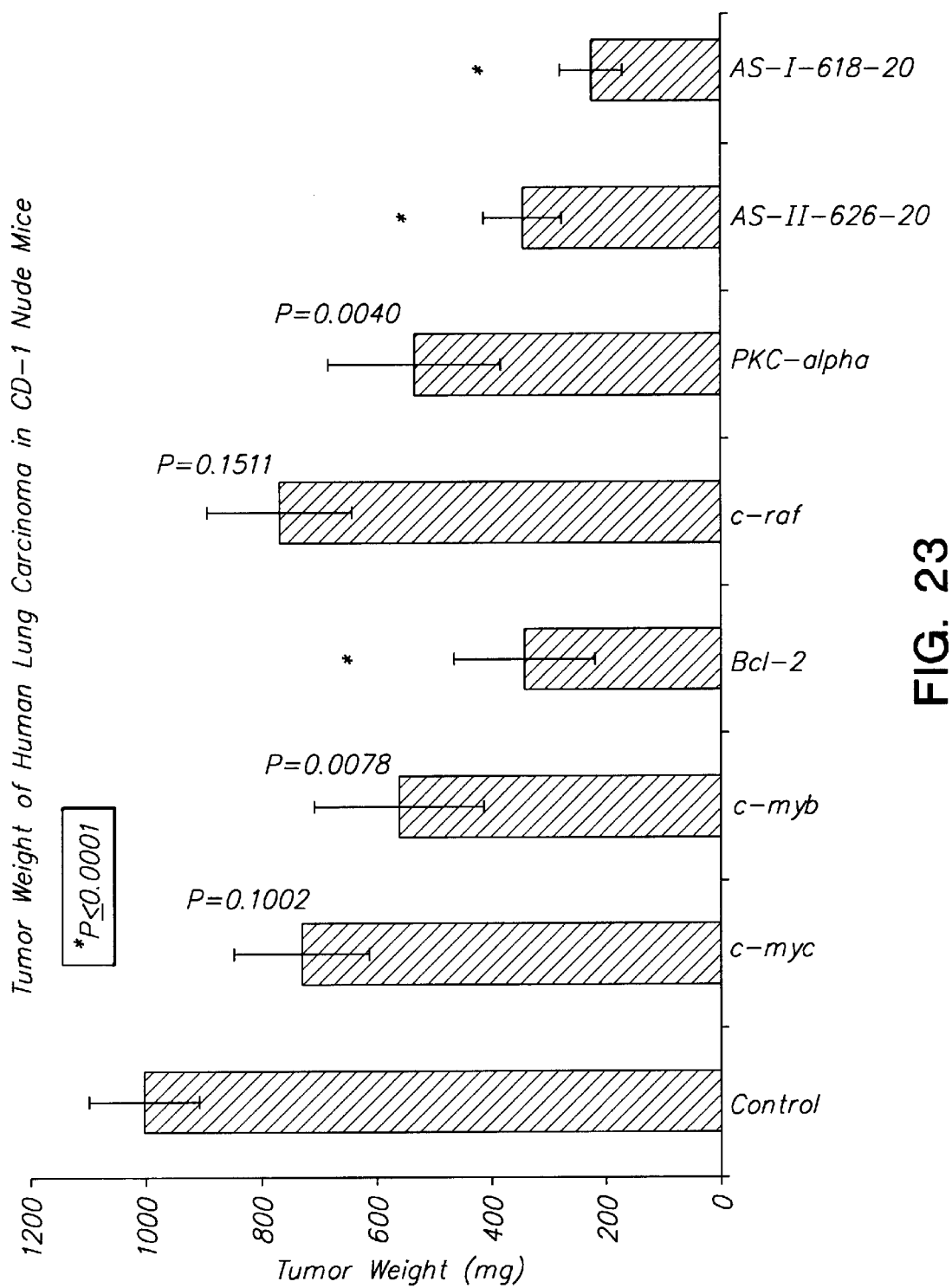
FIG. 23 is a graph showing the weight of human lung carcinoma tumors in CD-1 nude mice after treatment with various antisense oligonucleotides.

FIG. 21 is a graph showing the weight of the tumor from human colon carcinoma (HT-29) cells in CD-1 nude mice treated with the antisense oligonucleotides AS-II-626-20, AS-I-618-20, C-RAF, PKC-alpha and Bcl2. Each result is the average of the results of 5 to 15 mice, with the saline control being the average of 32 mice. FIG. 22 is a graph showing the weight of the tumor from human melanoma (A2058) cells in CD-1 nude mice treated with the same antisense oligonucleotides. Each result is the average of the results of 5 to 10 mice. FIG. 23 is a graph showing the weight of the tumor from human lung carcinoma H460 cells in CD-1 nude mice after treatment with the antisense oligonucleotides AS-II-626-20, AS-I-618-20, C-RAF, PKC-alpha Bcl2, c-myc and c-myb. Each result is the average of the results of 10 to 20 mice.

What is claimed is:

1. An antisense oligonucleotide less than about 50 nucleotides comprising the sequence of AS-I-618-20 (SEQ ID NO:176).

2. The sequence of claim 1 further comprising a reduced dimer formation and reduced self-complementary interactions.

3. A pharmaceutical composition for inhibiting tumor cell growth in a mammal comprising an effective amount of the antisense oligonucleotide less than about 50 nucleotides as set forth in claim 1 and a pharmaceutically acceptable carrier or diluent.

4. A method of inhibiting tumors in a mammal which method comprises contacting the tumor with an effective amount of an antisense oligonucleotide less than about 100 nucleotides comprising the sequence of AS-I-618-20 (SEQ ID NO:176).

5. A method of inhibiting tumors resistant to chemotherapeutic drugs in a mammal which method comprises identifying patients who have tumors that are resistant to a chemotherapeutic drug; and contacting the tumor with the chemotherapeutic drug to which the tumor is resistant and an antisense oligonucleotide less than about 100 nucleotides comprising the sequence of AS-I-618-20 (SEQ ID NO:176)

wherein the amount of the chemotherapeutic drug and the antisense oligonucleotide is sufficient to inhibit tumor cell growth.

6. The method of claim 5 wherein the amount of antisense oligonucleotide in the absence of the chemotherapeutic drug is insufficient to inhibit tumor cell growth.

7. A method of increasing sensitivity of tumors to chemotherapeutic drugs in a mammal by contacting the tumor with an antisense oligonucleotide less than about 100 nucleotides comprising the sequence of AS-I-618-20 (SEQ ID NO:176).

8. The method as set forth in claim 7 wherein the amount of the antisense composition in the absence of the chemotherapeutic drug is insufficient to inhibit tumor cell growth.

9. The method as set forth in claim 7 wherein the amount of the antisense composition in the absence of the chemotherapeutic drug is sufficient to inhibit tumor cell growth.

10. A method of inhibiting metastasis of tumor cells in a mammal which method comprises administering to said mammal an amount sufficient to inhibit tumor cell growth of an antisense oligonucleotide comprising the sequence of AS-I-618-20 (SEQ ID NO:176).

11. An isolated DNA with a sequence comprising a transcriptional initiation region and a sequence encoding an antisense oligonucleotide less than about 50 nucleotides comprising the sequence of AS-I-618-20 SEQ ID NO:176.

* * * * *

SEQUENCE LISTING

```
<160> NUMBER OF SEQ ID NOS: 220

<210> SEQ ID NO 1
<211> LENGTH: 20
<212> TYPE: DNA
<213> ORGANISM: Human

<400> SEQUENCE: 1
tcctggaaga tcctcctcgc                                               20

<210> SEQ ID NO 2
<211> LENGTH: 20
<212> TYPE: DNA
<213> ORGANISM: Human

<400> SEQUENCE: 2
tcccacatat gagaaaactc                                               20

<210> SEQ ID NO 3
<211> LENGTH: 20
<212> TYPE: DNA
<213> ORGANISM: Human

<400> SEQUENCE: 3
acccttccca ttggctgcgc                                               20
```

```
<210> SEQ ID NO 4
<211> LENGTH: 20
<212> TYPE: DNA
<213> ORGANISM: Human
<220> FEATURE:
<221> NAME/KEY: modified_base
<222> LOCATION: (1)..(20)
<223> OTHER INFORMATION: Nucleotides 1&2, 3&4, 7&8, 10&11, 14&15, 16&17
      and 19&20 are attached by phosphorothioate.

<400> SEQUENCE: 4
gcctccgacc cttcccattg                                                       20

<210> SEQ ID NO 5
<211> LENGTH: 20
<212> TYPE: DNA
<213> ORGANISM: Human

<400> SEQUENCE: 5
tgcctccgac ccttcccatt                                                       20

<210> SEQ ID NO 6
<211> LENGTH: 18
<212> TYPE: DNA
<213> ORGANISM: Human

<400> SEQUENCE: 6
tgcctccgac ccttccca                                                         18

<210> SEQ ID NO 7
<211> LENGTH: 20
<212> TYPE: DNA
<213> ORGANISM: Human
<220> FEATURE:
<221> NAME/KEY: modified_base
<222> LOCATION: (1)..(20)
<223> OTHER INFORMATION: Nucleotides 1&2, 4&5, 7&8, 10&11, 13&14, 16&17,
      and 19&20 are attached by phosphorothioate.

<400> SEQUENCE: 7
cgcgcgctcc cggcccttcc                                                       20

<210> SEQ ID NO 8
<211> LENGTH: 20
<212> TYPE: DNA
<213> ORGANISM: Human

<400> SEQUENCE: 8
cgcgcgctcc cggcccttcc                                                       20

<210> SEQ ID NO 9
<211> LENGTH: 14
<212> TYPE: DNA
<213> ORGANISM: Human

<400> SEQUENCE: 9
cgcgctcccg gccc                                                             14

<210> SEQ ID NO 10
<211> LENGTH: 20
<212> TYPE: DNA
<213> ORGANISM: Human
<220> FEATURE:
<221> NAME/KEY: modified_base
<222> LOCATION: (1)..(20)
<223> OTHER INFORMATION: Nucleotides 1&2, 4&5, 8&9, 11&12, 14&15, 17&18,
``` and 19&20 are attached by phosphorothioate.

<400> SEQUENCE: 10 ccccctcactc cagcagcctt                                          20

<210> SEQ ID NO 11
<211> LENGTH: 20
<212> TYPE: DNA
<213> ORGANISM: Human

<400> SEQUENCE: 11
acccctcact ccagcagcct                                           20

<210> SEQ ID NO 12
<211> LENGTH: 20
<212> TYPE: DNA
<213> ORGANISM: Human

<400> SEQUENCE: 12
ggcgacccct cactccagca                                           20

<210> SEQ ID NO 13
<211> LENGTH: 12
<212> TYPE: DNA
<213> ORGANISM: Human

<400> SEQUENCE: 13
gcacgggcga cc                                                   12

<210> SEQ ID NO 14
<211> LENGTH: 20
<212> TYPE: DNA
<213> ORGANISM: Human

<400> SEQUENCE: 14
tgggacaggg tgcacgggcg                                           20

<210> SEQ ID NO 15
<211> LENGTH: 20
<212> TYPE: DNA
<213> ORGANISM: Human

<400> SEQUENCE: 15
gacggctggg acagggtgca                                           20

<210> SEQ ID NO 16
<211> LENGTH: 20
<212> TYPE: DNA
<213> ORGANISM: Human

<400> SEQUENCE: 16
gagcagccag gacaggacgg                                           20

<210> SEQ ID NO 17
<211> LENGTH: 20
<212> TYPE: DNA
<213> ORGANISM: Human
<220> FEATURE:
<221> NAME/KEY: modified_base
<222> LOCATION: (1)..(20)
<223> OTHER INFORMATION: Nucleotides 1&2, 3&4, 6&7, 9&10, 12&13, 15&16,
       and 19&20 are attached by phosphorothioate.

<400> SEQUENCE: 17
gcgaagcaga gcgagcagcc                                                                          20

<210> SEQ ID NO 18
<211> LENGTH: 20
<212> TYPE: DNA
<213> ORGANISM: Human

<400> SEQUENCE: 18
gcagcgaagc agagcgagca                                                                          20

<210> SEQ ID NO 19
<211> LENGTH: 20
<212> TYPE: DNA
<213> ORGANISM: Human

<400> SEQUENCE: 19
gggagagcat agtggaggcg                                                                          20

<210> SEQ ID NO 20
<211> LENGTH: 20
<212> TYPE: DNA
<213> ORGANISM: Human

<400> SEQUENCE: 20
cggagggaga gcatagtgga                                                                          20

<210> SEQ ID NO 21
<211> LENGTH: 20
<212> TYPE: DNA
<213> ORGANISM: Human

<400> SEQUENCE: 21
gcgagcggga cacggaggga                                                                          20

<210> SEQ ID NO 22
<211> LENGTH: 20
<212> TYPE: DNA
<213> ORGANISM: Human

<400> SEQUENCE: 22
cgggtccgtg atgggcgcga                                                                          20

<210> SEQ ID NO 23
<211> LENGTH: 20
<212> TYPE: DNA
<213> ORGANISM: Human

<400> SEQUENCE: 23
agctgctgcg ggtccgtgat                                                                          20

<210> SEQ ID NO 24
<211> LENGTH: 14
<212> TYPE: DNA
<213> ORGANISM: Human

<400> SEQUENCE: 24
ccccttcagc ggcg                                                                                14

<210> SEQ ID NO 25
<211> LENGTH: 20
<212> TYPE: DNA
<213> ORGANISM: Human

<400> SEQUENCE: 25
cggcggcgtg ttctccttgt                    20

<210> SEQ ID NO 26
<211> LENGTH: 12
<212> TYPE: DNA
<213> ORGANISM: Human

<400> SEQUENCE: 26
cggcggcgtg tt                            12

<210> SEQ ID NO 27
<211> LENGTH: 20
<212> TYPE: DNA
<213> ORGANISM: Human

<400> SEQUENCE: 27
tcctcgcggt cttgctggcc                    20

<210> SEQ ID NO 28
<211> LENGTH: 20
<212> TYPE: DNA
<213> ORGANISM: Human

<400> SEQUENCE: 28
ccgtgggctc ctggaagatc                    20

<210> SEQ ID NO 29
<211> LENGTH: 20
<212> TYPE: DNA
<213> ORGANISM: Human

<400> SEQUENCE: 29
ctgctttagt tttcggctcc                    20

<210> SEQ ID NO 30
<211> LENGTH: 17
<212> TYPE: DNA
<213> ORGANISM: Human

<400> SEQUENCE: 30
cggctcatcc tccacgc                       17

<210> SEQ ID NO 31
<211> LENGTH: 20
<212> TYPE: DNA
<213> ORGANISM: Human

<400> SEQUENCE: 31
ggttttctct cagcagcggc                    20

<210> SEQ ID NO 32
<211> LENGTH: 20
<212> TYPE: DNA
<213> ORGANISM: Human

<400> SEQUENCE: 32
gcggcggggg ttttctctca                    20

<210> SEQ ID NO 33
<211> LENGTH: 20
<212> TYPE: DNA
<213> ORGANISM: Human

-continued

```
<400> SEQUENCE: 33
aagcggcggg ggttttctct                                                20

<210> SEQ ID NO 34
<211> LENGTH: 20
<212> TYPE: DNA
<213> ORGANISM: Human

<400> SEQUENCE: 34
ggaagatgac aaagcggcgg                                                20

<210> SEQ ID NO 35
<211> LENGTH: 20
<212> TYPE: DNA
<213> ORGANISM: Human

<400> SEQUENCE: 35
atggtactcg atggggaaga                                                20

<210> SEQ ID NO 36
<211> LENGTH: 20
<212> TYPE: DNA
<213> ORGANISM: Human

<400> SEQUENCE: 36
agcctctgcc ttcttataca                                                20

<210> SEQ ID NO 37
<211> LENGTH: 20
<212> TYPE: DNA
<213> ORGANISM: Human

<400> SEQUENCE: 37
cctcctcggc ggtccaaaag                                                20

<210> SEQ ID NO 38
<211> LENGTH: 16
<212> TYPE: DNA
<213> ORGANISM: Human

<400> SEQUENCE: 38
tcctcggcgg tccaaa                                                    16

<210> SEQ ID NO 39
<211> LENGTH: 20
<212> TYPE: DNA
<213> ORGANISM: Human

<400> SEQUENCE: 39
tatctctcct cgggtttcag                                                20

<210> SEQ ID NO 40
<211> LENGTH: 20
<212> TYPE: DNA
<213> ORGANISM: Human

<400> SEQUENCE: 40
gcaaagaaag ccagaacatg                                                20

<210> SEQ ID NO 41
<211> LENGTH: 20
<212> TYPE: DNA
<213> ORGANISM: Human
```

<400> SEQUENCE: 41
tcgctccacc aagtttcat                                              20

<210> SEQ ID NO 42
<211> LENGTH: 20
<212> TYPE: DNA
<213> ORGANISM: Human

<400> SEQUENCE: 42
ggctaaatcg ctccaccaag                                             20

<210> SEQ ID NO 43
<211> LENGTH: 20
<212> TYPE: DNA
<213> ORGANISM: Human

<400> SEQUENCE: 43
aacttcttgg ctaaatcgct                                             20

<210> SEQ ID NO 44
<211> LENGTH: 20
<212> TYPE: DNA
<213> ORGANISM: Human

<400> SEQUENCE: 44
gaagccatag aaacagcggg                                             20

<210> SEQ ID NO 45
<211> LENGTH: 20
<212> TYPE: DNA
<213> ORGANISM: Human

<400> SEQUENCE: 45
gacacaaggc atcgtttcaa                                             20

<210> SEQ ID NO 46
<211> LENGTH: 20
<212> TYPE: DNA
<213> ORGANISM: Human

<400> SEQUENCE: 46
tctgccttct tcttgacaca                                             20

<210> SEQ ID NO 47
<211> LENGTH: 20
<212> TYPE: DNA
<213> ORGANISM: Human

<400> SEQUENCE: 47
atccagcgca aggcccagtc                                             20

<210> SEQ ID NO 48
<211> LENGTH: 20
<212> TYPE: DNA
<213> ORGANISM: Human

<400> SEQUENCE: 48
gcaaaggcta caacacgttc                                             20

<210> SEQ ID NO 49
<211> LENGTH: 20
<212> TYPE: DNA

<213> ORGANISM: Human

<400> SEQUENCE: 49
aaccggaaaa gaaaatgcct					20

<210> SEQ ID NO 50
<211> LENGTH: 20
<212> TYPE: DNA
<213> ORGANISM: Human

<400> SEQUENCE: 50
cagaatatcg acgcaaaaga					20

<210> SEQ ID NO 51
<211> LENGTH: 20
<212> TYPE: DNA
<213> ORGANISM: Human

<400> SEQUENCE: 51
ggcatcagtc ctcgtttctt					20

<210> SEQ ID NO 52
<211> LENGTH: 20
<212> TYPE: DNA
<213> ORGANISM: Human

<400> SEQUENCE: 52
tgtaaaccct catctctgct					20

<210> SEQ ID NO 53
<211> LENGTH: 20
<212> TYPE: DNA
<213> ORGANISM: Human

<400> SEQUENCE: 53
tcaggcaagc aaaatcacag					20

<210> SEQ ID NO 54
<211> LENGTH: 20
<212> TYPE: DNA
<213> ORGANISM: Human

<400> SEQUENCE: 54
gaacatcagg caagcaaaat					20

<210> SEQ ID NO 55
<211> LENGTH: 20
<212> TYPE: DNA
<213> ORGANISM: Human

<400> SEQUENCE: 55
ttgtgtacca ggtgtttgaa					20

<210> SEQ ID NO 56
<211> LENGTH: 20
<212> TYPE: DNA
<213> ORGANISM: Human

<400> SEQUENCE: 56
ctctctcctc cgatggtttg					20

<210> SEQ ID NO 57
<211> LENGTH: 20

```
<212> TYPE: DNA
<213> ORGANISM: Human

<400> SEQUENCE: 57
ttctcttact ctctcctccg                                              20

<210> SEQ ID NO 58
<211> LENGTH: 20
<212> TYPE: DNA
<213> ORGANISM: Human

<400> SEQUENCE: 58
gtattgcttc attagagtgc                                              20

<210> SEQ ID NO 59
<211> LENGTH: 20
<212> TYPE: DNA
<213> ORGANISM: Human

<400> SEQUENCE: 59
cccagttcca gcataagtct                                              20

<210> SEQ ID NO 60
<211> LENGTH: 20
<212> TYPE: DNA
<213> ORGANISM: Human

<400> SEQUENCE: 60
aaaaccttgc taaaacccag                                              20

<210> SEQ ID NO 61
<211> LENGTH: 20
<212> TYPE: DNA
<213> ORGANISM: Human

<400> SEQUENCE: 61
caaatgggtt ctctactctg                                              20

<210> SEQ ID NO 62
<211> LENGTH: 20
<212> TYPE: DNA
<213> ORGANISM: Human

<400> SEQUENCE: 62
ataaagtcaa atgggttctc                                              20

<210> SEQ ID NO 63
<211> LENGTH: 20
<212> TYPE: DNA
<213> ORGANISM: Human

<400> SEQUENCE: 63
ttagtctttc cttccagtga                                              20

<210> SEQ ID NO 64
<211> LENGTH: 20
<212> TYPE: DNA
<213> ORGANISM: Human

<400> SEQUENCE: 64
tcgcctactc tcttctcaaa                                              20

<210> SEQ ID NO 65
```

-continued

<211> LENGTH: 20
<212> TYPE: DNA
<213> ORGANISM: Human

<400> SEQUENCE: 65
cctctgatac tcgcctactc                                                   20

<210> SEQ ID NO 66
<211> LENGTH: 20
<212> TYPE: DNA
<213> ORGANISM: Human

<400> SEQUENCE: 66
gacatcactc ccatcctctg                                                   20

<210> SEQ ID NO 67
<211> LENGTH: 20
<212> TYPE: DNA
<213> ORGANISM: Human

<400> SEQUENCE: 67
gcatccaagg taaaagaatt                                                   20

<210> SEQ ID NO 68
<211> LENGTH: 20
<212> TYPE: DNA
<213> ORGANISM: Human

<400> SEQUENCE: 68
tcagcatcca aggtaaaaga                                                   20

<210> SEQ ID NO 69
<211> LENGTH: 20
<212> TYPE: DNA
<213> ORGANISM: Human

<400> SEQUENCE: 69
gaagtcagca tccaaggtaa                                                   20

<210> SEQ ID NO 70
<211> LENGTH: 20
<212> TYPE: DNA
<213> ORGANISM: Human

<400> SEQUENCE: 70
ttagaagtca gcatccaagg                                                   20

<210> SEQ ID NO 71
<211> LENGTH: 20
<212> TYPE: DNA
<213> ORGANISM: Human

<400> SEQUENCE: 71
gcacatcttc agttcattta                                                   20

<210> SEQ ID NO 72
<211> LENGTH: 20
<212> TYPE: DNA
<213> ORGANISM: Human

<400> SEQUENCE: 72
gggcacatct tcagttcatt                                                   20

-continued

```
<210> SEQ ID NO 73
<211> LENGTH: 20
<212> TYPE: DNA
<213> ORGANISM: Human

<400> SEQUENCE: 73
aaaaatcagc caagtaaggg                                                      20

<210> SEQ ID NO 74
<211> LENGTH: 20
<212> TYPE: DNA
<213> ORGANISM: Human

<400> SEQUENCE: 74
atggaaaaaa aaaatcagcc                                                      20

<210> SEQ ID NO 75
<211> LENGTH: 20
<212> TYPE: DNA
<213> ORGANISM: Human

<400> SEQUENCE: 75
ttcatggtgt ggctagttgg                                                      20

<210> SEQ ID NO 76
<211> LENGTH: 20
<212> TYPE: DNA
<213> ORGANISM: Human

<400> SEQUENCE: 76
aggactggtt gtgaggtagc                                                      20

<210> SEQ ID NO 77
<211> LENGTH: 20
<212> TYPE: DNA
<213> ORGANISM: Human

<400> SEQUENCE: 77
ccagcactat aaacagacag                                                      20

<210> SEQ ID NO 78
<211> LENGTH: 20
<212> TYPE: DNA
<213> ORGANISM: Human

<400> SEQUENCE: 78
ttctggcaaa aggtgatact                                                      20

<210> SEQ ID NO 79
<211> LENGTH: 20
<212> TYPE: DNA
<213> ORGANISM: Human

<400> SEQUENCE: 79
gtaagtcaca gccagccagg                                                      20

<210> SEQ ID NO 80
<211> LENGTH: 20
<212> TYPE: DNA
<213> ORGANISM: Human

<400> SEQUENCE: 80
actgccattg tcactgctat                                                      20
```

-continued

```
<210> SEQ ID NO 81
<211> LENGTH: 20
<212> TYPE: DNA
<213> ORGANISM: Human

<400> SEQUENCE: 81
tggctgtgct ggttaaagga                                              20

<210> SEQ ID NO 82
<211> LENGTH: 20
<212> TYPE: DNA
<213> ORGANISM: Human

<400> SEQUENCE: 82
ttttaactgg ctgtgctggt                                              20

<210> SEQ ID NO 83
<211> LENGTH: 20
<212> TYPE: DNA
<213> ORGANISM: Human

<400> SEQUENCE: 83
attaaaatct gcgttgaagc                                              20

<210> SEQ ID NO 84
<211> LENGTH: 20
<212> TYPE: DNA
<213> ORGANISM: Human

<400> SEQUENCE: 84
tatcgccgcc gtgagtacaa                                              20

<210> SEQ ID NO 85
<211> LENGTH: 20
<212> TYPE: DNA
<213> ORGANISM: Human

<400> SEQUENCE: 85
gctattatcg ccgccgtgag                                              20

<210> SEQ ID NO 86
<211> LENGTH: 12
<212> TYPE: DNA
<213> ORGANISM: Human

<400> SEQUENCE: 86
atcgccgccg tg                                                      12

<210> SEQ ID NO 87
<211> LENGTH: 20
<212> TYPE: DNA
<213> ORGANISM: Human

<400> SEQUENCE: 87
gaaaccaaat aaatcaagct                                              20

<210> SEQ ID NO 88
<211> LENGTH: 20
<212> TYPE: DNA
<213> ORGANISM: Human

<400> SEQUENCE: 88
ttagtggtca ggagaatgta                                              20
```

```
<210> SEQ ID NO 89
<211> LENGTH: 20
<212> TYPE: DNA
<213> ORGANISM: Human

<400> SEQUENCE: 89
tggcaccaac tgactaatat                                                    20

<210> SEQ ID NO 90
<211> LENGTH: 20
<212> TYPE: DNA
<213> ORGANISM: Human

<400> SEQUENCE: 90
cctgtcttct atctggcacc                                                    20

<210> SEQ ID NO 91
<211> LENGTH: 20
<212> TYPE: DNA
<213> ORGANISM: Human

<400> SEQUENCE: 91
gccacaggat aaaaacacaa                                                    20

<210> SEQ ID NO 92
<211> LENGTH: 20
<212> TYPE: DNA
<213> ORGANISM: Human

<400> SEQUENCE: 92
cccaggacac tacacaagcc                                                    20

<210> SEQ ID NO 93
<211> LENGTH: 20
<212> TYPE: DNA
<213> ORGANISM: Human

<400> SEQUENCE: 93
tcagaggggg cagagaatcc                                                    20

<210> SEQ ID NO 94
<211> LENGTH: 20
<212> TYPE: DNA
<213> ORGANISM: Human

<400> SEQUENCE: 94
tcctttatcc cacaacactc                                                    20

<210> SEQ ID NO 95
<211> LENGTH: 20
<212> TYPE: DNA
<213> ORGANISM: Human

<400> SEQUENCE: 95
ccttgccctg agagattcct                                                    20

<210> SEQ ID NO 96
<211> LENGTH: 20
<212> TYPE: DNA
<213> ORGANISM: Human
<220> FEATURE:
<221> NAME/KEY: modified_base
<222> LOCATION: (1)..(20)
```

<223> OTHER INFORMATION: Nucleotides 1&2, 3&4, 5&6, 7&8, 9&10, 11&12, 13&14, 15&16, 17&18, and 19&20 are attached by phosphorothioate.

<400> SEQUENCE: 96
ccttgccctg agagattcct        20

<210> SEQ ID NO 97
<211> LENGTH: 20
<212> TYPE: DNA
<213> ORGANISM: Human

<400> SEQUENCE: 97
ggcccagatc acccctaaat        20

<210> SEQ ID NO 98
<211> LENGTH: 20
<212> TYPE: DNA
<213> ORGANISM: Human

<400> SEQUENCE: 98
aaacggcttc tcacacatat        20

<210> SEQ ID NO 99
<211> LENGTH: 20
<212> TYPE: DNA
<213> ORGANISM: Human

<400> SEQUENCE: 99
gagaaataaa atgaaacggc        20

<210> SEQ ID NO 100
<211> LENGTH: 20
<212> TYPE: DNA
<213> ORGANISM: Human

<400> SEQUENCE: 100
cgttgaggaa aatacagtga        20

<210> SEQ ID NO 101
<211> LENGTH: 20
<212> TYPE: DNA
<213> ORGANISM: Human

<400> SEQUENCE: 101
gctcccacat atgaaaactc        20

<210> SEQ ID NO 102
<211> LENGTH: 20
<212> TYPE: DNA
<213> ORGANISM: Human

<400> SEQUENCE: 102
cacacaacct acttacacca        20

<210> SEQ ID NO 103
<211> LENGTH: 20
<212> TYPE: DNA
<213> ORGANISM: Human

<400> SEQUENCE: 103
acaggaatct ttgtagagca        20

-continued

```
<210> SEQ ID NO 104
<211> LENGTH: 20
<212> TYPE: DNA
<213> ORGANISM: Human

<400> SEQUENCE: 104
gttccagcca gacagcactt                                               20

<210> SEQ ID NO 105
<211> LENGTH: 20
<212> TYPE: DNA
<213> ORGANISM: Human

<400> SEQUENCE: 105
gagttccagc cagacagcac                                               20

<210> SEQ ID NO 106
<211> LENGTH: 20
<212> TYPE: DNA
<213> ORGANISM: Human

<400> SEQUENCE: 106
cagagtggga agggttaggt                                               20

<210> SEQ ID NO 107
<211> LENGTH: 20
<212> TYPE: DNA
<213> ORGANISM: Human

<400> SEQUENCE: 107
aggtgacaga gtgggaaggg                                               20

<210> SEQ ID NO 108
<211> LENGTH: 20
<212> TYPE: DNA
<213> ORGANISM: Human

<400> SEQUENCE: 108
gactggactg cggctctaaa                                               20

<210> SEQ ID NO 109
<211> LENGTH: 20
<212> TYPE: DNA
<213> ORGANISM: Human

<400> SEQUENCE: 109
atgactcgtt cttggcggcc                                               20

<210> SEQ ID NO 110
<211> LENGTH: 20
<212> TYPE: DNA
<213> ORGANISM: Human

<400> SEQUENCE: 110
caaagcttct ggattcgaga                                               20

<210> SEQ ID NO 111
<211> LENGTH: 20
<212> TYPE: DNA
<213> ORGANISM: Human

<400> SEQUENCE: 111
ttcatggtga tctgagcagg                                               20
```

<210> SEQ ID NO 112
<211> LENGTH: 20
<212> TYPE: DNA
<213> ORGANISM: Human

<400> SEQUENCE: 112
gccttggatt actttcatgg                                           20

<210> SEQ ID NO 113
<211> LENGTH: 20
<212> TYPE: DNA
<213> ORGANISM: Human

<400> SEQUENCE: 113
ttcagcagcc aaagtatcta                                           20

<210> SEQ ID NO 114
<211> LENGTH: 20
<212> TYPE: DNA
<213> ORGANISM: Human

<400> SEQUENCE: 114
gccaggatag catagtcagg                                           20

<210> SEQ ID NO 115
<211> LENGTH: 20
<212> TYPE: DNA
<213> ORGANISM: Human

<400> SEQUENCE: 115
ctttctttgt ttctttgtgc                                           20

<210> SEQ ID NO 116
<211> LENGTH: 20
<212> TYPE: DNA
<213> ORGANISM: Human

<400> SEQUENCE: 116
gggagagtgt ttgccattat                                           20

<210> SEQ ID NO 117
<211> LENGTH: 20
<212> TYPE: DNA
<213> ORGANISM: Human

<400> SEQUENCE: 117
ttgacttggc caccatggga                                           20

<210> SEQ ID NO 118
<211> LENGTH: 20
<212> TYPE: DNA
<213> ORGANISM: Human

<400> SEQUENCE: 118
ggccagaaca atatccaatg                                           20

<210> SEQ ID NO 119
<211> LENGTH: 20
<212> TYPE: DNA
<213> ORGANISM: Human

<400> SEQUENCE: 119
tcaggcgatc tttattggcc                                           20

-continued

```
<210> SEQ ID NO 120
<211> LENGTH: 20
<212> TYPE: DNA
<213> ORGANISM: Human

<400> SEQUENCE: 120
ttcaacaaat aagaccgctc                                                      20

<210> SEQ ID NO 121
<211> LENGTH: 20
<212> TYPE: DNA
<213> ORGANISM: Human

<400> SEQUENCE: 121
tttcagccac ttttccattg                                                      20

<210> SEQ ID NO 122
<211> LENGTH: 20
<212> TYPE: DNA
<213> ORGANISM: Human

<400> SEQUENCE: 122
ggtctttcag ccacttttcc                                                      20

<210> SEQ ID NO 123
<211> LENGTH: 20
<212> TYPE: DNA
<213> ORGANISM: Human

<400> SEQUENCE: 123
ttgaagagag tgggcgaagc                                                      20

<210> SEQ ID NO 124
<211> LENGTH: 20
<212> TYPE: DNA
<213> ORGANISM: Human

<400> SEQUENCE: 124
agcattgaag agagtgggcg                                                      20

<210> SEQ ID NO 125
<211> LENGTH: 20
<212> TYPE: DNA
<213> ORGANISM: Human

<400> SEQUENCE: 125
gaaagttgcg ggcggttggt                                                      20

<210> SEQ ID NO 126
<211> LENGTH: 20
<212> TYPE: DNA
<213> ORGANISM: Human

<400> SEQUENCE: 126
gctgtcatct ttcatactca                                                      20

<210> SEQ ID NO 127
<211> LENGTH: 20
<212> TYPE: DNA
<213> ORGANISM: Human

<400> SEQUENCE: 127
```

-continued ccaattcctc cagcagactt                                                    20

<210> SEQ ID NO 128
<211> LENGTH: 20
<212> TYPE: DNA
<213> ORGANISM: Human

<400> SEQUENCE: 128
caactcacag caacaccaat                                                    20

<210> SEQ ID NO 129
<211> LENGTH: 20
<212> TYPE: DNA
<213> ORGANISM: Human

<400> SEQUENCE: 129
gcccgaatac aactcacagc                                                    20

<210> SEQ ID NO 130
<211> LENGTH: 20
<212> TYPE: DNA
<213> ORGANISM: Human

<400> SEQUENCE: 130
aattgccatt agtcccagca                                                    20

<210> SEQ ID NO 131
<211> LENGTH: 20
<212> TYPE: DNA
<213> ORGANISM: Human

<400> SEQUENCE: 131
atgccccagg acgcttgttc                                                    20

<210> SEQ ID NO 132
<211> LENGTH: 20
<212> TYPE: DNA
<213> ORGANISM: Human

<400> SEQUENCE: 132
ccaaggctcc aggtaaatag                                                    20

<210> SEQ ID NO 133
<211> LENGTH: 20
<212> TYPE: DNA
<213> ORGANISM: Human

<400> SEQUENCE: 133
acgctgctct tcctttcctg                                                    20

<210> SEQ ID NO 134
<211> LENGTH: 20
<212> TYPE: DNA
<213> ORGANISM: Human

<400> SEQUENCE: 134
tccaaagagc aaagaaaaga                                                    20

<210> SEQ ID NO 135
<211> LENGTH: 20
<212> TYPE: DNA
<213> ORGANISM: Human

<400> SEQUENCE: 135
cctctcccca aacctcatcc                                            20

<210> SEQ ID NO 136
<211> LENGTH: 20
<212> TYPE: DNA
<213> ORGANISM: Human

<400> SEQUENCE: 136
aactttgcgg acacgacctt                                            20

<210> SEQ ID NO 137
<211> LENGTH: 20
<212> TYPE: DNA
<213> ORGANISM: Human

<400> SEQUENCE: 137
ggggtgcctg tttccgtctg                                            20

<210> SEQ ID NO 138
<211> LENGTH: 20
<212> TYPE: DNA
<213> ORGANISM: Human

<400> SEQUENCE: 138
ttctgctggt tgctctttcg                                            20

<210> SEQ ID NO 139
<211> LENGTH: 20
<212> TYPE: DNA
<213> ORGANISM: Human

<400> SEQUENCE: 139
aggttctgct ggttgctctt                                            20

<210> SEQ ID NO 140
<211> LENGTH: 20
<212> TYPE: DNA
<213> ORGANISM: Human

<400> SEQUENCE: 140
gggccaggga agccaaatta                                            20

<210> SEQ ID NO 141
<211> LENGTH: 20
<212> TYPE: DNA
<213> ORGANISM: Human

<400> SEQUENCE: 141
ggggcgatgg cgtttatttg                                            20

<210> SEQ ID NO 142
<211> LENGTH: 20
<212> TYPE: DNA
<213> ORGANISM: Human

<400> SEQUENCE: 142
caatggggcg atggcgttta                                            20

<210> SEQ ID NO 143
<211> LENGTH: 20
<212> TYPE: DNA
<213> ORGANISM: Human

-continued

<400> SEQUENCE: 143
ttccagagca ccataataaa 20

<210> SEQ ID NO 144
<211> LENGTH: 20
<212> TYPE: DNA
<213> ORGANISM: Human

<400> SEQUENCE: 144
tgggccctgc tccttggcaa 20

<210> SEQ ID NO 145
<211> LENGTH: 20
<212> TYPE: DNA
<213> ORGANISM: Human

<400> SEQUENCE: 145
ggcatcgggg caataagtaa 20

<210> SEQ ID NO 146
<211> LENGTH: 20
<212> TYPE: DNA
<213> ORGANISM: Human

<400> SEQUENCE: 146
gctgtaggca tcgggcaat 20

<210> SEQ ID NO 147
<211> LENGTH: 20
<212> TYPE: DNA
<213> ORGANISM: Human

<400> SEQUENCE: 147
catgccatag gccccgctcg 20

<210> SEQ ID NO 148
<211> LENGTH: 20
<212> TYPE: DNA
<213> ORGANISM: Human

<400> SEQUENCE: 148
agttgcttca ggtcatcagg 20

<210> SEQ ID NO 149
<211> LENGTH: 20
<212> TYPE: DNA
<213> ORGANISM: Human

<400> SEQUENCE: 149
cagctgccat cttgagaaca 20

<210> SEQ ID NO 150
<211> LENGTH: 20
<212> TYPE: DNA
<213> ORGANISM: Human

<400> SEQUENCE: 150
ctcagcaatg tggatgttca 20

<210> SEQ ID NO 151
<211> LENGTH: 20
<212> TYPE: DNA
<213> ORGANISM: Human

<400> SEQUENCE: 151
agtcttcaaa ccctgcttcc                                                     20

<210> SEQ ID NO 152
<211> LENGTH: 20
<212> TYPE: DNA
<213> ORGANISM: Human

<400> SEQUENCE: 152
catcccagtc ttcaaaccct                                                     20

<210> SEQ ID NO 153
<211> LENGTH: 20
<212> TYPE: DNA
<213> ORGANISM: Human

<400> SEQUENCE: 153
gtgaactgga ttggattagc                                                     20

<210> SEQ ID NO 154
<211> LENGTH: 20
<212> TYPE: DNA
<213> ORGANISM: Human

<400> SEQUENCE: 154
tggctgctgt gttcctctcc                                                     20

<210> SEQ ID NO 155
<211> LENGTH: 20
<212> TYPE: DNA
<213> ORGANISM: Human

<400> SEQUENCE: 155
cttccaagtc tttcctcagg                                                     20

<210> SEQ ID NO 156
<211> LENGTH: 20
<212> TYPE: DNA
<213> ORGANISM: Human

<400> SEQUENCE: 156
taccacctca agcaaaccca                                                     20

<210> SEQ ID NO 157
<211> LENGTH: 20
<212> TYPE: DNA
<213> ORGANISM: Human

<400> SEQUENCE: 157
caacagggtc cagcaaagcc                                                     20

<210> SEQ ID NO 158
<211> LENGTH: 20
<212> TYPE: DNA
<213> ORGANISM: Human

<400> SEQUENCE: 158
tccgtttttt ttttctttt                                                      20

<210> SEQ ID NO 159
<211> LENGTH: 20
<212> TYPE: DNA

-continued

<213> ORGANISM: Human

<400> SEQUENCE: 159
tgctaaatgg gtgatgaaac                                               20

<210> SEQ ID NO 160
<211> LENGTH: 20
<212> TYPE: DNA
<213> ORGANISM: Human

<400> SEQUENCE: 160
cccaccagtc aaagcagtaa                                               20

<210> SEQ ID NO 161
<211> LENGTH: 20
<212> TYPE: DNA
<213> ORGANISM: Human

<400> SEQUENCE: 161
ctcaagaagt agtttggcta                                               20

<210> SEQ ID NO 162
<211> LENGTH: 20
<212> TYPE: DNA
<213> ORGANISM: Human

<400> SEQUENCE: 162
ggacatgccc gggcatgtcc                                               20

<210> SEQ ID NO 163
<211> LENGTH: 20
<212> TYPE: DNA
<213> ORGANISM: Human

<400> SEQUENCE: 163
ggctaaactg ctccaccaag                                               20

<210> SEQ ID NO 164
<211> LENGTH: 20
<212> TYPE: DNA
<213> ORGANISM: Human

<400> SEQUENCE: 164
acgcactcag ctagtgacac                                               20

<210> SEQ ID NO 165
<211> LENGTH: 20
<212> TYPE: DNA
<213> ORGANISM: Human

<400> SEQUENCE: 165
aggcgcaaca atccaaatcc                                               20

<210> SEQ ID NO 166
<211> LENGTH: 20
<212> TYPE: DNA
<213> ORGANISM: Human

<400> SEQUENCE: 166
actttcttca gagcagaggc                                               20

<210> SEQ ID NO 167
<211> LENGTH: 20

```
<212> TYPE: DNA
<213> ORGANISM: Human

<400> SEQUENCE: 167
gctcagggga aagaactgga                                              20

<210> SEQ ID NO 168
<211> LENGTH: 20
<212> TYPE: DNA
<213> ORGANISM: Human

<400> SEQUENCE: 168
ggttaggttc caggcgttgc                                              20

<210> SEQ ID NO 169
<211> LENGTH: 20
<212> TYPE: DNA
<213> ORGANISM: Human

<400> SEQUENCE: 169
gctagtggct gaggctctga                                              20

<210> SEQ ID NO 170
<211> LENGTH: 20
<212> TYPE: DNA
<213> ORGANISM: Human

<400> SEQUENCE: 170
agttccactg tggtgacccc                                              20

<210> SEQ ID NO 171
<211> LENGTH: 20
<212> TYPE: DNA
<213> ORGANISM: Human

<400> SEQUENCE: 171
agggtgctta gtagtcaagg                                              20

<210> SEQ ID NO 172
<211> LENGTH: 20
<212> TYPE: DNA
<213> ORGANISM: Human

<400> SEQUENCE: 172
caagttagag acagcgatcc                                              20

<210> SEQ ID NO 173
<211> LENGTH: 20
<212> TYPE: DNA
<213> ORGANISM: Human

<400> SEQUENCE: 173
gccattatgt ggatttatgt                                              20

<210> SEQ ID NO 174
<211> LENGTH: 20
<212> TYPE: DNA
<213> ORGANISM: Human

<400> SEQUENCE: 174
cggtcataga taatagcaga                                              20

<210> SEQ ID NO 175
```

-continued

```
<211> LENGTH: 20
<212> TYPE: DNA
<213> ORGANISM: Human

<400> SEQUENCE: 175
gccgaagtaa ttgtaagaga                                              20

<210> SEQ ID NO 176
<211> LENGTH: 20
<212> TYPE: DNA
<213> ORGANISM: Human

<400> SEQUENCE: 176
ctctagcgtc ttaaagccga                                              20

<210> SEQ ID NO 177
<211> LENGTH: 20
<212> TYPE: DNA
<213> ORGANISM: Human

<400> SEQUENCE: 177
tgctgcatca atgtcttctt                                              20

<210> SEQ ID NO 178
<211> LENGTH: 20
<212> TYPE: DNA
<213> ORGANISM: Human

<400> SEQUENCE: 178
gtaaaccacc tctcagaaag                                              20

<210> SEQ ID NO 179
<211> LENGTH: 20
<212> TYPE: DNA
<213> ORGANISM: Human

<400> SEQUENCE: 179
aaagttgcgg gcggttggta                                              20

<210> SEQ ID NO 180
<211> LENGTH: 20
<212> TYPE: DNA
<213> ORGANISM: Human

<400> SEQUENCE: 180
gtgtcataaa tgccttcaat                                              20

<210> SEQ ID NO 181
<211> LENGTH: 20
<212> TYPE: DNA
<213> ORGANISM: Human

<400> SEQUENCE: 181
ctgccagtag cccgaataca                                              20

<210> SEQ ID NO 182
<211> LENGTH: 20
<212> TYPE: DNA
<213> ORGANISM: Human

<400> SEQUENCE: 182
tactctcagc atcggtacaa                                              20
```

<210> SEQ ID NO 183
<211> LENGTH: 20
<212> TYPE: DNA
<213> ORGANISM: Human

<400> SEQUENCE: 183
tagcaaatgc cccaggacgc                                               20

<210> SEQ ID NO 184
<211> LENGTH: 20
<212> TYPE: DNA
<213> ORGANISM: Human

<400> SEQUENCE: 184
gtctaaatgc caaggctcca                                               20

<210> SEQ ID NO 185
<211> LENGTH: 20
<212> TYPE: DNA
<213> ORGANISM: Human

<400> SEQUENCE: 185
cacgctgctc ttcctttcct                                               20

<210> SEQ ID NO 186
<211> LENGTH: 20
<212> TYPE: DNA
<213> ORGANISM: Human

<400> SEQUENCE: 186
ccaggacact catttggaca                                               20

<210> SEQ ID NO 187
<211> LENGTH: 20
<212> TYPE: DNA
<213> ORGANISM: Human

<400> SEQUENCE: 187
cgaccttgtt tctcataact                                               20

<210> SEQ ID NO 188
<211> LENGTH: 20
<212> TYPE: DNA
<213> ORGANISM: Human

<400> SEQUENCE: 188
gcttttacaa ctttgcggac                                               20

<210> SEQ ID NO 189
<211> LENGTH: 20
<212> TYPE: DNA
<213> ORGANISM: Human

<400> SEQUENCE: 189
gagactcaat gatggcatac                                               20

<210> SEQ ID NO 190
<211> LENGTH: 20
<212> TYPE: DNA
<213> ORGANISM: Human

<400> SEQUENCE: 190
tgctgcattt gatggttccc                                               20

<210> SEQ ID NO 191
<211> LENGTH: 20
<212> TYPE: DNA
<213> ORGANISM: Human

<400> SEQUENCE: 191
cctcatcttt gctggtgtac                                        20

<210> SEQ ID NO 192
<211> LENGTH: 20
<212> TYPE: DNA
<213> ORGANISM: Human

<400> SEQUENCE: 192
tgacttcagc caacttctta                                        20

<210> SEQ ID NO 193
<211> LENGTH: 20
<212> TYPE: DNA
<213> ORGANISM: Human

<400> SEQUENCE: 193
tttattcaag tttcggacaa                                        20

<210> SEQ ID NO 194
<211> LENGTH: 20
<212> TYPE: DNA
<213> ORGANISM: Human

<400> SEQUENCE: 194
atgcctctgg tacaggatag                                        20

<210> SEQ ID NO 195
<211> LENGTH: 20
<212> TYPE: DNA
<213> ORGANISM: Human

<400> SEQUENCE: 195
gggcgatggc gtttatttga                                        20

<210> SEQ ID NO 196
<211> LENGTH: 20
<212> TYPE: DNA
<213> ORGANISM: Human

<400> SEQUENCE: 196
agaccttgta ccccaattcc                                        20

<210> SEQ ID NO 197
<211> LENGTH: 20
<212> TYPE: DNA
<213> ORGANISM: Human

<400> SEQUENCE: 197
caggataaaa gcatctgcca                                        20

<210> SEQ ID NO 198
<211> LENGTH: 20
<212> TYPE: DNA
<213> ORGANISM: Human

<400> SEQUENCE: 198 tcaaagggt atctcatcag                                         20

<210> SEQ ID NO 199
<211> LENGTH: 20
<212> TYPE: DNA
<213> ORGANISM: Human

<400> SEQUENCE: 199
agagccctca taggtttcgt                                              20

<210> SEQ ID NO 200
<211> LENGTH: 20
<212> TYPE: DNA
<213> ORGANISM: Human

<400> SEQUENCE: 200
gagagccctc ataggtttcg                                              20

<210> SEQ ID NO 201
<211> LENGTH: 20
<212> TYPE: DNA
<213> ORGANISM: Human

<400> SEQUENCE: 201
cccataggtc tgtaggagta                                              20

<210> SEQ ID NO 202
<211> LENGTH: 20
<212> TYPE: DNA
<213> ORGANISM: Human

<400> SEQUENCE: 202
attattcccc aggatctgag                                              20

<210> SEQ ID NO 203
<211> LENGTH: 20
<212> TYPE: DNA
<213> ORGANISM: Human

<400> SEQUENCE: 203
gatgttgctg gtgtaaggtt                                              20

<210> SEQ ID NO 204
<211> LENGTH: 20
<212> TYPE: DNA
<213> ORGANISM: Human

<400> SEQUENCE: 204
tctcctgaca agactctgcg                                              20

<210> SEQ ID NO 205
<211> LENGTH: 20
<212> TYPE: DNA
<213> ORGANISM: Human

<400> SEQUENCE: 205
gatttcccac acagttttat                                              20

<210> SEQ ID NO 206
<211> LENGTH: 20
<212> TYPE: DNA
<213> ORGANISM: Human

<400> SEQUENCE: 206

-continued

```
gtgagtttgc catagttagg                                               20

<210> SEQ ID NO 207
<211> LENGTH: 20
<212> TYPE: DNA
<213> ORGANISM: Human

<400> SEQUENCE: 207
caaaccctgc ttccagccgt                                               20

<210> SEQ ID NO 208
<211> LENGTH: 20
<212> TYPE: DNA
<213> ORGANISM: Human

<400> SEQUENCE: 208
ggtctcgtcc ttaaataata                                               20

<210> SEQ ID NO 209
<211> LENGTH: 20
<212> TYPE: DNA
<213> ORGANISM: Human

<400> SEQUENCE: 209
agtttggcta ctgaagacat                                               20

<210> SEQ ID NO 210
<211> LENGTH: 20
<212> TYPE: DNA
<213> ORGANISM: Human

<400> SEQUENCE: 210
caattactcc ttttgcctgc                                               20

<210> SEQ ID NO 211
<211> LENGTH: 20
<212> TYPE: DNA
<213> ORGANISM: Human

<400> SEQUENCE: 211
tccctgtatg caagatgact                                               20

<210> SEQ ID NO 212
<211> LENGTH: 20
<212> TYPE: DNA
<213> ORGANISM: Human

<400> SEQUENCE: 212
cccaccagtc aaagcagtaa                                               20

<210> SEQ ID NO 213
<211> LENGTH: 20
<212> TYPE: DNA
<213> ORGANISM: Human

<400> SEQUENCE: 213
ccagataaag gtcctatcag                                               20

<210> SEQ ID NO 214
<211> LENGTH: 20
<212> TYPE: DNA
<213> ORGANISM: Human

<400> SEQUENCE: 214
```

```
actgcagcct atatgcagct                                          20

<210> SEQ ID NO 215
<211> LENGTH: 20
<212> TYPE: DNA
<213> ORGANISM: Human

<400> SEQUENCE: 215
ctctagcgtc atatagccga                                          20

<210> SEQ ID NO 216
<211> LENGTH: 20
<212> TYPE: DNA
<213> ORGANISM: Human

<400> SEQUENCE: 216
tcccgcctgt gacatgcatt                                          20

<210> SEQ ID NO 217
<211> LENGTH: 20
<212> TYPE: DNA
<213> ORGANISM: Human

<400> SEQUENCE: 217
gttctcgctg gtgagtttca                                          20

<210> SEQ ID NO 218
<211> LENGTH: 18
<212> TYPE: DNA
<213> ORGANISM: Human

<400> SEQUENCE: 218
tctcccagcg tgcgccat                                            18

<210> SEQ ID NO 219
<211> LENGTH: 15
<212> TYPE: DNA
<213> ORGANISM: Human

<400> SEQUENCE: 219
aacgttgagg ggcat                                               15

<210> SEQ ID NO 220
<211> LENGTH: 24
<212> TYPE: DNA
<213> ORGANISM: Human

<400> SEQUENCE: 220
tatgctgtgc cggggtcttc gggc                                     24
```